US010591391B2

(12) United States Patent
Stoughton et al.

(10) Patent No.: US 10,591,391 B2
(45) Date of Patent: Mar. 17, 2020

(54) DIAGNOSIS OF FETAL ABNORMALITIES USING POLYMORPHISMS INCLUDING SHORT TANDEM REPEATS

(71) Applicants: Verinata Health, Inc., Redwood City, CA (US); The General Hospital Corporation, Boston, MA (US); GPB Scientific, LLC, Richmond, VA (US)

(72) Inventors: Roland Stoughton, The Sea Ranch, CA (US); Ravi Kapur, Sharon, MA (US); Barb Ariel Cohen, Watertown, MA (US); Daniel Shoemaker, San Diego, CA (US); Ronald W. Davis, Palo Alto, CA (US); Mehmet Toner, Charlestown, MA (US)

(73) Assignees: Verinata Health, Inc., Redwood City, CA (US); The General Hospital Corporation, Boston, MA (US); GPB Scientific, LLC, Richmond, VA (US)

( * ) Notice: Subject to any disclaimer, the term of this patent is extended or adjusted under 35 U.S.C. 154(b) by 13 days.

(21) Appl. No.: 13/830,871

(22) Filed: Mar. 14, 2013

(65) Prior Publication Data

US 2013/0280709 A1    Oct. 24, 2013

Related U.S. Application Data

(63) Continuation of application No. 13/738,268, filed on Jan. 10, 2013, which is a continuation of application No. 13/433,232, filed on Mar. 28, 2012, now abandoned, which is a continuation of application No. 12/725,240, filed on Mar. 16, 2010, now abandoned, which is a continuation of application No. 11/763,426, filed on Jun. 14, 2007, now abandoned.

(60) Provisional application No. 60/804,815, filed on Jun. 14, 2006, provisional application No. 60/820,778, filed on Jul. 28, 2006.

(51) Int. Cl.
*G01N 1/30* (2006.01)
*C12Q 1/6883* (2018.01)
*G16B 20/00* (2019.01)

(52) U.S. Cl.
CPC ............ *G01N 1/30* (2013.01); *C12Q 1/6883* (2013.01); *C12Q 2600/156* (2013.01); *C12Q 2600/158* (2013.01); *C12Q 2600/16* (2013.01); *G16B 20/00* (2019.02)

(58) Field of Classification Search
CPC ............ C12Q 1/6883; C12Q 2600/156; C12Q 2600/158; C12Q 2600/16; C12Q 1/6874; G01N 1/30; G06F 19/18
See application file for complete search history.

(56) References Cited

U.S. PATENT DOCUMENTS

| | | |
|---|---|---|
| 4,508,625 A | 9/1985 | Graham |
| 4,675,286 A | 6/1987 | Calenoff |
| 4,683,202 A | 7/1987 | Mullis |
| 4,789,628 A | 12/1988 | Nayak |
| 4,800,159 A | 1/1989 | Mullis et al. |
| 4,971,904 A | 11/1990 | Luddy |
| 4,977,078 A | 12/1990 | Niimura et al. |
| 5,153,117 A | 10/1992 | Simons |
| 5,215,926 A | 6/1993 | Etchells, III et al. |
| 5,296,375 A | 3/1994 | Kricka et al. |
| 5,300,779 A | 4/1994 | Hillman et al. |
| 5,302,509 A | 4/1994 | Cheeseman |
| 5,304,487 A | 4/1994 | Wilding et al. |
| 5,427,663 A | 6/1995 | Austin et al. |
| 5,427,946 A | 6/1995 | Kricka et al. |
| 5,432,054 A | 7/1995 | Saunders et al. |
| 5,447,842 A | 9/1995 | Simons |
| 5,486,335 A | 1/1996 | Wilding et al. |
| 5,498,392 A | 3/1996 | Wilding et al. |
| 5,508,169 A | 4/1996 | Deugau et al. |
| 5,529,903 A | 6/1996 | Kübler et al. |
| 5,556,773 A | 9/1996 | Youmo |
| 5,629,147 A | 5/1997 | Asgari et al. |
| 5,639,669 A | 6/1997 | Ledley |
| 5,641,628 A | 6/1997 | Bianchi |
| 5,646,001 A | 7/1997 | Terstappen et al. |
| 5,670,325 A | 9/1997 | Lapidus et al. |
| 5,676,849 A | 10/1997 | Sammons et al. |
| 5,695,934 A | 12/1997 | Brenner |

(Continued)

FOREIGN PATENT DOCUMENTS

| | | |
|---|---|---|
| AU | 2007260676 A1 | 12/2007 |
| CA | 2655272 A1 | 12/2007 |

(Continued)

OTHER PUBLICATIONS

Illumina Technical Note: Reproductive Health, pp. 1-5 (2014).*

(Continued)

*Primary Examiner* — Teresa E Strzelecka

(74) *Attorney, Agent, or Firm* — Fish & Richardson P.C.

(57) ABSTRACT

The present invention provides systems, apparatuses, and methods to detect the presence of fetal cells when mixed with a population of maternal cells in a sample and to test fetal abnormalities, i.e. aneuploidy. In addition, the present invention provides methods to determine when there are insufficient fetal cells for a determination and report a non-informative case. The present invention involves quantifying regions of genomic DNA from a mixed sample. More particularly the invention involves quantifying DNA polymorphisms from the mixed sample.

17 Claims, 28 Drawing Sheets

Specification includes a Sequence Listing.

(56) References Cited

U.S. PATENT DOCUMENTS

| | | |
|---|---|---|
| 5,707,799 A | 1/1998 | Hansmann et al. |
| 5,709,943 A | 1/1998 | Coleman et al. |
| 5,715,946 A | 2/1998 | Reichenbach |
| 5,726,026 A | 3/1998 | Wilding et al. |
| 5,750,339 A | 5/1998 | Smith |
| 5,766,843 A | 6/1998 | Asgari et al. |
| 5,770,029 A | 6/1998 | Nelson et al. |
| 5,798,042 A | 8/1998 | Chu et al. |
| 5,837,115 A | 11/1998 | Austin et al. |
| 5,840,502 A | 11/1998 | Van Vlasselaer |
| 5,842,787 A | 12/1998 | Koph-Sill et al. |
| 5,858,649 A | 1/1999 | Asgari et al. |
| 5,866,345 A | 2/1999 | Wilding et al. |
| 5,879,883 A | 3/1999 | Benson et al. |
| 5,891,651 A | 4/1999 | Roche et al. |
| 5,928,880 A | 7/1999 | Wilding et al. |
| 5,952,173 A | 9/1999 | Hansmann et al. |
| 5,962,234 A | 10/1999 | Golbus |
| 5,962,237 A | 10/1999 | Ts'o et al. |
| 5,962,332 A | 10/1999 | Singer et al. |
| 5,972,721 A | 10/1999 | Bruno et al. |
| 5,993,665 A | 11/1999 | Terstappen et al. |
| 5,994,057 A | 11/1999 | Mansfield |
| 5,994,517 A | 11/1999 | Ts'o et al. |
| 6,007,690 A | 12/1999 | Nelson et al. |
| 6,008,007 A | 12/1999 | Fruehauf et al. |
| 6,013,188 A | 1/2000 | Terstappen et al. |
| 6,027,923 A | 2/2000 | Wallace |
| 6,066,449 A | 5/2000 | Ditkoff et al. |
| 6,074,827 A | 6/2000 | Nelson et al. |
| 6,100,029 A | 8/2000 | Lapidus et al. |
| 6,124,120 A | 9/2000 | Lizardi |
| 6,159,685 A | 10/2000 | Pinkel et al. |
| 6,143,496 A | 11/2000 | Brown et al. |
| 6,143,576 A | 11/2000 | Buechler |
| 6,154,707 A | 11/2000 | Livak et al. |
| 6,156,270 A | 12/2000 | Buechler |
| 6,176,962 B1 | 1/2001 | Soane et al. |
| 6,184,029 B1 | 2/2001 | Wilding et al. |
| 6,184,043 B1 | 2/2001 | Fodstad et al. |
| 6,186,660 B1 | 2/2001 | Koph-Sill et al. |
| 6,190,870 B1 | 2/2001 | Schmitz et al. |
| 6,197,523 B1 | 3/2001 | Rimm et al. |
| 6,200,765 B1 | 3/2001 | Murphy et al. |
| 6,210,891 B1 | 4/2001 | Nyren et al. |
| 6,214,558 B1 | 4/2001 | Shuber et al. |
| 6,235,474 B1 | 5/2001 | Feinberg |
| 6,258,540 B1 | 7/2001 | Lo et al. |
| 6,265,229 B1 | 7/2001 | Fodstad et al. |
| 6,300,077 B1 | 10/2001 | Shuber et al. |
| 6,329,150 B1 | 12/2001 | Lizardi et al. |
| 6,344,326 B1 | 2/2002 | Nelson et al. |
| 6,361,958 B1 | 3/2002 | Shieh et al. |
| 6,365,362 B1 | 4/2002 | Terstappen et al. |
| 6,368,871 B1 | 4/2002 | Christel et al. |
| 6,376,181 B2 | 4/2002 | Ramsey et al. |
| 6,383,759 B1 | 5/2002 | Murphy et al. |
| 6,387,707 B1 | 5/2002 | Seul et al. |
| 6,391,559 B1 | 5/2002 | Brown et al. |
| 6,394,942 B2 | 5/2002 | Moon et al. |
| 6,399,364 B1 | 6/2002 | Reeve et al. |
| 6,432,630 B1 | 8/2002 | Blankenstein |
| 6,440,706 B1 | 8/2002 | Vogelstein et al. |
| 6,444,461 B1 | 9/2002 | Knapp et al. |
| 6,454,938 B2 | 9/2002 | Moon et al. |
| 6,479,299 B1 | 11/2002 | Parce et al. |
| 6,511,967 B1 | 1/2003 | Weissleder et al. |
| 6,517,234 B1 | 2/2003 | Koph-Sill et al. |
| 6,540,895 B1 | 4/2003 | Spence et al. |
| 6,566,101 B1 | 5/2003 | Shuber et al. |
| 6,576,478 B1 | 6/2003 | Wagner et al. |
| 6,582,904 B2 | 6/2003 | Dahm |
| 6,582,969 B1 | 6/2003 | Wagner et al. |
| 6,596,144 B1 | 7/2003 | Regnier et al. |
| 6,596,545 B1 | 7/2003 | Wagner et al. |
| 6,613,525 B2 | 9/2003 | Nelson et al. |
| 6,618,679 B2 | 9/2003 | Loehriein et al. |
| 6,632,619 B1 | 10/2003 | Harrison et al. |
| 6,632,652 B1 | 10/2003 | Austin et al. |
| 6,632,655 B1 | 10/2003 | Mehta et al. |
| 6,637,463 B1 | 10/2003 | Lei et al. |
| 6,645,731 B2 | 11/2003 | Terstappen et al. |
| 6,664,056 B2 | 12/2003 | Lo et al. |
| 6,664,104 B2 | 12/2003 | Pourahmadi et al. |
| 6,673,541 B1 | 1/2004 | Klein et al. |
| 6,674,525 B2 | 1/2004 | Bardell et al. |
| 6,685,841 B2 | 2/2004 | Lopez et al. |
| 6,689,615 B1 | 2/2004 | Murto et al. |
| 6,746,503 B1 | 6/2004 | Benett et al. |
| 6,753,147 B2 | 6/2004 | Vogelstein et al. |
| 6,783,928 B2 | 8/2004 | Hvichia et al. |
| 6,818,184 B2 | 11/2004 | Fulwyler et al. |
| 6,830,936 B2 | 12/2004 | Anderson et al. |
| 6,858,439 B1 | 2/2005 | Xu et al. |
| 6,875,619 B2 | 4/2005 | Blackburn |
| 6,893,881 B1 | 5/2005 | Fodstad et al. |
| 6,906,182 B2 | 6/2005 | Ts'o et al. |
| 6,911,345 B2 | 6/2005 | Quake et al. |
| 6,913,697 B2 | 7/2005 | Lopez et al. |
| 6,927,028 B2 | 8/2005 | Lo et al. |
| 6,953,668 B1 | 10/2005 | Israeli et al. |
| 6,960,449 B2 | 11/2005 | Wang et al. |
| 7,115,709 B1 | 10/2006 | Gray et al. |
| 7,150,812 B2 | 12/2006 | Huang et al. |
| 7,171,975 B2 | 2/2007 | Moon et al. |
| 7,190,818 B2 | 3/2007 | Ellis et al. |
| 7,192,698 B1 | 3/2007 | Kinch et al. |
| 7,198,787 B2 | 4/2007 | Fodstad et al. |
| 7,208,275 B2 | 4/2007 | Gocke et al. |
| 7,208,295 B2 | 4/2007 | Faham et al. |
| 7,212,660 B2 | 5/2007 | Wetzel et al. |
| 7,220,594 B2 | 5/2007 | Foster et al. |
| 7,227,002 B1 | 6/2007 | Kufer et al. |
| 7,229,838 B2 | 6/2007 | Foster et al. |
| 7,250,256 B2 | 7/2007 | Reinhard et al. |
| 7,252,976 B2 | 8/2007 | Lin et al. |
| 7,258,987 B2 | 8/2007 | Lamorte et al. |
| 7,262,177 B2 | 8/2007 | Ts'o et al. |
| 7,262,269 B2 | 8/2007 | Lam et al. |
| 7,264,972 B2 | 9/2007 | Foster |
| 7,272,252 B2 | 9/2007 | De La Torre-Bueno et al. |
| 7,276,170 B2 | 10/2007 | Oakey et al. |
| 7,332,277 B2 | 2/2008 | Dhallan |
| 7,407,757 B2 | 8/2008 | Brenner |
| 7,442,506 B2 | 10/2008 | Dhallan |
| 7,476,363 B2 | 1/2009 | Unger et al. |
| 7,582,420 B2 | 9/2009 | Oliphant et al. |
| 7,645,576 B2 | 1/2010 | Lo et al. |
| 7,655,399 B2 | 2/2010 | Cantor et al. |
| 7,709,194 B2 | 5/2010 | Lo et al. |
| 7,718,367 B2 | 5/2010 | Lo et al. |
| 7,727,720 B2 | 6/2010 | Dhallan et al. |
| 7,754,428 B2 | 7/2010 | Lo et al. |
| 7,799,531 B2 | 9/2010 | Mitchell et al. |
| 7,838,647 B2 | 11/2010 | Hahn et al. |
| 7,888,017 B2 | 2/2011 | Quake et al. |
| RE42,315 E | 5/2011 | Lopez et al. |
| 7,955,794 B2 | 6/2011 | Shen et al. |
| 8,003,354 B2 | 8/2011 | Shen et al. |
| 8,008,018 B2 | 8/2011 | Quake et al. |
| 8,024,128 B2 | 9/2011 | Rabinowitz et al. |
| 8,137,912 B2 | 3/2012 | Kapur et al. |
| 8,168,389 B2 | 5/2012 | Shoemaker et al. |
| 8,195,415 B2 | 6/2012 | Fan et al. |
| 8,293,470 B2 | 10/2012 | Quake et al. |
| 8,296,076 B2 | 10/2012 | Fan et al. |
| 8,318,430 B2 | 11/2012 | Chuu et al. |
| 8,372,584 B2 | 2/2013 | Shoemaker et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 9,017,942 B2 | 4/2015 | Shoemaker et al. |
| 9,347,100 B2 | 5/2016 | Shoemaker et al. |
| 9,441,273 B2 | 9/2016 | Quake et al. |

(56) References Cited

U.S. PATENT DOCUMENTS

| | | |
|---|---|---|
| 2001/0007749 A1 | 7/2001 | Feinberg |
| 2001/0051341 A1 | 12/2001 | Lo et al. |
| 2001/0053958 A1 | 12/2001 | Ried et al. |
| 2002/0006621 A1 | 1/2002 | Bianchi |
| 2002/0009738 A1 | 1/2002 | Houghton et al. |
| 2002/0012930 A1 | 1/2002 | Rothberg et al. |
| 2002/0012931 A1 | 1/2002 | Waldman et al. |
| 2002/0016450 A1 | 2/2002 | Laugharn et al. |
| 2002/0019001 A1 | 2/2002 | Light |
| 2002/0028431 A1 | 3/2002 | Julien |
| 2002/0058332 A1 | 5/2002 | Quake et al. |
| 2002/0076825 A1 | 6/2002 | Cheng et al. |
| 2002/0086329 A1 | 7/2002 | Shvets et al. |
| 2002/0110835 A1 | 8/2002 | Kumar |
| 2002/0119469 A1 | 8/2002 | Shuber et al. |
| 2002/0123078 A1 | 9/2002 | Seul et al. |
| 2002/0127575 A1 | 9/2002 | Hoke et al. |
| 2002/0137088 A1 | 9/2002 | Bianchi |
| 2002/0164816 A1 | 11/2002 | Quake |
| 2002/0166760 A1 | 11/2002 | Prentiss et al. |
| 2002/0172987 A1 | 11/2002 | Terstappen et al. |
| 2003/0004402 A1 | 1/2003 | Hitt et al. |
| 2003/0013101 A1 | 1/2003 | Balasubramanian |
| 2003/0017514 A1 | 1/2003 | Pachmann et al. |
| 2003/0022207 A1 | 1/2003 | Balasubramanian |
| 2003/0033091 A1 | 2/2003 | Opalsky et al. |
| 2003/0044388 A1 | 3/2003 | Lo et al. |
| 2003/0044781 A1 | 3/2003 | Korlach et al. |
| 2003/0072682 A1 | 4/2003 | Kikinis |
| 2003/0077292 A1 | 4/2003 | Hanash et al. |
| 2003/0082566 A1 | 5/2003 | Sylvan |
| 2003/0100102 A1 | 5/2003 | Rothberg et al. |
| 2003/0119077 A1 | 6/2003 | Ts'o et al. |
| 2003/0119724 A1 | 6/2003 | Ts'o et al. |
| 2003/0129676 A1 | 7/2003 | Terstappen et al. |
| 2003/0152981 A1 | 8/2003 | Hulten |
| 2003/0153085 A1 | 8/2003 | Leary et al. |
| 2003/0159999 A1 | 8/2003 | Oakey et al. |
| 2003/0165852 A1 | 9/2003 | Schueler et al. |
| 2003/0170631 A1 | 9/2003 | Houghton et al. |
| 2003/0170703 A1 | 9/2003 | Piper et al. |
| 2003/0175990 A1 | 9/2003 | Heyenga |
| 2003/0186255 A1 | 10/2003 | Williams et al. |
| 2003/0190602 A1 | 10/2003 | Pressman et al. |
| 2003/0199685 A1 | 10/2003 | Pressman et al. |
| 2003/0204331 A1 | 10/2003 | Whitney et al. |
| 2003/0206901 A1 | 11/2003 | Chen |
| 2003/0219765 A1 | 11/2003 | Costa |
| 2003/0231791 A1 | 12/2003 | Torre-Bueno et al. |
| 2003/0232350 A1 | 12/2003 | Afar et al. |
| 2004/0005582 A1 | 1/2004 | Shipwash |
| 2004/0009471 A1 | 1/2004 | Cao |
| 2004/0018116 A1 | 1/2004 | Desmond et al. |
| 2004/0018509 A1 | 1/2004 | Bianchi |
| 2004/0043506 A1 | 3/2004 | Haussecker et al. |
| 2004/0048360 A1 | 3/2004 | Wada et al. |
| 2004/0053352 A1 | 3/2004 | Ouyang et al. |
| 2004/0072278 A1 | 4/2004 | Chou et al. |
| 2004/0096892 A1 | 5/2004 | Wang et al. |
| 2004/0137452 A1 | 7/2004 | Levett et al. |
| 2004/0137470 A1 | 7/2004 | Dhallan |
| 2004/0142463 A1 | 7/2004 | Walker et al. |
| 2004/0144651 A1 | 7/2004 | Huang et al. |
| 2004/0157243 A1 | 8/2004 | Huang et al. |
| 2004/0166555 A1 | 8/2004 | Braff et al. |
| 2004/0171091 A1 | 9/2004 | Lesko et al. |
| 2004/0185495 A1 | 9/2004 | Schueler et al. |
| 2004/0203037 A1 | 10/2004 | Lo et al. |
| 2004/0209299 A1 | 10/2004 | Pinter et al. |
| 2004/0214240 A1 | 10/2004 | Cao |
| 2004/0232074 A1 | 11/2004 | Peters et al. |
| 2004/0241707 A1 | 12/2004 | Gao et al. |
| 2005/0014208 A1 | 1/2005 | Krehan et al. |
| 2005/0019792 A1 | 1/2005 | McBride et al. |
| 2005/0037388 A1 | 2/2005 | Antonarakis et al. |
| 2005/0042623 A1 | 2/2005 | Ault-Riche et al. |
| 2005/0042685 A1 | 2/2005 | Albert et al. |
| 2005/0049793 A1 | 3/2005 | Paterlini-Brechot |
| 2005/0061962 A1 | 3/2005 | Mueth et al. |
| 2005/0064476 A1 | 3/2005 | Huang et al. |
| 2005/0095606 A1 | 5/2005 | Hoke et al. |
| 2005/0100932 A1 | 5/2005 | Lapidus et al. |
| 2005/0118591 A1 | 6/2005 | Tamak et al. |
| 2005/0129581 A1 | 6/2005 | McBride et al. |
| 2005/0130217 A1 | 6/2005 | Huang et al. |
| 2005/0145496 A1 | 7/2005 | Goodsaid et al. |
| 2005/0147977 A1 | 7/2005 | Koo et al. |
| 2005/0153342 A1 | 7/2005 | Chen |
| 2005/0158754 A1 | 7/2005 | Puffenberger et al. |
| 2005/0164241 A1 | 7/2005 | Hahn et al. |
| 2005/0175996 A1 | 8/2005 | Chen |
| 2005/0181353 A1 | 8/2005 | Rao et al. |
| 2005/0181463 A1 | 8/2005 | Rao et al. |
| 2005/0196785 A1 | 9/2005 | Quake et al. |
| 2005/0207940 A1 | 9/2005 | Butler et al. |
| 2005/0211556 A1 | 9/2005 | Childers et al. |
| 2005/0214855 A1 | 9/2005 | Wagner et al. |
| 2005/0221341 A1 | 10/2005 | Shimkets et al. |
| 2005/0221373 A1 | 10/2005 | Enzelberger et al. |
| 2005/0239101 A1 | 10/2005 | Sukumar et al. |
| 2005/0244843 A1 | 11/2005 | Chen et al. |
| 2005/0250111 A1 | 11/2005 | Xie et al. |
| 2005/0250147 A1 | 11/2005 | Macevicz |
| 2005/0250155 A1 | 11/2005 | Lesko et al. |
| 2005/0250199 A1 | 11/2005 | Anderson et al. |
| 2005/0252773 A1 | 11/2005 | McBride et al. |
| 2005/0255001 A1 | 11/2005 | Padmanabhan et al. |
| 2005/0262577 A1 | 11/2005 | Guelly et al. |
| 2005/0266433 A1 | 12/2005 | Kapur et al. |
| 2005/0272103 A1 | 12/2005 | Chen |
| 2005/0282196 A1 | 12/2005 | Costa |
| 2005/0282293 A1 | 12/2005 | Cosmen et al. |
| 2005/0287611 A1 | 12/2005 | Nugent et al. |
| 2006/0000772 A1 | 1/2006 | Sano et al. |
| 2006/0008807 A1 | 1/2006 | O'Hara et al. |
| 2006/0008824 A1 | 1/2006 | Ronaghi et al. |
| 2006/0024678 A1 | 2/2006 | Buzby |
| 2006/0024711 A1 | 2/2006 | Lapidus et al. |
| 2006/0024756 A1 | 2/2006 | Tibbe et al. |
| 2006/0046258 A1 | 3/2006 | Lapidus et al. |
| 2006/0051265 A1 | 3/2006 | Mohamed et al. |
| 2006/0051775 A1 | 3/2006 | Bianchi et al. |
| 2006/0052945 A1 | 3/2006 | Rabinowitz et al. |
| 2006/0060767 A1 | 3/2006 | Wang et al. |
| 2006/0072805 A1 | 4/2006 | Tsipouras et al. |
| 2006/0073125 A1 | 4/2006 | Clarke et al. |
| 2006/0094109 A1 | 5/2006 | Trainer |
| 2006/0121452 A1 | 6/2006 | Dhallan |
| 2006/0121624 A1 | 6/2006 | Huang et al. |
| 2006/0128006 A1 | 6/2006 | Gerhardt et al. |
| 2006/0134599 A1 | 6/2006 | Toner et al. |
| 2006/0160105 A1 | 7/2006 | Dhallan |
| 2006/0160150 A1 | 7/2006 | Seilhamer et al. |
| 2006/0160243 A1 | 7/2006 | Tang et al. |
| 2006/0177832 A1 | 8/2006 | Brenner |
| 2006/0183886 A1 | 8/2006 | Ts'o et al. |
| 2006/0205057 A1 | 9/2006 | Wayner et al. |
| 2006/0223178 A1 | 10/2006 | Barber et al. |
| 2006/0228721 A1 | 10/2006 | Leamon et al. |
| 2006/0252054 A1 | 11/2006 | Lin et al. |
| 2006/0252061 A1 | 11/2006 | Zabeau et al. |
| 2006/0252068 A1 | 11/2006 | Lo et al. |
| 2006/0252071 A1 | 11/2006 | Lo et al. |
| 2006/0252087 A1 | 11/2006 | Tang et al. |
| 2007/0015171 A1 | 1/2007 | Bianchi et al. |
| 2007/0017633 A1 | 1/2007 | Tonkovich et al. |
| 2007/0026381 A1 | 2/2007 | Huang et al. |
| 2007/0026413 A1 | 2/2007 | Toner et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |

(56) References Cited

U.S. PATENT DOCUMENTS

| | | |
|---|---|---|
| 2007/0026469 A1 | 2/2007 | Fuchs et al. |
| 2007/0027636 A1 | 2/2007 | Rabinowitz |
| 2007/0037172 A1 | 2/2007 | Chiu et al. |
| 2007/0037173 A1 | 2/2007 | Allard et al. |
| 2007/0037273 A1 | 2/2007 | Shuler et al. |
| 2007/0037275 A1 | 2/2007 | Shuler et al. |
| 2007/0042238 A1 | 2/2007 | Kim et al. |
| 2007/0042339 A1 | 2/2007 | Toner et al. |
| 2007/0042360 A1 | 2/2007 | Afar et al. |
| 2007/0042368 A1 | 2/2007 | Zehentner-Wilkinson et al. |
| 2007/0048750 A1 | 3/2007 | Peck et al. |
| 2007/0054268 A1 | 3/2007 | Sutherland et al. |
| 2007/0054287 A1 | 3/2007 | Bloch |
| 2007/0059680 A1 | 3/2007 | Kapur et al. |
| 2007/0059683 A1 | 3/2007 | Barber et al. |
| 2007/0059710 A1 | 3/2007 | Luke et al. |
| 2007/0059716 A1 | 3/2007 | Balis et al. |
| 2007/0059718 A1 | 3/2007 | Toner et al. |
| 2007/0059719 A1 | 3/2007 | Grisham et al. |
| 2007/0059737 A1 | 3/2007 | Baker et al. |
| 2007/0059774 A1 | 3/2007 | Grisham et al. |
| 2007/0059781 A1 | 3/2007 | Kapur et al. |
| 2007/0059785 A1 | 3/2007 | Bacus et al. |
| 2007/0065845 A1 | 3/2007 | Baker et al. |
| 2007/0065858 A1 | 3/2007 | Haley |
| 2007/0071762 A1 | 3/2007 | Ts'o et al. |
| 2007/0072228 A1 | 3/2007 | Brauch |
| 2007/0072290 A1 | 3/2007 | Hvichia |
| 2007/0077578 A1 | 4/2007 | Penning et al. |
| 2007/0092444 A1 | 4/2007 | Benos et al. |
| 2007/0092881 A1 | 4/2007 | Ohnishi et al. |
| 2007/0092917 A1 | 4/2007 | Guyon |
| 2007/0099207 A1 | 5/2007 | Fuchs et al. |
| 2007/0099219 A1 | 5/2007 | Teverovskiy et al. |
| 2007/0099289 A1 | 5/2007 | Irimia et al. |
| 2007/0105105 A1 | 5/2007 | Clelland et al. |
| 2007/0105133 A1 | 5/2007 | Clark et al. |
| 2007/0110773 A1 | 5/2007 | Asina et al. |
| 2007/0117158 A1 | 5/2007 | Coumans et al. |
| 2007/0122856 A1 | 5/2007 | Georges et al. |
| 2007/0122896 A1 | 5/2007 | Shuler et al. |
| 2007/0128655 A1 | 6/2007 | Obata |
| 2007/0131622 A1 | 6/2007 | Oakey et al. |
| 2007/0134658 A1 | 6/2007 | Bohmer et al. |
| 2007/0134713 A1 | 6/2007 | Cao |
| 2007/0135621 A1 | 6/2007 | Bourel et al. |
| 2007/0141587 A1 | 6/2007 | Baker et al. |
| 2007/0141588 A1 | 6/2007 | Baker et al. |
| 2007/0141717 A1 | 6/2007 | Carpenter et al. |
| 2007/0154928 A1 | 7/2007 | Mack et al. |
| 2007/0154960 A1 | 7/2007 | Connelly et al. |
| 2007/0160503 A1 | 7/2007 | Sethu et al. |
| 2007/0160974 A1 | 7/2007 | Sidhu et al. |
| 2007/0160984 A1 | 7/2007 | Huang et al. |
| 2007/0161064 A1 | 7/2007 | Kinch et al. |
| 2007/0166770 A1 | 7/2007 | Hsieh et al. |
| 2007/0170811 A1 | 7/2007 | Rubel |
| 2007/0172903 A1 | 7/2007 | Toner et al. |
| 2007/0178067 A1 | 8/2007 | Maier et al. |
| 2007/0178458 A1 | 8/2007 | O'Brien et al. |
| 2007/0178478 A1 | 8/2007 | Dhallan et al. |
| 2007/0178501 A1 | 8/2007 | Rabinowitz et al. |
| 2007/0187250 A1 | 8/2007 | Huang et al. |
| 2007/0196663 A1 | 8/2007 | Schwartz et al. |
| 2007/0196820 A1 | 8/2007 | Kapur et al. |
| 2007/0196840 A1 | 8/2007 | Roca et al. |
| 2007/0196869 A1 | 8/2007 | Perez et al. |
| 2007/0202106 A1 | 8/2007 | Palucka et al. |
| 2007/0202109 A1 | 8/2007 | Nakamura et al. |
| 2007/0202525 A1 | 8/2007 | Quake et al. |
| 2007/0202536 A1 | 8/2007 | Yamanishi et al. |
| 2007/0207351 A1 | 9/2007 | Christensen et al. |
| 2007/0207466 A1 | 9/2007 | Cantor et al. |
| 2007/0212689 A1 | 9/2007 | Bianchi et al. |
| 2007/0212698 A1 | 9/2007 | Bendele et al. |
| 2007/0212737 A1 | 9/2007 | Clarke et al. |
| 2007/0212738 A1 | 9/2007 | Haley et al. |
| 2007/0231851 A1 | 10/2007 | Toner et al. |
| 2007/0238105 A1 | 10/2007 | Barrett et al. |
| 2007/0259424 A1 | 11/2007 | Toner et al. |
| 2007/0264675 A1 | 11/2007 | Toner et al. |
| 2007/0275402 A1 | 11/2007 | Lo et al. |
| 2008/0020390 A1 | 1/2008 | Mitchell et al. |
| 2008/0023399 A1 | 1/2008 | Inglis et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0071076 A1 | 3/2008 | Hahn et al. |
| 2008/0090239 A1 | 4/2008 | Shoemaker et al. |
| 2008/0096216 A1 | 4/2008 | Quake |
| 2008/0096766 A1 | 4/2008 | Lee |
| 2008/0124721 A1 | 5/2008 | Fuchs |
| 2008/0138809 A1 | 6/2008 | Kapur et al. |
| 2008/0153090 A1 | 6/2008 | Lo et al. |
| 2008/0182261 A1 | 7/2008 | Bianchi |
| 2008/0193927 A1 | 8/2008 | Mann et al. |
| 2008/0213775 A1 | 9/2008 | Brody et al. |
| 2008/0220422 A1 | 9/2008 | Shoemaker et al. |
| 2008/0299562 A1 | 12/2008 | Oeth et al. |
| 2008/0318235 A1 | 12/2008 | Handyside |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0170113 A1 | 7/2009 | Quake et al. |
| 2009/0170114 A1 | 7/2009 | Quake et al. |
| 2009/0215633 A1 | 8/2009 | Van Eijk et al. |
| 2009/0280492 A1 | 11/2009 | Stoughton et al. |
| 2009/0291443 A1 | 11/2009 | Stoughton et al. |
| 2009/0317798 A1 | 12/2009 | Heid et al. |
| 2010/0094562 A1 | 4/2010 | Shohat et al. |
| 2010/0112575 A1 | 5/2010 | Fan et al. |
| 2010/0112590 A1 | 5/2010 | Lo et al. |
| 2010/0124751 A1 | 5/2010 | Quake et al. |
| 2010/0124752 A1 | 5/2010 | Quake et al. |
| 2010/0136529 A1 | 6/2010 | Shoemaker et al. |
| 2010/0216151 A1 | 8/2010 | Lapidus et al. |
| 2010/0216153 A1 | 8/2010 | Lapidus et al. |
| 2010/0255492 A1 | 10/2010 | Quake et al. |
| 2010/0255493 A1 | 10/2010 | Quake et al. |
| 2010/0256013 A1 | 10/2010 | Quake et al. |
| 2010/0291571 A1 | 11/2010 | Stoughton et al. |
| 2010/0291572 A1 | 11/2010 | Stoughton et al. |
| 2010/0311064 A1 | 12/2010 | Oliphant et al. |
| 2011/0003293 A1 | 1/2011 | Stoughton et al. |
| 2011/0015096 A1 | 1/2011 | Chiu et al. |
| 2011/0105353 A1 | 5/2011 | Lo et al. |
| 2011/0117548 A1 | 5/2011 | Mitchell et al. |
| 2011/0171638 A1 | 7/2011 | Stoughton et al. |
| 2011/0312503 A1 | 12/2011 | Chuu et al. |
| 2012/0010085 A1 | 1/2012 | Rava et al. |
| 2012/0135872 A1 | 5/2012 | Chuu et al. |
| 2012/0171666 A1 | 7/2012 | Shoemaker et al. |
| 2012/0171667 A1 | 7/2012 | Shoemaker et al. |
| 2012/0183963 A1 | 7/2012 | Stoughton et al. |
| 2012/0208186 A1 | 8/2012 | Kapur et al. |
| 2013/0189688 A1 | 7/2013 | Shoemaker et al. |
| 2013/0189689 A1 | 7/2013 | Shoemaker et al. |
| 2013/0210644 A1 | 8/2013 | Stoughton et al. |
| 2013/0253369 A1 | 9/2013 | Rabinowitz et al. |
| 2013/0288242 A1 | 10/2013 | Stoughton et al. |
| 2013/0288903 A1 | 10/2013 | Kapur et al. |
| 2013/0295565 A1 | 11/2013 | Shoemaker et al. |
| 2013/0324418 A1 | 12/2013 | Fuchs et al. |
| 2014/0032128 A1 | 1/2014 | Rabinowitz et al. |
| 2014/0087385 A1 | 3/2014 | Rabinowitz et al. |
| 2014/0106975 A1 | 4/2014 | Stoughton et al. |
| 2015/0232936 A1 | 8/2015 | Shoemaker et al. |

(56) References Cited

U.S. PATENT DOCUMENTS

| | | |
|---|---|---|
| 2015/0344956 A1 | 12/2015 | Kapur et al. |
| 2016/0002737 A1 | 1/2016 | Fuchs et al. |

FOREIGN PATENT DOCUMENTS

| | | |
|---|---|---|
| EP | 0637996 B1 | 7/1997 |
| EP | 0405972 B1 | 5/1999 |
| EP | 1262776 A2 | 12/2002 |
| EP | 0994963 B1 | 5/2003 |
| EP | 0970365 B1 | 10/2003 |
| EP | 783694 B1 | 11/2003 |
| EP | 1262776 A3 | 1/2004 |
| EP | 1388013 B1 | 2/2004 |
| EP | 0920627 B1 | 5/2004 |
| EP | 1418003 A1 | 5/2004 |
| EP | 0739240 B1 | 6/2004 |
| EP | 1462800 A1 | 9/2004 |
| EP | 0919812 B1 | 10/2004 |
| EP | 1561507 A1 | 8/2005 |
| EP | 1409727 B1 | 11/2005 |
| EP | 1272668 B1 | 2/2007 |
| EP | 1754788 A2 | 2/2007 |
| EP | 1757694 A2 | 2/2007 |
| EP | 1409745 B1 | 4/2007 |
| EP | 1754788 A3 | 4/2007 |
| EP | 1770171 A1 | 4/2007 |
| EP | 1313882 B1 | 5/2007 |
| EP | 1803822 A1 | 7/2007 |
| EP | 951645 B1 | 8/2007 |
| EP | 1813681 A2 | 8/2007 |
| EP | 1832661 A1 | 9/2007 |
| EP | 1757694 A3 | 2/2008 |
| EP | 2161347 A2 | 3/2010 |
| EP | 2161347 A3 | 6/2010 |
| EP | 2366801 A1 | 9/2011 |
| EP | 2423334 A2 | 2/2012 |
| EP | 2548972 A1 | 1/2013 |
| EP | 2589668 A1 | 5/2013 |
| EP | 1981995 B1 | 7/2013 |
| WO | WO 1990/06509 A1 | 6/1990 |
| WO | WO 1991/07660 A1 | 5/1991 |
| WO | WO 1991/016452 A1 | 10/1991 |
| WO | WO 1993/22053 A1 | 11/1993 |
| WO | WO 1994/29707 A1 | 12/1994 |
| WO | WO 1995/09245 A1 | 4/1995 |
| WO | WO 1997/46882 A1 | 12/1997 |
| WO | WO 1998/02528 A1 | 1/1998 |
| WO | WO 1998/10267 A1 | 3/1998 |
| WO | WO 98/39474 A1 | 9/1998 |
| WO | WO 99/22868 A1 | 5/1999 |
| WO | WO 1999/44064 A1 | 9/1999 |
| WO | WO 1999/061888 A2 | 12/1999 |
| WO | WO 00/06770 A1 | 2/2000 |
| WO | WO 00/40750 A1 | 7/2000 |
| WO | WO 2000/62931 A1 | 10/2000 |
| WO | WO 2001/35071 A2 | 5/2001 |
| WO | WO 2001/51668 A1 | 7/2001 |
| WO | WO 1999/061888 A3 | 12/2001 |
| WO | WO 2001/35071 A3 | 2/2002 |
| WO | WO 2002/012896 A1 | 2/2002 |
| WO | WO 2002/028523 A2 | 4/2002 |
| WO | WO 2002/030562 A1 | 4/2002 |
| WO | WO 2002/31506 A1 | 4/2002 |
| WO | WO 2002/44318 A1 | 6/2002 |
| WO | WO 2002/073204 A2 | 9/2002 |
| WO | WO 2003/003057 A2 | 1/2003 |
| WO | WO 03/020986 A1 | 3/2003 |
| WO | WO 2003/018757 A2 | 3/2003 |
| WO | WO 2003/019141 A2 | 3/2003 |
| WO | WO 2003/020974 A2 | 3/2003 |
| WO | WO 2003/023057 A2 | 3/2003 |
| WO | WO 2003/031938 A2 | 4/2003 |
| WO | WO 03/044217 A2 | 5/2003 |
| WO | WO 2003/035894 A2 | 5/2003 |
| WO | WO 2003/035895 A2 | 5/2003 |
| WO | WO 2003/044224 A1 | 5/2003 |
| WO | WO 2003/048295 A1 | 6/2003 |
| WO | WO 2003/069421 A2 | 8/2003 |
| WO | WO 2003/018757 A3 | 9/2003 |
| WO | WO 2003/020974 A3 | 9/2003 |
| WO | WO 03/044217 A3 | 10/2003 |
| WO | WO 2002/073204 A3 | 10/2003 |
| WO | WO 2003/031938 A3 | 11/2003 |
| WO | WO 2003/093795 A2 | 11/2003 |
| WO | WO 2003/023057 A3 | 12/2003 |
| WO | WO 2003/069421 A3 | 12/2003 |
| WO | WO 2003/035895 A3 | 1/2004 |
| WO | WO 2003/035894 A3 | 3/2004 |
| WO | WO 2004/025251 A2 | 3/2004 |
| WO | WO 2003/019141 A3 | 4/2004 |
| WO | WO 2004/029221 A2 | 4/2004 |
| WO | WO 2004/029221 A3 | 5/2004 |
| WO | WO 2004/037374 A2 | 5/2004 |
| WO | WO 2004/044236 A1 | 5/2004 |
| WO | WO 2004/056978 A1 | 7/2004 |
| WO | WO 2004/065629 A1 | 8/2004 |
| WO | WO 2004/076643 A2 | 9/2004 |
| WO | WO 2003/093795 A3 | 10/2004 |
| WO | WO 2004/037374 A3 | 10/2004 |
| WO | WO 2004/088310 A1 | 10/2004 |
| WO | WO 2004/025251 A3 | 11/2004 |
| WO | WO 2004/101762 A2 | 11/2004 |
| WO | WO 2004/113877 A1 | 12/2004 |
| WO | WO 2004/101762 A3 | 2/2005 |
| WO | WO 2005/023091 A2 | 3/2005 |
| WO | WO 2005/028663 A2 | 3/2005 |
| WO | WO 2005/035725 A2 | 4/2005 |
| WO | WO 2005/042713 A2 | 5/2005 |
| WO | WO 2005/043121 A2 | 5/2005 |
| WO | WO 2005/047529 A1 | 5/2005 |
| WO | WO 2005/047532 A1 | 5/2005 |
| WO | WO 2005/023091 A3 | 6/2005 |
| WO | WO 2005/049168 A2 | 6/2005 |
| WO | WO 2005/058937 A2 | 6/2005 |
| WO | WO 2005/061075 A1 | 7/2005 |
| WO | WO 2005/049168 A3 | 9/2005 |
| WO | WO 2005/084374 A2 | 9/2005 |
| WO | WO 2005/084380 A2 | 9/2005 |
| WO | WO 2005/085476 A1 | 9/2005 |
| WO | WO 2005/085861 A2 | 9/2005 |
| WO | WO 2005/098046 A2 | 10/2005 |
| WO | WO 2005/108621 A1 | 11/2005 |
| WO | WO 2005/109238 A2 | 11/2005 |
| WO | WO 2005/028663 A3 | 12/2005 |
| WO | WO 2005/098046 A3 | 12/2005 |
| WO | WO 2005/116264 A2 | 12/2005 |
| WO | WO 2005/118852 A2 | 12/2005 |
| WO | WO 2005/121362 A2 | 12/2005 |
| WO | WO 2005/085861 A3 | 2/2006 |
| WO | WO 2006/010610 A2 | 2/2006 |
| WO | WO 2005/118852 A3 | 3/2006 |
| WO | WO 2006/023563 A2 | 3/2006 |
| WO | WO 2005/121362 A3 | 4/2006 |
| WO | WO 2006/041453 A1 | 4/2006 |
| WO | WO 2006/043181 A2 | 4/2006 |
| WO | WO 2005/109238 A3 | 6/2006 |
| WO | WO 2006/010610 A3 | 6/2006 |
| WO | WO 2006/043181 A3 | 6/2006 |
| WO | WO 2006/076567 A2 | 7/2006 |
| WO | WO 2006/078470 A2 | 7/2006 |
| WO | WO 2005/043121 A3 | 8/2006 |
| WO | WO 2006/076567 A3 | 9/2006 |
| WO | WO 2006/078470 A3 | 9/2006 |
| WO | WO 2006/097049 A1 | 9/2006 |
| WO | WO 2006/100366 A2 | 9/2006 |
| WO | WO 2005/042713 A3 | 11/2006 |
| WO | WO 2006/023563 A3 | 11/2006 |
| WO | WO 2006/120434 A1 | 11/2006 |
| WO | WO 2005/084380 A3 | 12/2006 |
| WO | WO 2005/116264 A3 | 2/2007 |
| WO | WO 2007/020081 A1 | 2/2007 |
| WO | WO 2004/076643 A3 | 3/2007 |
| WO | WO 2007/024264 A2 | 3/2007 |
| WO | WO 2007/028146 A2 | 3/2007 |

(56) References Cited

FOREIGN PATENT DOCUMENTS

| WO | WO 2007/030949 A2 | 3/2007 |
|----|----|----|
| WO | WO 2007/033167 A2 | 3/2007 |
| WO | WO 2007/034221 A2 | 3/2007 |
| WO | WO 2007/035414 A2 | 3/2007 |
| WO | WO 2007/024264 A3 | 4/2007 |
| WO | WO 2007/036025 A1 | 4/2007 |
| WO | WO 2007/038264 A2 | 4/2007 |
| WO | WO 2007/041610 A2 | 4/2007 |
| WO | WO 2007/044091 A2 | 4/2007 |
| WO | WO 2007/044690 A2 | 4/2007 |
| WO | WO 2007/048076 A2 | 4/2007 |
| WO | WO 2007/030949 A3 | 5/2007 |
| WO | WO 2007/034221 A3 | 5/2007 |
| WO | WO 2007/050495 A2 | 5/2007 |
| WO | WO 2007/053142 A1 | 5/2007 |
| WO | WO 2007/053648 A2 | 5/2007 |
| WO | WO 2007/053785 A2 | 5/2007 |
| WO | WO 2007/059430 A2 | 5/2007 |
| WO | WO 2007/062222 A2 | 5/2007 |
| WO | WO 2005/058937 A3 | 6/2007 |
| WO | WO 2007/067734 A2 | 6/2007 |
| WO | WO 2007/048076 A3 | 7/2007 |
| WO | WO 2007/053648 A3 | 7/2007 |
| WO | WO 2007/075836 A2 | 7/2007 |
| WO | WO 2007/075879 A2 | 7/2007 |
| WO | WO 2007/076989 A1 | 7/2007 |
| WO | WO 2007/079229 A2 | 7/2007 |
| WO | WO 2007/079250 A2 | 7/2007 |
| WO | WO 2007/080583 A2 | 7/2007 |
| WO | WO 2007/082144 A2 | 7/2007 |
| WO | WO 2007/082154 A2 | 7/2007 |
| WO | WO 2007/082379 A2 | 7/2007 |
| WO | WO 2007/050495 A3 | 8/2007 |
| WO | WO 2007/075879 A3 | 8/2007 |
| WO | WO 2007/087612 A2 | 8/2007 |
| WO | WO 2007/089880 A2 | 8/2007 |
| WO | WO 2007/089911 A2 | 8/2007 |
| WO | WO 2007/090670 A1 | 8/2007 |
| WO | WO 2007/092473 A2 | 8/2007 |
| WO | WO 2007/092713 A2 | 8/2007 |
| WO | WO 2007/098484 A2 | 8/2007 |
| WO | WO 2006/100366 A3 | 9/2007 |
| WO | WO 2007/100684 A2 | 9/2007 |
| WO | WO 2007/100911 A2 | 9/2007 |
| WO | WO 2007/101609 A1 | 9/2007 |
| WO | WO 2007/103910 A2 | 9/2007 |
| WO | WO 2007/033167 A3 | 10/2007 |
| WO | WO 2007/038264 A3 | 10/2007 |
| WO | WO 2007/044690 A3 | 10/2007 |
| WO | WO 2007/053785 A3 | 10/2007 |
| WO | WO 2007/059430 A3 | 10/2007 |
| WO | WO 2005/084374 A3 | 11/2007 |
| WO | WO 2007/035414 A3 | 11/2007 |
| WO | WO 2007/044091 A3 | 11/2007 |
| WO | WO 2007/089880 A3 | 11/2007 |
| WO | WO 2007/100911 A3 | 11/2007 |
| WO | WO 2007/126938 A2 | 11/2007 |
| WO | WO 2007/132166 A2 | 11/2007 |
| WO | WO 2007/132167 A2 | 11/2007 |
| WO | WO 2007/082379 A3 | 12/2007 |
| WO | WO 2007/098484 A3 | 12/2007 |
| WO | WO 2007/147018 A2 | 12/2007 |
| WO | WO 2007/147073 A2 | 12/2007 |
| WO | WO 2007/147074 A2 | 12/2007 |
| WO | WO 2007/147076 A2 | 12/2007 |
| WO | WO 2007/147079 A2 | 12/2007 |
| WO | WO 2007/062222 A3 | 1/2008 |
| WO | WO 2007/100684 A3 | 1/2008 |
| WO | WO 2007/075836 A3 | 2/2008 |
| WO | WO 2007/132166 A3 | 2/2008 |
| WO | WO 2008/017871 A1 | 2/2008 |
| WO | WO 2008/045158 A1 | 4/2008 |
| WO | WO 2007/089911 A3 | 5/2008 |
| WO | WO 2007/132167 A3 | 5/2008 |
| WO | WO 2007/028146 A3 | 6/2008 |
| WO | WO 2007/067734 A3 | 8/2008 |
| WO | WO 2008/111990 A1 | 9/2008 |
| WO | WO 2007/126938 A3 | 10/2008 |
| WO | WO 2007/082154 A3 | 11/2008 |
| WO | WO 2007/087612 A3 | 11/2008 |
| WO | WO 2007/092473 A3 | 11/2008 |
| WO | WO 2007/082144 A3 | 12/2008 |
| WO | WO 2007/092713 A3 | 12/2008 |
| WO | WO 2007/079229 A3 | 1/2009 |
| WO | WO 2009/013492 A1 | 1/2009 |
| WO | WO 2009/013496 A1 | 1/2009 |
| WO | WO 2007/080583 A3 | 2/2009 |
| WO | WO 2009/019455 A2 | 2/2009 |
| WO | WO 2007/079250 A3 | 3/2009 |
| WO | WO 2007/041610 A3 | 4/2009 |
| WO | WO 2009/019455 A3 | 4/2009 |
| WO | WO 2010/045617 A2 | 4/2010 |
| WO | WO 2011/094646 A1 | 8/2011 |
| WO | WO 2011/102998 A2 | 8/2011 |

OTHER PUBLICATIONS

Iontorrent Application Note, pp. 1-6 (2016).*
Hua, R. et al., Prenatal Diagnosis, vol. 34, pp. 1-8 (2014).*
Breman, A.M. et al., Prenatal Diagnosis, vol. 36, pp. 1009-1019 (2016).*
Fiddler, M., J. Clin. Med., vol. 3, pp. 972-985 (2014).*
Hatt, L. et al., Prenatal Diagn., vol. 34, pp. 1-7 (2014).*
Christensen, B. et al., Fetal Diagn. Ther., vol. 18, pp. 479-484 (2003).*
Karow, J., "following Improvements in Noninvasive Fetal Cell Isolation, First Prenatal Tests Expected in 2016", published on genomeweb (www.genomeweb.com/archive/following-improvements-noninvasive-fetal-cell-isolation-first-prenatal-tests-expected-2016; pp. 1-4; (Nov. 2015).*
Wang, Y. et al., Mol. Cell, vol. 58, pp. 598-609 (2015).*
Bischoff, F.Z. et al., Clin. Genet., vol. 63, pp. 483-489 (2003).*
Geifman-Holtzman, O. et al., Am. J. Obstet. Gynecol., vol. 183, pp. 462-468 (2000).*
Vona, G. et al., Am. J. Pathol., vol. 160, pp. 51-58 (2002).*
Office action dated Jul. 29, 2014 for U.S. Appl. No. 13/835,926.
Office action dated Aug. 29, 2014 for U.S. Appl. No. 13/837,974.
Office action dated Sep. 17, 2014 for U.S. Appl. No. 13/863,992.
U.S. Appl. No. 60/764,420, filed Feb. 2, 2005, Quake.
U.S. Appl. No. 60/949,227, filed Jul. 11, 2007, Kapur.
U.S. Appl. No. 11/825,677, filed Jul. 5, 2007, Lopez et al.
U.S. Appl. No. 11/909,959, filed Sep. 27, 2007, Duff.
U.S. Appl. No. 13/794,503, filed Mar. 11, 2013, Stoughton et al.
717.305 pending claims dated Jan. 10, 2013 for U.S. Appl. No. 13/738,268.
Adams, et al. Complementary DNA Sequencing: Expressed Sequence Tags and Human Genome Project. Science Jun. 21, 1991: vol. 252 No. 5013 pp. 1651-1656 DOI: 10.1126/science.2047873.
Adinolfi, et al. Gene Amplification to Detect Fetal Nucleated Cells in Pregnant Women. The Lancet. Aug. 5, 1989:328-329.
Adinolfi, et al. Rapid detection of aneuploidies by microsatellite and the quantitative fluorescent polymerase chain reaction. Prenat. Diagn. 1997; 17(13):1299-311.
Adinolfi, M. On a Non-Invasive Approach to Prenatel Diagnosis based on the detection of Fetal Nucleated Cells in Maternal Blood Samples. Prenatal Diagnosis. 1991;11:799-804.
Advisory action dated Dec. 16, 2013 for U.S. Appl. No. 12/751,940.
Ahn, et al. A fully integrated micromachined magnetic particle separator. Journal of Microelectromechanical Systems. 1996; 5(3):151-158.
Allard, et al. Tumor cells circulate in the peripheral blood of all major carcinomas but not in healthy subjects or patients with nonmalignant diseases. Clin Cancer Res. Oct. 15, 2004;10(20):6897-904.
Allowed claims dated Dec. 9, 2010 for U.S. Appl. No. 11/701,686.
Amendments to the Claims Filed Mar. 29, 2013 with U.S. Patent Office for U.S. Appl. No. 12/751,940.
Amendments to the Claims. Filed Aug. 14, 2013 with U.S. Patent Office for U.S. Appl. No. 13/737,730.

(56) References Cited

OTHER PUBLICATIONS

Amendments to the Claims. Filed Jul. 11, 2013 with U.S. Patent Office for U.S. Appl. No. 13/831,342.
Amendments to the Claims. Filed Jul. 22, 2013 with U.S. Patent Office for U.S. Appl. No. 13/794,503.
Amendments to the Claims. Filed Jul. 25, 2013 with U.S. Patent Office for U.S. Appl. No. 13/829,971.
Amendments to the Claims. Filed Mar. 15, 2013 with U.S. Patent Office for U.S. Appl. No. 13/835,926.
Amendments to the Claims. Filed Mar. 15, 2013 with U.S. Patent Office for U.S. Appl. No. 13/837,974.
Amendments to the Claims. Filed Nov. 7, 2013 with U.S. Patent Office for U.S. Appl. No. 13/863,992.
Andrews, et al. Enrichment of fetal nucleated cells from maternal blood: model test system using cord blood. Prenatal Diagnosis. 1995; 15:913-919.
Applicant's Amendment and Response dated Jun. 17, 2009 to Non-Final Office Action dated Jan. 28, 2009 re U.S. Appl. No. 11/701,686.
Applicant's Amendment and Response dated Jun. 24, 2010 to Office Action dated Jan. 27, 2010 re U.S. Appl. No. 11/701,686.
Applicant's Amendment and Response dated Nov. 13, 2009 to Office Action dated Sep. 11, 2009 re U.S. Appl. No. 11/701,686.
Applicant's response dated Jun. 10, 2011 to Office action dated Apr. 25, 2011 for U.S. Appl. No. 12/393,803.
Ariga, et al. Kinetics of fetal cellular and cell-free DNA in the maternal circulation during and after pregnancy: implications for noninvasive prenatal diagnosis. Transfusion. 2001; 41:1524-1530.
Arnould, et al. Agreement between chromogenic in situ hybridisation (CISH) and FISH in the determination of HER2 status in breast cancer. Br J Cancer. 2003; 88(10):1587-91. (Abstract only).
Babochkina, et al. Direct detection of fetal cells in maternal blood: a reappraisal using a combination of two different Y chromosome-specific FISH probes and a single X chromosome-specific probe. Arch Gynecol Obstet. Dec. 2005;273(3):166-9. (Abstract only).
Babochkina, T. I. Ph. D. Dissertation—Fetal cells in maternal circulation: Fetal cell separation and FISH analysis. University of Basel, Switzerland. Dec. 8, 2005. (123 pages).
Balko, et al. Gene expression patterns that predict sensitivity to epidermal growth factor receptor tyrosine kinase inhibitors in lung cancer cell lines and human lung tumors. BMC Genomics. Nov. 10, 2006;7:289 (14 pages).
Barrett, et al. Comparative genomic hybridization using oligonucleotide microarrays and total genomic DNA. Proc Natl Acad Sci U S A. 2004; 101(51):17765-70.
Basch, et al. Cell separation using positive immunoselective techniques. Journal of Immunological Methods. 1983;56:269-280.
Bauer, J. Advances in cell separation: recent developments in counterflow centrifugal elutriation and continuous flow cell separation. Journal of Chromatography. 1999;722:55-69.
Becker, et al. Fabrication of Microstructures With High Aspect Ratios and Great Structural Heights by Synchrotron Radiation Lithography, Galvanoforming, and Plastic Moulding (LIGA Process). Microelectronic Engineering. 1986;4:35-56.
Becker, et al. Planar quartz chips with submicron channels for two-dimensional capillary electrophoresis applications. J. Micromech Microeng.1998;9:24-28.
Beebe et al. Functional Hydrogel Structures for Autonomous Flow Control Inside Microfluidic Channels. Nature. 2000; 404:588-590.
Bennett, et al. Toward the 1,000 dollars human genome. Pharmacogenomics. 2005; 6(4):373-82.
Berenson, et al. Cellular Immunoabsorption Using Monoclonal Antibodies. Transplantation.1984 ;38:136-143.
Berenson, et al. Positive selection of viable cell populations using avidin-biotin immunoadsorption. Journal of Immunological Methods. 1986;91:11-19.
Berg, H. C. Random Walks in Biology, Ch. 4. Princeton University Press. Princeton, NJ. 1993. pp. 48-64.
Berger, et al. Design of a microfabricated magnetic cell separator. Electrophoresis. Oct. 2001;22(18):3883-92.

Bianchi, et al. Isolation of fetal DNA from nucleated erythrocytes in maternal blood. Medical Sciences. 1990;87:3279-3283.
Bianchi, et al. Demonstration of fetal gene sequences in nucleated erythrocytes isolated from maternal blood. American Journal of Human Genetics. 1989;45:A252.
Bianchi, et al. Fetal gender and aneuploidy detection using fetal cells in maternal blood: analysis of NIFTY I data. Prenatal Diagnosis. 2002; 22:609-615.
Bianchi, et al. Fetal nucleated erythrocytes (FNRBC) in maternal blood: erythroid-specific antibodies improve detection. The American Journal of Human Genetics. Oct. 1992. Supplemental to vol. 51, No. 4: 996.
Bianchi, et al. Isolation of Male Fetal DNA from Nucleated Erythrocytes (NRBC) in Maternal Blood. The American Pediatric Society and Society for Pediatric Research, (1989) Mar. 1989; 818:139A.
Bianchi, et al. Possible Effects of Gestational Age on the Detection of Fetal Nucleated Erythrocytes in Maternal Blood. Prenatal Diagnosis. 1991;11:523-528.
Bignell, et al. High-resolution analysis of DNA copy number using oligonucleotide microarrays. Genome Research. 2004; 14(2):287-295.
Binladen, et al. The Use of Coded PCR Primers Enables High-Throughput Sequencing of Multiple Homolog Amplification Products by 454 Parallel Sequencing. Feb. 2007, PLoS One. 2(2):e197, doi:10.1371/journal.pone.0000197.
Blake, et al. Assessment of multiplex fluorescent PCR for screening single cells for trisomy 21 and single gene defects. Mol. Hum. Reprod. 1999; 5(12):1166-75.
Bode, et al. Mutations in the tyrosine kinase domain of the EGFR gene are rare in synovial sarcoma. Mod Pathol. Apr. 2006;19(4):541-7.
Boehm, et al. Analysis of Defective Dystrophin Genes with cDNA Probes: Rearrangement Polymorphism, Detection of Deletions in Carrier Females, and Lower Than Expected Frequency of Carrier Mothers in Isolated Cases of Delections. Pediatric Research. Apr. 1989: 139A-820.
Bohmer, et al. Differential Development of Fetal and Adult Haemoglobin Profiles in Colony Culture: Isolation of Fetal Nucleated Red Cells by Two-Colour Fluorescence Labelling. Br. J. Haematol. 1998; 103:351-60.
Bookout, et al. High-throughput real-time quantifative reverse transcription PCR. Curr. Prot. Mol. Biol. 2005; 15.8.1-15.8.21.
Braslavsky, et al. "Sequence information can be obtained from single DNA molecules," PNAS, Apr. 2003, vol. 100, No. 7, 3960-3964.
Brison, et al. General Method for Cloning Amplified DNA by Differential Screening with Genomic Probes. Molecular and Cellular Biology. 1982;2:578-587.
Brody, et al. Deformation and Flow of Red Blood Cells in a Synthetic Lattice: Evidence for an Active Cytoskeleton. Biophys. J. 68:2224-2232 (1995).
Brown, et al. Applicant-Initiated Interview Summary, with Office Action Summary, and Information Disclosure Statement by Applicant. dated Sep. 16, 2009.
Bustamante-Aragones, et al. Detection of a Paternally Inherited Fetal Mutation in Maternal Plasma by the Use of Automated Sequencing. Ann. N.Y. Acad. Sci. 1075: 108-117 (2006), pp. 108-117, XP-002652985.
Caggana, M. Microfabricated devices for sparse cell isolation. CNF Project #905-00. Cornell NanoScale Facility. 2003; pp. 38-39.
Caggana, M. Microfabricated devices for sparse cell isolation. CNF Project #905-00. Cornell NanoScale Facility. 2004-2005; pp. 32-33.
Calin, et al. A microRNA signature Associated with prognosis and progression in chronic lymphocytic leukemia. New England Journal of Medicine. 2005; 353:1793-1801.
Cappuzzo, et al. Epidermal growth factor receptor gene and protein and gefitinib sensitivity in non-small-cell lung cancer. J Natl Cancer Inst. May 4, 2005;97(9):643-55.
Cha, The utility of an erythroblast scoring system and gender-independent short tandem repeat (STR) analysis for the detection of aneuploid fetal cells in maternal blood. Prenat. Diagn. 2005; 25(7):586-91.

(56) References Cited

OTHER PUBLICATIONS

Chamberlain, et al. Deletion screening of the Duchenne muscular dystrophy locus via multiplex DNA amplification. Nucleic Acids Research. 1988;16:11141-11156.

Chan, et al. "DNA Mapping Using Microfluidic Stretching and Single-Molecule Detection of Fluorescent Site-Specific Tags," Genome Research, 2004, vol. 14, 1137-1146.

Chan, et al. Size distributions of maternal and fetal DNA in maternal plasma. Clin Chem. Jan. 2004;50(1):88-92.

Chang, et al. Biomimetic technique for adhesion-based collection and separation of cells in a microfluidic channel. Lab Chip. 2005; 5:64-73.

Cheung, et al. Development and validation of a CGH microarray for clinical cytogenetic diagnosis. Genet Med. 2005; 7(6):422-32.

Chiu, et al. "Effects of Blood-Processing Protocols on Fetal and Total DNA Quantification in Maternal Plasma," Clinical Chemistry, 2001, vol. 47, No. 9, 1607-1613.

Chiu, et al. Non-invasive prenatal assessment of trisomy 21 by multiplexed maternal plasma DNA sequencing: large scale validity study. BMJ. Jan. 11, 2011;342:c7401. doi: 10.1136/bmj.c7401.

Chiu, et al. Non-invasive prenatal diagnosis by single molecule counting technologies. Trends in Genetics, vol. 25, Issue 7, Jul. 2009, pp. 324-331.

Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.

Chiu, et al. Patterned Deposition of Cells and Proteins Onto Surfaces by Using Three-Dimensional Microfluidic Systems. Proceedings of the National Academy of Sciences of the United States of America. 2000; pp. 2408-2413.

Choesmel, et al. Enrichment methods to detect bone marrow micrometastases in breast carcinoma patients: clinical relevance. Breast Cancer Res. 2004;6(5):R556-569.

Choolani, et al. Characterization of First Trimester Fetal Erythroblasts for Non-Invasive Prenatal Diagnosis. Mol. Hum. Reprod. 2003; 9:227-35.

Chou, et al. A Microfabricated Device for Sizing and Sorting DNA Molecules. Proceedings of the National Academy of Sciences of the United States of America. 1999; pp. 11-13.

Chou, et al. Sorting by diffusion: An asymmetric obstacle course for continuous molecular separation. PNAS. 1999; 96(24):13762-13765.

Christel, et al. High aspect ratio silicon microstructures for nucleic acid extraction. Solid-state sensor and actuator workshop. Hilton Head, SC. Jun. 8-11, 1998; 363-366.

Christensen, et al. Fetal Cells in Maternal Blood: A Comparison of Methods for Cell Isolation and Identification. Fetal Diagn. Ther. 2005; 20:106-12.

Chueh, et al. Prenatal Diagnosis Using Fetal Cells from the Maternal Circulation. West J. Med. 159:308-311 (1993).

Chueh, et al. Prenatal Diagnosis Using Fetal Cells in the Maternal Circulation. Seminars in Perinatology. 1990;14:471-482.

Chueh, et al. The search for fetal cells in the maternal circulation. J Perinat Med. 1991;19:411-420.

Cirigliano, et al. "Clinical application of multiplex quantitative fluorescent polymerase chain reaction (QF-PCR) for the rapid prenatal detection of common chromosome aneuploidies," Molecular Human Reproduction, 2001, vol. 7, No. 10, 1001-1006.

Claims mailed with RCE Response to Final Rejection dated Dec. 31, 2009 for U.S. Appl. No. 11/763,421, filed Jun. 14, 2007 (6 pages).

Claims. Filed Nov. 29, 2011 with U.S. Patent Office for U.S. Appl. No. 13/306,520.

Claims. Filed Nov. 29, 2011 with U.S. Patent Office for U.S. Appl. No. 13/306,640.

Claims. Filed Nov. 29, 2011 with U.S. Patent Office for U.S. Appl. No. 13/306,698.

Clayton, et al. Fetal Erythrocytes in the Maternal Circulation of Pregnant Women. Obstetrics and Gynecology. 1964;23:915-919.

Collarini, et al. Comparison of methods for erythroblast selection: application to selecting fetal erythroblasts from maternal blood. Cytometry. 2001; 45:267-276.

Cotton, et al. Reactivity of cytosine and thymine in single-base-pair mismatches with hydroxylamine and osmium tetroxide and its application to the study of mutations. Proc Natl Acad Sci U S A. Jun. 1988;85(12):4397-401.

Craig, et al. Identification of genetic variants using bar-coded multiplexed sequencing. Nat Methods. Oct. 2008 ; 5(10): 887-893. DOI:10.1038/nmeth.1251.

Cremer, et al. Detection of chromosome aberrations in human interphase nucleus by visualization of specific target DNAs with radioactive and non-radioactive in situ hybridization techniques: diagnosis of trisomy 18 with probe L1.84. Human Genetics. 1986;74:346-352.

Cremer, et al. Detection of chromosome aberaations in metaphase and interphase tumor cells by in situ hybridization using chromosome-specific library probes. Human Genetics.1988;80:235-246.

Cristofanilli, et al. Circulating tumor cells revisited. JAMA. 2010; 303(11):1092-1093.

Cristofanilli, et al. Circulating tumor cells, disease progression, and survival in metastatic breast cancer. N Engl J Med. Aug. 19, 2004;351(8):781-91.

Das, et al. Dielectrophoretic segregation of different human cell types on microscope slides. Anal. Chem. 2005; 77:2708-2719.

De Alba, et al. Prenatal diagnosis on fetal cells obtained from maternal peripheral blood: report of 66 cases. Prenat Diagn. Oct. 1999;19(10):934-40.

De Kretser, et al. The Separation of Cell Populations using Monoclonal Antibodies attached to Sepharose. Tissue Antigens. 1980;16:317-325.

De Luca, et al. Detection of circulating tumor cells in carcinoma patients by a novel epidermal growth factor receptor reverse transcription—PCR assay. Clin Cancer Res. Apr. 2000;6(4):1439-44.

Decision re: Institution of Inter Partes Review 37 C.F.R. § 42.108. Entered Oct. 25, 2013. For Case IPR2013-00277. U.S. Pat. No. 8,318,430.

Decision: Institution of Inter Partes Review 37 C.F.R. § 42.108. Dated . Entered Oct. 25, 2013. For Case IPR2013-00276. U.S. Pat. No. 8,318,430 B2.

Declaration of Cynthia Casson Morton. Dated May 29, 2013. U.S. Pat. No. 8,296,076.

Declaration of Cynthia Casson Morton. Dated May 10, 2013. In re: Chuu, et al., U.S. Pat. No. 8,318,430.

Declaration of Cynthia Casson Morton. Dated May 10, 2013. In re: Chuu, et al., U.S. Pat. No. 8,318,430, claims 1-18.

Declaration of Robert Nussbaum. Dated May 22, 2013. U.S. Pat. No. 8,296,076.

Declaration of Robert Nussbaum. Dated May 8, 2013. In re Patent of: Chuu, et al. U.S. Pat. No. 8,318,430.

Declaration of Robert Nussbaum. Dated Apr. 16, 2013. In re Patent of: Fan, et al. U.S. Pat. No. 8,318,430, claims 1-18.

Delamarche, et al. Microfluidic Networks for Chemical Patterning of Substrates: Design and Application to Bioassays. Journal of the American Chemical Society. 1998; 120:500-508.

Delamarche, et al. Patterned Delivery of Immunoglobulins to Surfaces Using Microfluidic Networks. Science. 1997; 276:779-781.

Deng, et al. Enumeration and microfluidic chip separation of circulating fetal cells early in pregnancy from maternal blood. American Journal of Obstetrics & Gynecology. Dec. 2008 (vol. 199, Issue 6, p. S134).

Deshmukh, et al. Continuous Micromixer With Pulsatile Micropumps. Solid-State Sensor and Actuator Workshop. Hilton Head Island, South Carolina; Jun. 4-8, 2000:73-76.

Devotek. "Separation of RNA 8 DNA by Gel Filtration Chromatography," Edvotek, 1987. 1-9.

Dhallan, et al. A non-invasive test for prenatal diagnosis based on fetal DNA present in maternal blood: a preliminary study. The Lancet, vol. 369, Issue 9560, Feb. 10, 2007, pp. 440-442.

Di Naro, et al. Prenatal diagnosis of beta-thalassaemia using fetal erythroblasts enriched from maternal blood by a novel gradient. Mol Hum Reprod. 2000; 6(6):571-4.

(56) References Cited

OTHER PUBLICATIONS

Diehl, et al. Digital quantification of mutant DNA in cancer patients. Curr Opin Oncol. Jan. 2007;19(1):36-42.
Dilella, et al. Screening for Phenylketonuria Mutations by DNA Amplification with the Polymerase Chain Reaction. The Lancet. Mar. 5, 1988:497-499.
Dohm, et al. Substantial biases in ultra-short read data sets from high-throughput DNA sequencing. Nucleic Acids Research. 2008. 36: e105 doi: 10.1093\nark\gkn425.
Doyle, et al. Self-Assembled Magnetic Matrices for DNA Separation Chips. Science 295:2237 (2002).
Dragovich, et al. Anti-EGFR-targeted therapy for exophageal and gastric cancers: an evolving concept. Jornal of Oncology. 2009; vol. 2009, Article ID 804108.
Dressman, et al. "Transforming single DNA molecules into fluorescent magnetic particles for detection and enumeration of genetic variations." PNAS, Jul. 2003, vol. 100. No. 15, 8817-8822.
Drmanac, et al. DNA Sequence Determination by Hybridization: A Strategy for Efficient Large-Scale Sequencing. Science Jun. 11, 1993: vol. 260 No. 5114 pp. 1649-1652 DOI: 10.1126/science. 8503011. Jun. 11, 1993.
Eigen, et al. Sorting Single Molecules: Application to Diagnostics and Evolutionary Biotechnology. Proceedings of the National Academy of Sciences of the United States of America. 1994; 91:5740-5747.
Emanuel, et al. Amplification of Specific Gene Products from Human Serum. GATA, 1993, vol. 10, No. 6, 144-146.
European office action dated Jun. 26, 2012 for EP Application No. 11159371.1.
European office action dated Jul. 17, 2013 for EP Application No. 11159371.1, 8 pages.
European office action dated Oct. 8, 2012 for EP Application No. 11175845.
European office action dated Dec. 13, 2013 for EP Application No. 11159371.1.
European office action dated Dec. 16, 2013 for EP Application No. 12175907.
European office action dated Dec. 18, 2012 for EP Application No. 11159371.1.
European Search Opinion dated Jul. 31, 2009 for EP07763674.4.
European Search Report Office action dated Dec. 21, 2010 for EP07763674.4.
European search report and search opinion dated Jan. 2, 2013 for EP Application No. 12175907.0.
European search report and search opinion dated Mar. 16, 2012 for EP Application No. 11182181.
European search report and search opinion dated Apr. 9, 2013 for EP Application No. 12180149.2.
European search report and search opinion dated Nov. 17, 2011 for EP Application No. 11175845.
European Search Report dated Jul. 31, 2009 for EP07763674.4.
European search report dated Nov. 9, 2009 for Application No. 7784442.1.
European search report dated Dec. 21, 2009 for Application No. 07798579.4.
European search report dated Dec. 22, 2009 for Application No. 07798580.2.
European search report dated Dec. 22, 2009 for Application No. 07784444.7.
Applicant's Response with Allowed Claims dated Dec. 2, 2010 issued in U.S. Appl. No. 11/701,686.
Pending Claims filed with the USPTO on Jun. 24, 2010 for U.S. Appl. No. 11/701,686.
Extended European Search Report for Application No. 11159371 dated Aug. 10, 2011, 10 pages.
Falcidia, et al. Fetal Cells in maternal blood: a six-fold increase in women who have undergone mniocentesis and carry a fetus with Down syndrome: a multicenter study. Neuropediatrics. 2004; 35(6):321-324. (Abstract only).
Fan, et al. Detection of aneuploidy with digital polymerase chain reaction. Anal Chem. Oct. 1, 2007; 79(19):7576-9.
Fan, et al. Highly parallel SNP genotyping. Cold Spring Harb. Symp. Quant. Biol. 2003; 68:69-78.
Fan, et al. Microfluidic digital PCR enables rapid prenatal diagnosis of fetal aneuploidy. Am J Obstet Gynecol. May 2009;200(5):543. e1-7.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Single cell degenerate oligonucleotide primer-PCR and comparative genomic hybridization with modified control reference. Journal of Ahejian University—Science A. 2001; 2(3):318-321.
Farber, et al. Demonstration of spontaneous XX/XY chimerism by DNA fingerprinting. Human Genetics. 1989;82:197-198.
Farooqui, et al. Microfabrication of Submicron Nozzles in Silicon Nitride. Journal of Microelectromechanical Systems. 1992; 1(2):86-88.
Feinberg, et al. A technique for radiolabeling DNA restriction endonuclease fragments to high specific activity. Anal Biochem. Jul. 1, 1983;132(1):6-13.
Fiedler, et al. Dielectrophoretic Sorting of Particles and Cells in a Microsystem. Analytical Chemistry. 1998; pp. 1909-1915.
Findlay, et al. Using MF-PCR to diagnose multiple defects from single cells: implications for PGD. Mol Cell Endocrinol. 2001; 183 Suppl 1:S5-12.
Fleischmann, et al. Whole-Genome Random Sequencing and Assembly of Haemophilus influenzae Rd. Science Jul. 28, 1995: vol. 269 No. 5223 pp. 496-512 DOI: 10.1126/science.7542800.
Freemantle, M. Downsizing Chemistry. Chemical analysis and synthesis on microchips promise a variety of potential benefits. Chemical & Engineering News. 1999; pp. 27-36.
Fu, et al. An integrated miscrofabricated cell sorter. Anal Chem. 2002;74:2451-2457.
Fu, et al. A Microfabricated Fluorescence-Activated Cell Sorter. Nature Biotechnology.1999; 17:1109-1111.
Fuhr, et al. Biological Application of Microstructures. Topics in Current Chemistry. 1997; 194:83-116.
Fullwood, et al. Next Generation DNA sequencin of paired-end tags (PET) for transcriptome and genome analyses. Genome Research. 2009. 19:521-532.
Furdui, et al. Immunomagnetic T cell capture from blood for PCR analysis using microfluidic systems. Lab Chip. Dec. 2004;4(6):614-8.
Ganshirt-Ahlert, et al. Magnetic cell sorting and the transferrin receptor as potential means of prenatal diagnosis from maternal blood. Am J Obstet Gynecol. 1992;166:1350-1355.
Ganshirt-Ahlert, et al. Noninvasive prenatal diagnosis: Triple density gradient, magnetic activated cell sorting and FISH prove to be an efficient and reproducible method for detection of fetal aneuploidies from maternal blood. The American Journal of Human Genetics. Oct. 1992. Supplemental to vol. 51, No. 4: 182.
Gardella, et al. Second Petition for Inter Partes Review Under 35 U.S.C. §§ 311-319 and 37 C.F.R. § 42.100 ET SEQ.(Claims 19-30). Dated May 10, 2013, for U.S. Pat. No. 8,318,430.
Gardella, G. First Petition for Inter Partes Review Under 35 U.S.C. §§ 311-319 and 37 C.F.R. § 42.100 ET SEQ. (Claims 1-18). Dated May 10, 2013. U.S. Pat. No. 8,318,430.
Gardella, G. Petition for Inter Partes Review Under 35 U.S.C. §§ 311-319 and 37 C.F.R. § 42.100 ET SEQ. Dated May 24, 2013. U.S. Pat. No. 8,296,076.
GenomeWeb. Immunicon inks biomarker assay, lab services deal with merck serona. Available at C:\Documents and Settings\fc3\Local Settings\Temporary Internet Files\OLK35E\141896-1.htm. Accessed on Sep. 11, 2007.
Ghia, et al. Ordering of human bone marrow B lymphocyte precursors by single-cell polymerase chain reaction analyses of the rearrangement status of the immunoglobulin H and L chain gene loci. J Exp Med. Dec. 1, 1996;184(6):2217-29.
Giddings, J. C. Chemistry 'Eddy' Diffusion in Chromatography. Nature. 1959;184:357-358.

(56) References Cited

OTHER PUBLICATIONS

Giddings, J. C. Field-Flow Fractionation: Analysis of Macromolecular, Colloidal, and Particulate Materials. Science. 1993;260:1456-1465.
Gonzalez, et al. Multiple displacement amplification as a pre-polymerase chain reaction (pre-PCR) to process difficult to amplify samples and low copy number sequences from natural environments. Environ Microbiol. 2005; 7(7):1024-8.
Graham. Efficiency comparison of two preparative mechanisms for magnetic separation of erthrocytes from whole blood. J. Appl. Phys. 1981; 52:2578-2580.
Greaves, et al. Expression of the OKT Monoclonal Antibody Defined Antigenic Determinants in Malignancy. Int. J. Immunopharmac. 1981;3:283-299.
Guetta, et al. Analysis of fetal blood cells in the maternal circulation: challenges, ongoing efforts, and potential solutions. Stem Cells Dev. 2004;13(1):93-9.
Gunderson, et al. A genome-wide scalable SNP genotyping assay using microarray technology. Nat Genet. 2005; 37(5):549-54.
Hahn, et al. "Prenatal Diagnosis Using Fetal Cells and Cell-Free Fetal DNA in Maternal Blood: What is Currently Feasible?" Clinical Obstetrics and Gynecology, Sep. 2002, vol. 45, No. 3, 649-656.
Hahn, et al. Current applications of single-cell PCR. Cell. Mol. Life Sci. 2000; 57(1):96-105. Review.
Hahn, et al. Micro system for isolation of fetal DNA from maternal plasma by preparative size separation. Clin Chem. Dec. 2009;55(12):2144-52. doi: 10.1373/clinchem.2009.127480. Epub Oct. 1, 2009.
Hamabe, et al. Molecular study of the Prader-Willi syndrome: deletion, RFLP, and phenotype analyses of 50 patients. Am J Med Genet. Oct. 1, 1991;41(1):54-63.
Han, et al. Separation of Long DNA Molecules in a Microfabricated Entropic Trap Array. Science. 2000;288:1026-1029.
Hardenbol, et al. Highly multiplexed molecular inversion probe genotyping: over 10,000 targeted SNPs genotyped in a single tube assay. Genome Res. 2005;15(2):269-75.
Hardenbol, et al. Multiplexed genotyping with sequence-tagged molecular inversion probes. Nat. Biotechnol. 2003; 21(6):673-8.
Harris, et al. Single-molecule DNA sequencing of a viral genome. Science. Apr. 4, 2008;320(5872):106-9.
Hartmann, et al. Gene expression profiling of single cells on large-scale oligonucleotide arrays. Nucleic Acids Research. 2006; 34(21): e143. (11 pages).
Herzenberg, et al. Fetal cells in the blood of pregnant women: Detection and enrichment by flourescence-activated cell sorting. Proc. Natl. Acad. Sci. 1979;76:1453-1455.
Holt, et al. The new paradigm of flow cell sequencing. DOI: 10.1101/gr.073262.107 Genome Res. 2008. 18: 839-846.
Holzgreve, et al. Fetal Cells in the Maternal Circulation. Journal of Reproductive Medicine. 1992;37:410-418.
Hong, et al. A nanoliter-scale nucleic acid processor with parallel architecture. Nat. Biotechnol. 2004; 22(4):435-9.
Hong, et al. Molecular biology on a microfluidic chip. Journal of Physics: Condensed Matter, 2006, vol. 18, S691-S701.
Hosono, et al. Unbiased whole-genome amplification directly from clinical samples. Genome Res. May 2003;13(5):954-64.
Hromadnikova, et al. "Quantitative analysis of DNA levels in maternal plasma in normal and Down syndrome pregnancies." Bio Med Central, May 2002, 1-5.
Huang, et al. A DNA prism for high-speed continuous fractionation of large DNA molecules. Nature Biotechnology. 2002;20:1048-1051.
Huang, et al. Continuous Particle Separation Through Deterministic Lateral Displacement. Science 304:987-90 (2004).
Huang, et al. Electric Manipulation of Bioparticles and Macromoledules on Microfabricated Electrodes. Analytical Chemistry. 2001; pp. 1549-1559.
Huang, et al. Role of Molecular Size in Ratchet Fractionation. 2002; 89(17):178301-1-178301-4.
Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.
Hviid T. In-Cell PCT method for specific genotyping of genomic DNA from one individual in a micture of cells from two individuals: a model study with specific relevance to prenatal diagnosis based on fetal cells in maternal blood. Molecular Diagnostics and Genetics. 2002; 48:2115-2123.
Hviid, T. In-cell polymerase chain reaction: strategy and diagnostic applications. Methods Mol Biol. 2006;336:45-58.
International preliminary report on patentability dated Oct. 29, 2008 for PCT/US2007/003209.
International search report and written opinion dated Mar. 16, 2010 for PCT Application No. US2009/57136.
International Search Report and Written Opinion dated Sep. 18, 2008 for PCT/US2007/003209.
International search report dated Jan. 16, 2008 for PCT Application No. US2007/71247.
International search report dated Jan. 25, 2008 for PCT Application No. US2007/71250.
International search report dated Nov. 15, 2007 for PCT Application No. US2007/71149.
International search report dated Nov. 26, 2007 for PCT Application No. US2007/71256.
International search report dated Feb. 25, 2008 for PCT Application No. US07/71148.
International search report dated Feb. 25, 2008 for PCT Application No. US2007/71248.
Ishikawa, et al. Allelic dosage analysis with genotyping microarrays. Biochem Biophys Res Commun. Aug. 12, 2005;333(4):1309-14.
Iverson, et al. Detection and Isolation of Fetal Cells From Maternal Blood Using the Flourescence-Activated Cell Sorter (FACS). Prenatal Diagnosis 1981;1:61-73.
Jan, et al. Fetal Erythrocytes Detected and Separated from Maternal Blood by Electronic Fluorescent Cell Sorter. Texas Rep Biol Med. 1973;31:575.
Jeon, et al. Generation of Solution and surface Gradients Using Microfluidic Systems. Langmuir. 2000, pp. 8311-8316.
Jiang, et al. Genome amplification of single sperm using multiple displacement amplification. Nucleic Acids Res. 2005; 33(10):e91. (9 pages).
Jiang, et al. Old can be new again: HAPPY whole genome sequencing, mapping and assembly. Int J Biol Sci. 2009;5(4):298-303. Epub Apr. 15, 2009.
Joint Claim Construction and Prehearing Statement. Case: 12-cv-05501-SI; Dated May 3, 2013.
Kamholz, et al. Quantitative Analysis of Molecular Interaction in a Microfluidic Channel: the T-Sensor. Analytical Chemistry. 1999; pp. 5340-5347.
Kan, et al. Concentration of Fetal Red Blood Cells From a Mixture of Maternal and Fetal Blood by Anti-i Serum—An Aid to Prenatal Diagnosis of Hemoglobinopathies. Blood. 1974; 43:411-415.
Kartalov et al.: "Microfluidic device reads up to four consecutive base pairs in DNA sequencing-by-synthesis.", Nucleic Acids Research, 2004, vol. 32, No. 9, 2004, pp. 2873-2879, XP-002652987.
Kasakov, et al. Extracellular DNA in the blood of pregnant women. Tsitologiia. 1995;37(3):232-6. (English translation only).
Kazakov, et al. Extracellular DNA in the blood of pregnant women Tsitologiia. 1995; 37(3): 232-6.
Kenis, et al. Microfabrication Inside Capillaries Using Multiphase Laminar Flow Patterning. Science. 1999; 285:83-85.
Kim, et al. Polymer microstructures formed by moulding in capillaries. Nature. 1995;376:581-584.
Kimura, et al. Deletional mutant EGFR detected in circulating tumor-derived DNA from lung cancer patients treated with gefitinib. American Association for Cancer Research 96th Annual Meeting. Apr. 16-20, 2005. Abstract 479.
Kimura, et al. The DYRK1A gene, encoded in chromosome 21 Down syndrome critical region, bridges between (β-amyloid production and tau phosphorylation in Alzheimer disease. Human Molecular Genetics, Nov. 29, 2008, vol. 16, No. 1, 15-23.

(56) References Cited

OTHER PUBLICATIONS

Klein, C. A. Single cell amplification methods for the study of cancer and cellular ageing. Mech. Ageing Dev. 2005; 126(1):147-51.
Klein, et al. Comparative genomic hybridization, loss of heterozygosity, and DNA sequence analysis of single cells. Proc Natl Acad Sci U S A. 1999; 96(8):4494-9.
Kobayashi, et al. EGFR mutation and resistance of non-small-cell lung cancer to gefitinib. N Engl J Med. Feb. 24, 2005;352(8):786-92.
Kogan, et al. An Improved Method for Prenatal Diagnosis of Genetic Diseases by Analysis of Amplified DNA Sequences, Application to Hemophilia A. The New England Journal of Medicine. 1987;317:985-990.
Korenberg, et al. Down syndrome phenotypes: the consequences of chromosomal imbalance. PNAS 1994; 91:4997-5001.
Krabchi, et al. Quantification of all fetal nucleated cells in maternal blood between the 18th and 22nd weeks of pregnancy using molecular cytogenic techniques. Clin. Genet. 2001; 60:145-150.
Krivacic, et al. A rare-cell detector for cancer. PNAS. 2004;101:10501-10504.
Kulozik, et al. Fetal Cell in the Maternal Circulation: Detection by Direct AFP-Immunoflourescence. Human Genetics. 1982;62:221-224.
Kurg, et al. Arrayed primer extension: solid-phase four-color DNA resequencing and mutation detection technology. Genet Test. 2000;4(1):1-7.
Lander, et al. Initial sequencing and analysis of the human genome. Nature 409, 860-921 (Feb. 15, 2001) | DOI:10.1038/35057062; Accepted Jan. 9, 2001.
Leutwyler, K. Mapping Chromosome 21. Available at http://www.scientificamerican.com/article.cfm?id=mapping-chromosome-21. Accessed Feb. 3, 2010.
Levett, et al. A large-scale evaluation of amnio-PCR for the rapid prenatal diagnosis of fetal trisomy. Ultrasound Obstet Gynecol. 2001; 17(2):115-8.
Li , et al. Transport, Manipulation, and Reaction of Biological Cells On-Chip Using Electrokinetic Effects. Analytical Chemistry., 1997; pp. 1564-1568.
Li, et al. Amplification and analysis of DNA sequences in single human sperm and diploid cells. Nature. 1988;335:414-417.
Li, et al. Size separation of circulatory Dna in maternal plasma permits ready detection of fetal DNA polymorphisms. Clin Chem. Jun. 2004;50(6):1002-11.
Li, et. al. Mapping short DNA sequencing reads and calling variants using mapping quality scores. Genome Res. Nov. 2008;18(11):1851-8. doi: 10.1101/gr.078212.108. Epub Aug. 19, 2008.
Lichter , et al. Delineation of individual human chromosomes in metaphase and interphase cells by in situ suppression hyridization using recombinant DNA libraries. Hum Genet. 1988;80:224-234.
Lieberfarb, et al. Genome-wide loss of heterozygosity analysis from laser capture microdissected prostate cancer using single nucleotide polymorphic allele (SNP) arrays and a novel bioinformatics platform dChipSNP. Cancer Res. Aug. 15, 2003;63(16):4781-5.
Liu, et al. Development and validation of a T7 based linear amplification for genomic DNA. BMC Genomics. 2003; 4(1):19. (11 pages).
Lo, et al. Detection of fetal RhD sequence from peripheral blood of sensitized RhD-negative pregnant women. British Journalof Haematology, 1994, vol. 87, 658-660.
Lo, et al. Detection of single-copy fetal DNA sequence from maternal blood. The Lancet, Jun. 16, 1990, vol. 335, 1463-1464.
Lo, et al. Digital PCR for the molecular detection of fetal chromosomal aneuploidy. PNAS. Aug. 7, 2007; 104(32):13116-13121.
Lo, et al. Fetal DNA in Maternal Plasma. Ann. N. Y. Acad. Sci, Apr. 2000, vol. 906, 141-147.
Lo, et al. Plasma placental RNA allelic ratio permits noninvasive prenatal chromosomal aneuploidy detection. Nat Med. Feb, 2007;13(2):218-23.
Lo, et al. Prenatal diagnosis of fetal RhD status by molecular analysis of maternal plasma. N Engl J Med 1998; 339:1734-1738 Dec. 10, 1998 DOI: 10.1056/NEJM199812103392402.
Lo, et al. Prenatal diagnosis: progress through plasma nucleic acids. Nature. Jan. 2007, vol. 8, 71-76.
Lo, et al. Prenatal sex determination by DNA amplification from material peripheral blood. The Lancet.Dec. 9, 1989:1363-1365.
Lo, et al. Presence of fetal DNA in maternal plasma and serum. The Lancet, Aug. 16, 1997, vol. 350, 485-487.
Lo, et al. Quantitative Analysis of Fetal NA in Maternal Plasma and Serum: Implications for Noninvasive Prenatal Diagnosis. Am J. Hum. Genet., 1998, vol. 62, 768-775.
Lo, Y. M. Noninvasive prenatal detection of fetal chromosomal aneuploidies by maternal plasma nucleic acid analysis: a review of the current state of the art. BJOG, 2009, vol. 116, 152-157.
Loken , et al. Flow Cytometric Analysis of Human Bone Marrow: I. Normal Erythroid Development. Blood. 1987;69:255-263.
Lun, et al. Microfluidics Digital PCR Reveals a Higher than Expected Fraction of Fetal DNA in Maternal Plasma. Clinical Chemistry, 2008, vol. 54, No. 10, 1664-1672.
Mahr, et al. Fluorescence in situ hybridization of fetal nucleated red blood cells. The American Journal of Human Genetics. Oct. 1992. Supplemental to vol. 51, No. 4: 1621.
Maloney et al. "Microchimerism of maternal origin persists into adult life," J. Clin. Invest. 104:41-47 (1999).
Marcus, et al. Microfluidic Single-Cell mRNA Isolation and Analysis. American Chemical Society, Mar. 2006; 76:3084-3089.
Marcus, et al. Parallel Picoliter RT-PCR Assays Using Microfluidics. Analytical Chemistry, Feb. 1, 2006, vol. 78, No. 3, 956-958.
Margulies, et al. Genome sequencing in microfabricated high-density picolitre reactors. Nature. 2005; 437:376-80.
Marks, et al. Epidermal growth factor receptor (EGFR) expression in prostatic adenocarcinoma after hormonal therapy: a fluorescence in situ hybridization and immunohistochemical analysis. The Prostate. 2008; 68:919-923.
Martin, et al. "A method for using serum or plasma as a source of NDA for HLA typing," Human Immunology. 1992; 33:108-113.
Martin, New technologies for large-genome sequencing. Genome, 1989, vol. 31, No. 2 : pp. 1073-1080 DOI: 10.1139/g89-184.
Mavrou, et al. Identification of nucleated red blood cells in maternal circulation: A second step in screening for fetal aneuploidies and pregnancy complications. Prenat Diagn. 2007; 247:150-153.
McCabe, et al. DNA microextraction from dried blood spots on filter paper blotters: potential applications to newborn screening. Hum Genet.1987;75:213-216.
McCarley, et al. Patterning of surface-capture architectures in polymer-based microanalytical devices. In Kutter, et al. Eds. Royal Society of Chemistry Special Publication. 2005;130-132. (Abstract only).
Mehrishi , et al. Electrophoresis of cells and the biological relevance of surface charge. Electrophoresis.2002;23:1984-1994.
Melville, et al. Direct magnetic separation of red cells from whole blood. Nature. 1975; 255:706.
Meng, et al.: "Design and Synthesis of a Photocleavable Fluorescent Nucleotide 3'-O-Allyl-dGTPPC-Bodipy-FL-510 as a Reversible Terminator for DNA Sequencing by Synthesis", J. Org. Chem. 2006, 71, pp. 3248-3252, XP-002652986.
Metzker, et al. Sequencing technologies—the next generation. Nature Reviews Genetics 11, 31-46 (Jan. 2010) | DOI:10.1038/nrg2626.
Mirzabekov, et al. DNA sequencing by hybridization—a megasequencing method and a diagnostic tool? Trends in Biotechnology, vol. 12, Issue 1, Jan. 1994, pp. 27-32.
Mohamed, et al. A Micromachined Sparse Cell Isolation Device: Application in Prenatal Diagnostics. Nanotech 2006 vol. 2; 641-644. (Abstract only).
Mohamed, et al. Biochip for separating fetal cells from maternal circulation. J Chromatogr A. Aug. 31, 2007;1162(2):187-92.
Mohamed, et al. Development of a rare cell fractionation device: application for cancer detection. IEEE Trans Nanobioscience. 2004; 3(4): 251-6.
Moore, et al. Lymphocyte fractionation using immunomagnetic colloid and a dipole magnet flow cell sorter. J Biochem Biophys Methods. 1998;37:11-33.

(56) References Cited

OTHER PUBLICATIONS

Moorhead, et al. Optimal genotype determination in highly multiplexed SNP data. Eur. J. Hum. Genet. 2006;14(2):207-15. (published online Nov. 23, 2005).
Mueller, et al. Isolation of fetal trophoblast cells from peripheral blood of pregnant women. The Lancet. 1990;336:197-200.
Muller, et al. Moderately repeated DNA sequences specific for the short arm of the human Y chromosome are present in XX makes and reduced in copy number in an XY female. 1986;14:1325-1340.
Mullis, et al. Specific Enzymatic Amplification of DNA In Vitro: The Polymerase Chain Reaction. Cold Spring Harbor Symposia on Quantitative Biolgy 1986;51:263-273.
Murakami, et al. A novel single cell PCR assay: detection of human T lymphotropic virus type I DNA in lymphocytes of patients with adult T cell leukemia. Leukemia. Oct. 1998;12(10):1645-50.
Murthy, et al. Assessment of multiple displacement amplification for polymorphism discovery and haplotype determination at a highly polymorphic locus, MC1R. Hum. Mutat. 2005; 26(2):145-52.
Myers, et al. Detection of single base substitutions by ribonuclease cleavage at mismatches in RNA:DNA duplexes. Science. Dec. 13, 1985;230(4731):1242-6.
Nagrath, et al. Isolation of rare circulating tumour cells in cancer patients by microchip technology. Nature. 2007; 450: 1235-1241 (with Supplemental pp. 1-10).
Nannya, et al. A robust algorithm for copy number detection using high-density oligonucleotide single nucleotide polymorphism genotyping arrays. Cancer Res. Jul. 15, 2005;65(14):6071-9.
Nelson, et al. Genotyping Fetal DNA by Non-Invasive Means: Extraction From Maternal Plasma. Vox Sang. 2001;80:112-116.
Newcombe, R. G. Two-sided confidence intervals for the single proportion: comparison of seven methods. Statistics in Medicine. 1998; 17:857-872.
Ng, et al. "The Concentration of Circulating Corticotropin-releasing Hormone mRNA in Maternal Plasma Is Increased in Preeclampsia," Clinical Chemistry, 2003, vol. 49, No. 5, 727-731.
Notice of Allowance and Issue Fee dated Dec. 9, 2010 issued in U.S. Appl. No. 11/701,686.
Notice of allowance dated Jun. 21, 2012 for U.S. Appl. No. 12/815,647.
Notice of allowance dated Oct. 5, 2012 for U.S. Appl. No. 11/763,421.
Notice of allowance dated Dec. 23, 2011 for U.S. Appl. No. 12/230,628.
Notice of allowance dated Dec. 29, 2011 for U.S. Appl. No. 11/763,245.
Notice of allowance dated Jul. 12, 2011 with allowed claims for U.S. Appl. No. 12/393,803.
Oakey et al. Laminar Flow-Based Separations at the Microscale. Biotechnology Progress. 2002; pp. 1439-1442.
Office action (Ex parte Quayle) dated May 13, 2011 for U.S. Appl. No. 11/763,421.
Office Action dated Jan. 12, 2009 for U.S. Appl. No. 11/763,133.
Office Action dated Jan. 27, 2010 for U.S. Appl. No. 11/701,686.
Office action dated Jan. 28, 2009 for U.S. Appl. No. 11/701,686.
Office action dated Jan. 30, 2012 for Application No. CN 200780030309.3.
Office action dated Feb. 4, 2010 for U.S. Appl. No. 11/067,102.
Office action dated Feb. 15, 2011 for U.S. Appl. No. 11/763,426.
Office action dated Mar. 4, 2009 for U.S. Appl. No. 11/228,454.
Office action dated Mar. 7, 2012 for U.S. Appl. No. 12/816,043.
Office action dated Mar. 11, 2010 for U.S. Appl. No. 11/763,245.
Office action dated Mar. 20, 2013 for U.S. Appl. No. 12/815,674.
Office action dated Mar. 29, 2011 for U.S. Appl. No. 11/763,245.
Office action dated Apr. 4, 2008 for U.S. Appl. No. 11/067,102.
Office action dated Apr. 4, 2012 for EP Application No. 07784444.7.
Office action dated Apr. 4, 2013 for U.S. Appl. No. 12/689,517.
Office action dated Apr. 5, 2012 for U.S. Appl. No. 12/751,931.
Office action dated Apr. 9, 2013 for U.S. Appl. No. 13/306,520.
Office action dated Apr. 12, 2012 for U.S. Appl. No. 12/815,647.
Office action dated Apr. 13, 2009 for U.S. Appl. No. 11/067,102.
Office action dated Apr. 24, 2012 for EP Application No. 07784442.1.
Office action dated Apr. 25, 2011 for U.S. Appl. No. 12/393,803 with pending claims.
Office action dated May 4, 2009 for U.S. Appl. No. 11/763,431.
Office action dated May 6, 2011 for U.S. Appl. No. 11/763,133.
Office action dated May 12, 2011 for U.S. Appl. No. 12/230,628.
Office action dated May 18, 2011 for U.S. Appl. No. 12/413,467.
Office action dated May 26, 2011 for U.S. Appl. No. 11/762,750.
Office action dated May 31, 2013 for U.S. Appl. No. 13/835,926.
Office action dated Jun. 3, 2013 for U.S. Appl. No. 13/306,640.
Office action dated Jun. 3, 2013 for U.S. Appl. No. 13/837,974.
Office action dated Jun. 4, 2012 for U.S. Appl. No. 11/762,747.
Office action dated Jun. 5, 2012 for U.S. Appl. No. 12/393,833.
Office action dated Jun. 5, 2013 for U.S. Appl. No. 12/751,940.
Office action dated Jun. 14, 2010 for U.S. Appl. No. 11/763,426.
Office action dated Jun. 15, 2007 for U.S. Appl. No. 11/067,102.
Office action dated Jun. 18, 2012 for U.S. Appl. No. 12/751,908.
Office action dated Jun. 18, 2012 for U.S. Appl. No. 12/751,940.
Office action dated Jun. 22, 2012 for Applicatioin No. AU 2007260676.
Office action dated Jul. 2, 2010 for EP Application No. 07784442.1.
Office action dated Jul. 9, 2012 for U.S. Appl. No. 11/762,750.
Office action dated Jul. 10, 2009 for U.S. Appl. No. 11/763,421.
Office action dated Jul. 10, 2012 for U.S. Appl. No. 13/433,232.
Office action dated Jul. 26, 2011 for U.S. Appl. No. 11/763,245.
Office action dated Aug. 1, 2008 for U.S. Appl. No. 11/067,102.
Office action dated Aug. 1, 2012 for U.S. Appl. No. 12/815,674.
Office action dated Aug. 2, 2010 for EP Application No. 07784444.7.
Office action dated Aug. 7, 2013 for U.S. Appl. No. 13/863,992.
Office action dated Aug. 27, 2010 for U.S. Appl. No. 11/762,747.
Office Action dated Sep. 8, 2010 for U.S. Appl. No. 11/701,686.
Office action dated Sep. 10, 2010 for U.S. Appl. No. 11/762,750.
Office Action dated Sep. 11, 2009 for U.S. Appl. No. 11/701,686.
Office action dated Sep. 14, 2012 for U.S. Appl. No. 12/393,833.
Office action dated Sep. 17, 2010 for U.S. Appl. No. 11/067,102.
Office action dated Sep. 22, 2011 for U.S. Appl. No. 12/815,647.
Office action dated Sep. 23, 2009 for EP Application No. EP07763674.4 with pending claims.
Office action dated Sep. 23, 2009 for EP Application No. EP07763674.4.
Office action dated Sep. 27, 2010 for U.S. Appl. No. 12/413,485.
Office action dated Sep. 27, 2013 for U.S. Appl. No. 12/816,043.
Office action dated Oct. 24, 2011 for U.S. Appl. No. 11/762,747.
Office action dated Oct. 25, 2012 for U.S. Appl. No. 12/816,043.
Office action dated Oct. 29, 2010 for U.S. Appl. No. 12/230,628.
Office action dated Nov. 3, 2009 for U.S. Appl. No. 11/763,133.
Office action dated Dec. 1, 2009 for U.S. Appl. No. 11/763,426.
Office action dated Dec. 2, 2008 for U.S. Appl. No. 11/762,747.
Office action dated Dec. 3, 2008 for U.S. Appl. No. 11/763,426.
Office action dated Dec. 10, 2013 for CA Application No. 2655272.
Office action dated Dec. 13, 2013 for U.S. Appl. No. 13/306,698.
Office action dated Dec. 16, 2013 for U.S. Appl. No. 13/863,992.
Office action dated Dec. 31, 2009 for U.S. Appl. No. 11/763,421.
Office action dated Dec. 31, 2009 for U.S. Appl. No. 11/762,750.
Office action dated Dec. 31, 2011 for U.S. Appl. No. 11/763,421.
Office action dated Mar. 7, 2013 for European Application No. 11182181.
Olson, et al. A Common Language for Physical Mapping of the Human Genome. "A common language for physical mapping of the human genome." Science 245.4925 (1989): 1434-1435. Sep. 29, 1989.
Olson, et al. An In Situ Flow Cytometer for the Optical Analysis of Individual Particles in Seawater. Available at http://www.whoi.edu/science/B/Olsonlab/insitu2001.htm. Accessed Apr. 24, 2006.
Oosterwijk, et al. Prenatal diagnosis of trisomy 13 on fetal cells obtained from maternal blood after minor enrichment. Prenat Diagn. 1998;18(10):1082-5.
Ottesen, et al. Microfluidic Digital PCR Enables Multigene Analysis of Individual Environmental Bacteria. Science. Dec. 1, 2006; 314(5804):1464-1467. (Abstract only).
Owen, et al. High gradient magnetic separation of erythrocytes. Biophys. J. 1978; 22:171-178.

(56) References Cited

OTHER PUBLICATIONS

Paez, et al. Genome coverage and sequence fidelity of phi29 polymerase-based multiple strand displacement whole genome amplification. Nucleic Acids Res. May 18, 2004;32(9):e71.
Pallavicini, et al. Analysis of fetal cells sorted from maternal blood using fluorescence in situ hybridization. The American Journal of Human Genetics. Oct. 1992. Supplemental to vol. 51, No. 4: 1031.
Parano, et al. Fetal Nucleated red blood cell counts in peripheral blood of mothers bearing Down Syndrome fetus. Neuropediatrics. 2001; 32(3):147-149. (Abstract only).
Parano, et al. Noninvasive Prenatal Diagnosis of Chromosomal Aneuploidies by Isolation and Analysis of Fetal Cells from Maternal Blood. Am. J. Med. Genet. 101:262-7 (2001).
Paterlini-Brechot, et al. Circulating tumor cells (CTC) detection: Clinical impact and future directions. Cancer Letter. 2007. (In press, 25 pages.) Available at www.sciencedirect.com.
Paul, et al. Single-molecule dilution and multiple displacement amplification for molecular haplotyping. Biotechniques. 2005; 38(4):553-4, 556, 558-9.
Pawlik, et al. Prodrug Bioactivation and Oncolysis of Diffuse Liver Metastases by a Herpes Simplex Virus 1 Mutant that Expresses the CYP2B1 Transgene. Cancer. 2002;95:1171-81.
Peixoto, et al. Quantification of multiple gene expression in individual cells. Genome Res. Oct. 2004;14(10A):1938-47.
Pending Claims and Preliminary Amendment filed Nov. 19, 2010 for U.S. Appl. No. 11/763,133.
Pending claims and preliminary amendment filed Dec. 10, 2010 for U.S. Appl. No. 11/763,245.
Pending claims filed with the USPTO on Apr. 26, 2010 for U.S. Appl. No. 11/067,102.
Peng, et al. Real-time detection of gene expression in cancer cells using molecular beacon imaging: new strategies for cancer research. Cancer Res. 2005; 65(5):1909-17.
Pertl, et al. "Fetal DNA in Maternal Plasma: Emerging Clinical Applications," Obstetrics and Gynecology, Sep. 2001, vol. 98, No. 3, 483-490.
Petersen, et al. The Promise of Miniaturized Clinical Diagnostic Systems. IVD Technol. 4:43-49 (1998).
Pfaffl, et al. Relative expression software tool (REST) for groupwise comparison and statistical analysis of relative expression results in real-time PCR. Nucleic Acids Res. May 1, 2002;30(9):e36.
Pinkel, et al. Cytogenetic Analysis Using Quantitative, Highsensitivity, Fluorescence Hybridization. Genetics. 1986;83:2934-2938.
Pinkel, et al. Fluorescence in situ Hybridization with Human Chromosome-specific Libraries: Detection of Trisomy 21 and Translocations of Chromosome 4. Genetics.1988;85:9138-9142.
Pinkel, et al. Detection of structural chromosome abberations in metaphase in metaphase spreads and interphase nuclei by in situ hybridization high complexity probes which stain entire human chromosomes. The American Journal of Human Genetics. Sep. 1988. Supplemental to vol. 43, No. 3: 0471.
Pinzani, et al. Isolation by size of epithelial tumor cells in peripheral blood of patients with breast cancer: correlation with real-time reverse transcriptase-polymerase chain reaction results and feasibility of molecular analysis by laser microdissection. Hum Pathol. 2006; 37(6):711-8.
Pohl et al. Principle and applications of digital PCR. Expert Rev Mol Diagn. Jan. 2004;4(1):41-7.
Poon, et al. "Circulating fetal DNA in maternal plasma," ClinicalChimica Acta, 2001, vol. 313, 151-155.
Potti, et al. Genomic signatures to guide the use of chemotherapeutics. Nat Med. 2006; 12(11):1294-1300.
Preliminary Amendments to the Claims. Filed Jul. 11, 2013 with U.S. Patent Office for U.S. Appl. No. 13/738,268.
Price, et al. Prenatal Diagnosis with Fetal Cells Isolated from Maternal Blood by Multiparameter Flow Cytometry. Am. J. Obstet. Gynecol. 1991; 165:1731-7.
Prieto, et al. Isolation of fetal nucleated red blood cells from maternal blood in normal and aneuploid pregnancies. Clin Chem Lab Med. Jul. 2002;40(7):667-72.
Product literature for GEM, a system for blood testing: GEM Premier 3000. Avaiable at http://www.ilus.com/premier_gem3000_iqm.asp. Accessed Apr. 24, 2006.
Pruitt, et al. RefSeq and LocusLink: NCBI gene-centered resources. Nucl. Acids Res. (2001) vol. 29 No. 1: 137-140. DOI: 10.1093/nar/29.1.137.
Purwosunu, et al. Clinical potential for noninvasive prenatal diagnosis through detection of fetal cells in maternal blood. Taiwan J Obstet Gynecol. Mar. 2006;45(1):10-20.
Raeburn, P. Fetal Cells Isolated in Women's Blood. Associated Press (Jul. 28, 1989) [electronic version].
Rahil, et al. Rapid detection of common autosomal aneuploidies by quantitative fluorescent PCR on uncultured amniocytes, European Journal of Human Genetics, 2002, vol. 10, 462-466.
Request for Continued Examination by applicant with claim set dated Mar. 26, 2010 in Response to Final Office Action dated Nov. 3, 2009 for U.S. Appl. No. 11/763,133.
Request for Continued Examination by applicant with claim set dated Mar. 26, 2010 in Response to Final Office Action dated Dec. 1, 2009 for U.S. Appl. No. 11/763,426.
Response dated Nov. 24, 2010 to Office action dated Jun. 14, 2010 with Pending Claims for U.S. Appl. No. 11/763,426.
Response filed Dec. 26, 2012 with claims for U.S. Appl. No. 12/393,833.
Rickman, et al. Prenatal diagnosis by array-CGH. European Journal of Medical Genetics. 2005; 48:232-240.
Rolle, et al. Increase in number of circulating disseminated epithelia cells after surgery for non-small cell lung cancer monitored by MAINTRAC is a predictor for relapse: a preliminary report. World Journal of Surgical Oncology. 2005; 9 pages.
Rosato, M. Verinata Health, Inc.'s Preliminary Patent Owner Response Pursuant to 37 C.F.R. §42.107(a). Dated Jul. 29, 2013. For Case IPR2013-00276. U.S. Pat. No. 8,318,430.
Rosato, Verinata Health Inc.'s Preliminary Patent Owner Response Pursuant to 37 C.F.R. §42.107(a). Dated Jul. 29, 2013. For Case IPR2013-00277. U.S. Pat. No. 8,318,430.
Ruan, et al. Identification of clinically significant tumor antigens by selecting phage antibody library on tumor cells in situ using laser capture microdissection. Molecular & Cellular Proteomics. 2006; 5(12): 2364-73.
Sakhnini, et al. Magnetic behavior of human erythrocytes at different hemoglobin states. Eur Biophys J. Oct. 2001;30(6):467-70.
Saleeba, et al. Chemical cleavage of mismatch to detect mutations. Methods Enzymol. 1993;217:286-95.
Samura, et al. Diagnosis of trisomy 21 in fetal nucleated erythrocytes from maternal blood by use of short tandem repeat sequences. Clin. Chem. 2001; 47(9):1622-6.
Samura, et al. Female fetal cells in maternal blood: use of DNA polymorphisms to prove origin. Hum. Genet. 2000;107(1):28-32.
Sato, et al. Individual and Mass Operation of Biological Cells Using Micromechanical Silicon Devices. Sensors and Actuators. 1990;A21-A23:948-953.
Schaefer, et al. The Clinical Relevance of Nucleated Red Blood Cells counts. Sysmex Journal International. 2000; 10(2):59-63.
Schröder, et al. Fetal Lymphocytes in the Maternal Blood. The Journal of Hematolog:Blood. 1972;39:153-162.
Sehnert, et al. Optimal Detection of Fetal Chromosomal Abnormalities by Massively Parallel DNA Sequencing of Cell-Free Fetal DNA from Maternal Blood. Clin Chem. Apr. 25, 2011. [Epub ahead of print].
Sethu, et al. Continuous Flow Microfluidic Device for Rapid Erythrocyte Lysis. Anal. Chem. 76:6247-6253 (2004).
Shen, et al. High-throughput SNP genotyping on universal bead arrays. Mutat. Res. 2005; 573:70-82.
Shendure, et al. Accurate multiplex polony sequencing of an evolved bacterial genome. Science. 2005; 309:1728-32.
Shendure, et al. Next-generation DNA sequencing. Nature. 2008; 26(10):1135-1145.

(56) References Cited

OTHER PUBLICATIONS

Sherlock, et al. Assessment of diagnostic quantitative fluorescent multiplex polymerase chain reaction assays performed on single cells. Ann. Hum. Genet. 1998; 62:9-23.
Sitar, et al. The Use of Non-Physiological Conditions to Isolate Fetal Cells from Maternal Blood. Exp. Cell. Res. 2005; 302:153-61.
Sohda, et al. The Proportion of Fetal Nucleated Red Blood Cells in Maternal Blood: Estimation by FACS Analysis. Prenat. Diagn. 1997; 17:743-52.
Solexa Genome Analysis System. 2006; 1-2.
Sparkes, et al. "New Molecular Techniques for the Prenatal Detection of Chromosomal Aneuploidy," JOGC, Jul. 2008, No. 210, 617-621.
Stipp, D. IG Labs Licenses New Technology for Fetal Testing. The Wall Street Journal. Aug. 10, 1990:B5.
Stoecklein, et al. SCOMP is superior to degenerated oligonucleotide primed-polymerase chain reaction for global amplification of minute amounts of DNA from microdissected archival tissue samples. Am J Pathol. 2002; 161(1):43-51.
Stoughton, et al. Data-adaptive algorithms for calling alleles in repeat polymorphisms. Electrophoresis. 1997;18(1):1-5.
Sun, et al. Whole-genome amplification: relative efficiencies of the current methods. Leg Med. 2005; 7(5):279-86.
Supplemental Amendment and Transmittal of Terminal Disclaimer dated Oct. 18, 2011 for U.S. Appl. No. 12/230,628.
Sykes, et al. Quantitation of targets for PCR by use of limiting dilution. Biotechniques. Sep. 1992;13(3):444-9.
Tanaka, et al. "Genome-wide expression profiling of mid-gestation placenta and embryo using a 15,000 mouse developmental cDNA microarray," PNAS, Aug. 2000, vol. 97, No. 16, 9127-9132.
Tettelin, et al. The nucleotide sequence of *Saccharomyces cerevisiae* chromosome VII. Nature. May 29, 1997;387(6632 Suppl):81-4.
Thomas, et al. Specific Binding and Release of Cells from Beads Using Cleavable Tettrametric Antibody Complexes. Journal of Immunological Methods 1989;120:221-231.
Tibbe, et al. Statistical considerations for enumeration of circulating tumor cells. Cytometry A. Mar. 2007;71(3):154-62.
Toner, et al. Blood-on-a-Chip. Annu. Rev. Biomed. Eng. 7:77-103, C1-C3 (2005).
Trask, et al. Detection of DNA Sequences and Nuclei in Suspension by In Situ Hybridization and Dual Beam Flow Cytometry. Science. 1985;230:1401-1403.
Troeger, et al. Approximately half of the erythroblasts in maternal blood are of fetal origin. Mol Hum Reprod. 1999; 5(12):1162-5.
Tufan, et al., Analysis of Cell-Free Fetal DNA from Maternal Plasma and Serum Using a Conventional Multiplex PCR: Factors Influencing Success. 2005. Turk. J. Med. Sci. 35:85-92.
Uitto, et al. Probing the fetal genome: progress in non-invasive prenatal diagnosis. Trends Mol Med. Aug. 2003;9(8):339-43.
Van Raamsdonk, et al. Optimizing the detection of nascent transcripts by RNA fluorescence in situ hybridization. Nucl. Acids. Res. 2001; 29(8):e42.
Venter, et al. The Sequence of the Human Genome. Science Feb. 16, 2001; vol. 291 No. 5507 pp. 1304-1351 DOI: 10.1126/science.1058040.
Verinata Health. Complaint for Patent Infringement. Case: 12-cv-05501-SI; Dated Oct. 25, 2012.
Verinata Health. Plaintiffs' Opposition to Defendants' Motion to Dismiss Plaintiffs' Claims for Patent Infringement Against Laboratory Corporation of America and Claims for Enhanced Damages Against All Defendants. Case: 12-cv-05501-SI; Dated Jan. 25, 2013.
Verinata Health: Joint Claim Construction and Prehearing Statement. Case: 12-cv-05501-SI; Dated May 3, 2013.
Voelkerding, et al. Digital fetal aneuploidy diagnosis by next-generation sequencing. Clin Chem. Mar. 2010;56(3):336-8.
Vogelstein, et al. "Digital PCR." Proc Natl. Acad Sci. USA, Aug. 1999, vol. 96., 9236-9241.
Voldberg, et al. Epidermal growth factor receptor (EGFR) and EGFR mutations, function and possible role in clinical trials. Ann Oncol. Dec. 1997;8(12):1197-206.
Volkmuth, et al. DNA electrophoresis in microlithographic arrays. Nature. 1992; 358:600-602.
Volkmuth, et al. Observation of Electrophoresis of Single DNA Molecules in Nanofabricated Arrays. Presentation at joint annual meeting of Biophysical Society and the American Society for Biochemistry and Molecular Biology. Feb. 9-13, 1992.
Von Eggeling, et al. Determination of the origin of single nucleated cells in maternal circulation by means of random PCR and a set of length polymorphisms. Hum Genet. Feb. 1997;99(2):266-70.
Vona, et al. Enrichment, immunomorphological, and genetic characterization of fetal cells circulating in maternal blood. Am J Pathol. Jan. 2002;160(1):51-8.
Voss, et al. Efficient low redundancy large-scale DNA sequencing at EMBL. Journal of Biotechnology, vol. 41, Issues 2-3, Jul. 31, 1995, pp. 121-129.
Voullaire, et al. Detection of aneuploidy in single cells using comparative genomic hybridization. Prenat Diagn. 1999; 19(9):846-51.
Vrettou, et al. Real-time PCR for single-cell genotyping in sickle cell and thalassemia syndromes as a rapid, accurate, reliable, and widely applicable protocol for preimplantation genetic diagnosis. Human Mutation. 2004; 23(5):513-21.
Wachtel, et al. Fetal Cells in the Maternal Circulation: Isolation by Multiparameter Flow Cytometry and Confirmation by Polymerase Chain Reaction. Human Reproduction. 1991;6:1466-1469.
Wang, et al. Allele quantification using molecular inversion probes (MIP). Nucleic Acids Research. 2005; 33(21); e183 (14 pages).
Wapner, et al. First-trimester screening for trisomies 21 and 18. N. Engl. J. Med. 2003; 349:1405-1413.
Warren, et al. Transcription factor profiling in individual hematopoietic progenitors by digital RT-PCR. PNAS. Nov. 21, 2006; 103(47):17807-17812.
Washizu, et al. Handling Biological Cells Utilizing a Fluid Integrated Circuit. IEEE Industry Applications Society Annual Meeting Presentations. Oct. 2-7, 1988;: 1735-40.
Washizu, et al. Handling Biological Cells Utilizing a Fluid Integrated Circuit. IEEE Transactions of Industry Applications. 1990; 26: 352-8.
Weigl, et al. Microfluidic Diffusion-Based Separation and Detection. Science. 1999; pp. 346-347.
Wheeler, et al. The complete genome of an individual by massively parallel DNA sequencing. Nature 452, 872-876 (Apr. 17, 2008) | DOI:10.1038/nature06884; Accepted Mar. 4, 2008.
White, et al. Digital PCR provides sensitive and absolute calibration for high throughput sequencing. BMC Genomics. Mar. 19, 2009;10:116.
Williams, et al. Comparison of cell separation methods to entrich the proportion of fetal cells in material blood samples. The American Journal of Human Genetics. Oct. 1992. Supplemental to vol. 51, No. 4: 1049.
Xiong, et al. "A simple, rapid, high-fidelity and cost-effective PCR-based two-step DNA synthesis method for long gene sequences," Nucleic Acids Research, Apr. 19, 2004, vol. 32, No. 12, e98.
Yang, et al. Prenatal diagnosis of trisomy 21 with fetal cells i maternal blood using comparative genomic hybridization. Fetal Diagn Ther. 2006; 21:125-133.
Yang, et al. Rapid Prenatal Diagnosis of Trisomy 21 by Real-time Quantitative Polymerase Chain Reaction with Amplification of Small Tandem Repeats and S1OOB in Chromosome 21. Yonsei Medical Journal, 2005, vol. 46, No. 2, 193-197.
Yu, et al. Objective Aneuploidy Detection for Fetal and Neonatal Screening Using Comparative Genomic Hybridization (CGH). Cytometry. 1997; 28(3): 191-197. (Absbract).
Zavala, et al. Genomic GC content prediction in prokaryotes from a sample of genes. Gene. Sep. 12, 2005;357(2):137-43.
Zhao, et al. An integrated view of copy number and allelic alterations in the cancer genome using single nucleotide polymorphism arrays. Cancer Res. May 1, 2004;64(9):3060-71.
Zhen, et al. Poly-FISH: a technique of repeated hybridizations that improves cytogenetic analysis of fetal cells in maternal blood. Prenat Diagn. 1998; 18(11):1181-5.

(56) References Cited

OTHER PUBLICATIONS

Zheng, et al. Fetal cell identifiers: results of microscope slide-based immunocytochemical studies as a function of gestational age and abnormality. Am J Obstet Gynecol. May 1999;180(5):1234-9.
Zhu, et al. Single molecule profiling of alternative pre-mRNA splicing. Science. Aug. 8, 2003;301(5634):836-8.
Zimmerman et al. QIAGEN News. 2003. e12. Available via uri: <b2b.qiagen.com/literature/qiagennews/weeklyarticle/apr03/e12/default.aspx>.
Zimmerman, et al. Novel real-time quantitative PCR test for trisomy 21. Jan. 1, 2002. Clinical Chemistry, American Association for Clinical Chemistry. 48:(2) 362-363.
Zimmermann, Bernhard. "Molecular Diagnosis in Prenatal Medicine," Ph.D. Thesis, 2004.
Zuska, P. Microtechnology Opens Doors to the Universe of Small Space, MD&DI Jan. 1997, p. 131.
Fan, et al. Highly Parallel Genomic Assays. Aug. 2006. Nat. Rev. Genet. 7(8):632-44.
Office action dated Feb. 5, 2014 for U.S. Appl. No. 12/689,517.
Office action dated Mar. 20, 2014 for U.S. Appl. No. 12/816,043.
Office action dated Mar. 21, 2014 for U.S. Appl. No. 12/815,674.
Office action dated Apr. 28, 2014 for U.S. Appl. No. 12/689,548.
Office action dated Nov. 7, 2014 for U.S. Appl. No. 13/831,342.
Office action dated Nov. 24, 2014 for U.S. Appl. No. 12/689,548.
U.S. Appl. No. 14/705,239, filed May 6, 2015, Kapur, et al.
Advisory action dated Mar. 4, 2015 for U.S. Appl. No. 12/689,548.
European office action dated May 22, 2015 for EP Application No. 07798579.4.
International Preliminary Report on Patentability dated Dec. 16, 2008 for PCT Application No. US2007/071248.
Notice of allowance dated Jan. 26, 2015 for U.S. Appl. No. 13/835,926.
Office action dated Jan. 26, 2015 for CA Application No. 2655272.
Office action dated Jan. 30, 2014 for U.S. Appl. No. 13/837,974.
Office action dated Feb. 23, 2015 for U.S. Appl. No. 12/689,517.
Office action dated Mar. 11, 2015 for U.S. Appl. No. 13/737,730.
Office action dated Apr. 7, 2015 for U.S. Appl. No. 13/829,971.
Office action dated Apr. 29, 2015 for U.S. Appl. No. 13/794,503.
Office action dated May 8, 2015 for U.S. Appl. No. 12/816,043.
Office action dated May 11, 2015 for U.S. Appl. No. 13/863,992.
Office action dated Jul. 16, 2015 for U.S. Appl. No. 13/837,974.
Office action dated Jul. 21, 2015 for U.S. Appl. No. 12/689,548.
Office action dated Aug. 1, 2014 for U.S. Appl. No. 12/816,043.
Office action dated Aug. 19, 2015 for U.S. Appl. No. 12/689,517.
Office action dated Sep. 18, 2015 for U.S. Appl. No. 12/816,043.
Office action dated Dec. 10, 2014 for U.S. Appl. No. 12/751,940.
Office action dated Dec. 12, 2014 for U.S. Appl. No. 13/738,268.
Bianchi, et al. Large amounts of cell-free fetal DNA are present in amniotic fluid. Clinical chemistry 47.10 (2001): 1867-1869.
Bischoff, et al. Cell-free fetal DNA and intact fetal cells in maternal blood circulation: implications for first and second trimester non-invasive prenatal diagnosis. Human reproduction update 8.6 (2002): 493-500.
Brown, et al. Aneuploidy detection in mixed DNA samples by methylation-sensitive amplification and microarray analysis. Clinical chemistry 56.5 (2010): 805-813.
Brown, et al. Validation of QF-PCR for prenatal aneuploidy screening in the United States. Prenatal diagnosis 26.11 (2006): 1068-1074.
Chim, et al. Detection of the placental epigenetic signature of the *Maspin* gene in maternal plasma. Proceedings of the National Academy of Sciences of the United States of America 102.41 (2005): 14753-14758.
Chiu, et al. Noninvasive prenatal diagnosis by analysis of fetal DNA in maternal plasma. Clinical Applications of PCR (2006): 101-109.
Evans, et al. Digital PCR for noninvasive detection of aneuploidy: power analysis equations for feasibility. Fetal diagnosis and therapy 31.4 (2012): 244-247.
Grundevik, et al. Molecular Diagnostics of Aneuploidies. Chalmers University of Technology. May 17, 2005.
Kaiser, J. An earlier look at baby's genes. Science 309.5740 (2005): 1476.
Khattabi, et al. Could Digital PCR Be an Alternative as a Non-Invasive Prenatal Test for Trisomy 21: A Proof of Concept Study. PloS one 11.5 (2016): e0155009.
Mann, et al. Strategies for the rapid prenatal diagnosis of chromosome aneuploidy. European Journal of Human Genetics 12.11 (2004): 907-915.
Notice of allowance dated Jul. 27, 2016 for U.S. Appl. No. 12/816,043.
Office action dated Mar. 14, 2016 for U.S. Appl. No. 12/816,043.
Office action dated Sep. 16, 2016 for U.S. Appl. No. 12/689,517.
Office action dated Dec. 1, 2016 for U.S. Appl. No. 13/794,503.
Office action dated Dec. 27, 2016 for U.S. Appl. No. 13/863,992.
Opposition dated Apr. 10, 2014 by Olswang against EP Application No. EP07763674.4.
Opposition dated Jun. 12, 2015 by Premaitha Health PLC against EP Application No. EP07763674.4.
Poon, et al. Differential DNA methylation between fetus and mother as a strategy for detecting fetal DNA in maternal plasma. Clinical chemistry 48.1 (2002): 35-41.
Sekizawa, et al. Recent advances in non-invasive prenatal DNA diagnosis through analysis of maternal blood. Journal of Obstetrics and Gynaecology Research 33.6 (2007): 747-764.
Tong, et al. Noninvasive prenatal detection of fetal trisomy 18 by epigenetic allelic ratio analysis in maternal plasma: theoretical and empirical considerations. Clinical Chemistry 52.12 (2006): 2194-2202.
Vogelstein, et al. Allelotype of colorectal carcinomas. Science 244 (4): 207-211. 1989.
Wong, et al. Circulating placental RNA in maternal plasma is associated with a preponderance of 5' mRNA fragments: implications for noninvasive prenatal diagnosis and monitoring. Clinical chemistry 51.10 (2005): 1786-1795.
Yu, et al. Size-based molecular diagnostics using plasma DNA for noninvasive prenatal testing. Proceedings of the National Academy of Sciences 111.23 (2014): 8583-8588.
Zhou, et al. Counting alleles reveals a connection between chromosome 18q loss and vascular invasion. Nature biotechnology 19.1 (2001): 78-81.
Zhou, et al. Counting alleles to predict recurrence of early-stage colorectal cancers. The Lancet 359.9302 (2002): 219-225.
Zimmerman, et al. Digital PCR: a powerful new tool for noninvasive prenatal diagnosis? 2008 Prenat Diagn 28, 1087-1093.
U.S. Appl. No. 60/951,438, filed Jul. 23, 2007, Lo et al.
Amendment to the Claims dated Jun. 16, 2014 for U.S. Appl. No. 13/863,992.
Amendment to the Claims dated Dec. 5, 2013 for U.S. Appl. No. 12/751,940.
Amendments to the Claims. Filed Oct. 14, 2014 with U.S. Patent Office for U.S. Appl. No. 13/831,342.
Chang, et al. Assessment of Plasma DNA Levels, Allelic Imbalance, and CA 125 as Diagnostic Tests for Cancer. Nov. 20, 2002. J. Nat'l Cancer Inst. 94(22):1697-1703.
Coble, et al. Characterization of New MiniSTR Loci to Aid Analysis of Degraded DNA. Jan. 2005. J. Forensic Sci. 50(1):43-53.
Dahl, et al. Multigene Amplification and Massively Parallel Sequencing for Cancer Mutation Discovery. May 29, 2007. PNAS USA 104(22):9387-9392.
Declaration of Atul J. Butte, M.D. PhD. in Support of Patent Owner's Response to Inter Partes Review of U.S. Pat. No. 8,316,430. US Patent Office. Dated Jan. 16, 2014.
Deposition of Dr. Cynthia Casson Morton. US Patent Office. Dated Dec. 10, 2013.
Deposition of Dr. Robert Nussbaum. US Patent Office. Dated Dec. 11, 2013.
Deutsch, et al. Detection of aneuploidies by paralogous sequence quantification. J.Med Genet. Dec. 2004;41(12):908-15.
European office action dated Aug. 22, 2013 for EP Application No. 07798579.4.
Hall. Advanced Sequencing Technologies and their Wider Impact in Microbiology. 2007. J. Exp. Biol. 209:1518-1525.
Jama, et al. Quantification of cell-free DNA levels in maternal plasma by STR analysis. Mar. 24-28, 2010. ACMG Annual Clinical

(56) References Cited

OTHER PUBLICATIONS

Genetics Meeting Poster 398. Availabble at http://acmg.omnibooksonline.com/2010/data/papers/398.pdf. Accessed Apr. 5, 2013.
Koide, et al. Fragmentation of Cell-Free Fetal DNA in Plasma and Urine of Pregnant Women. Jul. 2005. Prenat. Diagn. 25(7):604-7.
Leon, et al. Free DNA in the serum of cancer patients and the effect of therapy. Cancer Res. Mar. 1977;37(3):646-50.
Liu, et al. Feasibility Study of Using Fetal DNA in Maternal Plasma for Non-invasive Prenatal Diagnosis. Acta Obstet. Gynecol. Scand. May 2007; 86(5):535-41.
Lo, et al. Increased Fetal DNA Concentrations in the Plasma of Pregnant Women Carrying Fetuses with Trisomy 21. Oct. 1999. Clin. Chem. 45(10):1747-51.
Lo, et al. Rapid Clearance of Fetal DNA from Maternal Plasma. Jan. 1999. Am. J. Hum. Genet. 64(1):218-24.
Office action dated Jan. 28, 2014 for U.S. Appl. No. 13/835,926.
Office action dated Mar. 15, 2016 for U.S. Appl. No. 12/751,940.
Office action dated Mar. 31, 2016for U.S. Appl. No. 13/863,992.
Pathak, et al. Circulating Cell-Free DNA in Plasma/Serum of Lung Cancer Patients as a Potential Screening and Prognostic Tool. Oct. 2006. Clin. Chem.52(10):1833-42.
Pertl, et al. Detection of Male and Female DNA in Maternal Plasma by Multiplex Fluorescent Polymerase Chain Reaction Amplification of Short Tandem Repeats. Jan. 2000. Hum. Genet. 106(1):45-9.
REPLI-g® Mini and Midi Kits pamphlet from Qiagen (Oct. 2005).
Su, et al. Human Urine Contains Small, 150 to 250 Nucleotide-Sized, Soluble DNA Derived from the Circulation and may be Useful in the Detection of Colorectal Cancer. May 2005. J. Mol. Diagn. 6(2):101-7.
Swarup, et al. Circulating (cell free) nucleic acids—A promising, non-invasive tool for early detection of several human diseases. 2007 FEBS Letters 581:795-799.
Thomas, et al. Sensitive Mutation Detection in Heterogeneous Cancer Specimens by Massively Parallel Picoliter Reactor Sequencing. Jul. 2006. Nature Medicine. 12(7):852-855.
Wright, et al. The use of cell-free fetal nucleic acids in maternal blood for noninvasive prenatal diagnosis. Hum Reprod Update. Jan.-Feb. 2009;15(1):139-51.
Zhang, et al. Whole genome amplification from a single cell: implications for genetic analysis. Proc Natl Acad Sci U S A. Jul. 1, 1992;89(13):5847-51.
Notice of allowance dated Jan. 22, 2016 for U.S. Appl. No. 13/837,974.
Notice of allowance dated Oct. 27, 2015 for U.S. Appl. No. 13/829,971.
Office action dated Dec. 22, 2015 for U.S. Appl. No. 13/794,503.
Office action dated Aug. 16, 2016 for U.S. Appl. No. 13/863,992.
Bailey et al., "Recent Segmental Duplications in the Human Genome," Science, Aug. 2002, 297(5583):1003-1007.
Extended European Search Report in Application No. 18170287.9, dated Sep. 19, 2018, 10 pages.
Jauniaux et al., "Very early prenatal diagnosis on coelomic cells using quantitative fluorescent polymerase chain reaction," Reproductive BioMedicine Online, Jan. 2003, 6:494-498.
Leary et al., "Digital karyotyping," Nature Protocols, 2007, 2(8):1973-1986.
Wang et al., "Digital karyotyping," Proc. Natl. Acad. Sci., U.S.A, Dec. 2002, 99(25):16156-16161.

\* cited by examiner

Microposts and cells

Antibody coated posts

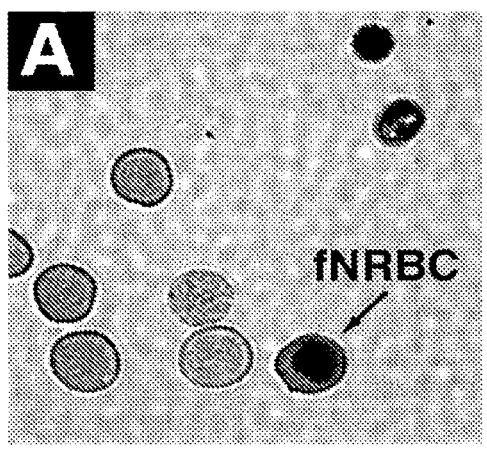 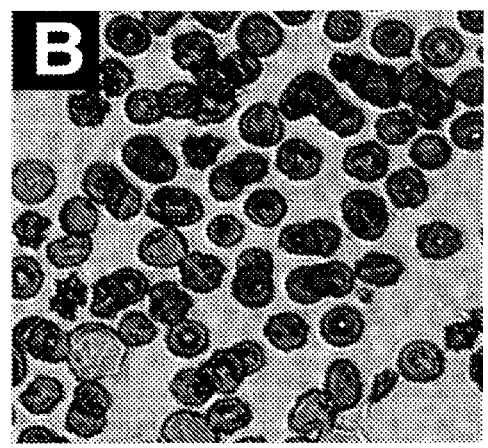
FIG. 8A                    FIG. 8B (Blue= nucleus, Red = X chromosome, Green = Y chromosome)

| Locus | Chromosomal Position |
|---|---|
| F13B | 1 q31-q32.1 |
| TPOX | 2 p23-2pter |
| FIBRA (FGA) | 4 q28 |
| CSF1PO | 5 q33.3-q34 |
| F13A | 6 p24-p25 |
| TH01 | 11 p15-15.5 |
| VWA | 12 p12-pter |
| CD4 | 12 p12-pter |
| D14S1434 | 14 q32.13 |
| CYAR04 (P450) | 15 q21.1 |
| D21S11 | 21 q11-q21 |
| D22S1045 | 22 q12.3 |

STR loci used for fetal cell detection

FIG. 12

| Oligo Name | Sequence (5'-3') | bp | Eppendorf Annealing Temp |
|---|---|---|---|
| 14S1434_F03 (SEQ ID NO. 111) | TTC TAA TAT GCA AAT GCA CAC AGA TTT CTG CT | 32 | 68 C |
| 14S1434_R03 (SEQ ID NO. 112) | TTC AGA TTC AGA CTG AAT GAC ACC ATC AGT TT | 32 | 68 C |
| CD4F_01 (SEQ ID NO. 113) | TTG GAG TCG CAA GCT GAA CTA GCG | 24 | 68 C |
| CD4R_01 (SEQ ID NO. 114) | CCA GGA AGT TGA GGC TGC AGT GAA | 24 | 68 C |
| CSF1PO_F02 (SEQ ID NO. 115) | TAA AGT GAG AAA GAA TAA CTG CAT CTT AAC CT | 32 | 68 C |
| CSF1PO_R02 (SEQ ID NO. 116) | TCT CCT TTC TCT TCA TCC CTG CAT | 27 | 68 C |
| CYAR04_F02 (SEQ ID NO. 117) | GCT CTG GAA AAC ACT CG ACC CTT CTT | 27 | 68 C |
| CYAR04_R02 (SEQ ID NO. 118) | GTG GGA GAA TCG CCT GAG TCC T | 22 | 68 C |
| D21S11_F02 (SEQ ID NO. 119) | GTC TGT TAT GGG ACT TTT CTC AGT CTC CAT | 30 | 68 C |
| D21S11_R02 (SEQ ID NO. 120) | ACA CTG AGA AGG GAG AAA CAC TGT AAG GTT TTA TAT | 36 | 68 C |
| D22S1045F_01 (SEQ ID NO. 121) | GCT AGA TTT TCC CCG ATG AT | 20 | 68 C |
| D22S1045R_01 (SEQ ID NO. 122) | ATG TAA AGT GCT CTC AAG AGT GC | 23 | 68 C |
| F13A_F02 (SEQ ID NO. 123) | GCA TGC ACC TGT AGT TCC AGC TAC T | 25 | 68 C |
| F13A_R02 (SEQ ID NO. 124) | GAG AGC AAC GTG TCC CTC CTG T | 22 | 68 C |
| F13B_F02 (SEQ ID NO. 125) | CAG AAG AGA CTG CCC TTC AGA CTT TCT AAA T | 31 | 68 C |
| F13B_R02 (SEQ ID NO. 126) | GTA CAC GCC TGT AAT CCC AGC TAC T | 25 | 68 C |
| FIBRA_F02 (SEQ ID NO. 127) | TAC ACC TTT AAA ATT CCA AAG AAA GTT CTT CT | 32 | 68 C |
| FIBRA_R02 (SEQ ID NO. 128) | CAA TTC TGC TTC TCA GAT CCT CTG ACA CT | 29 | 68 C |
| TH01_F02 (SEQ ID NO. 129) | CCA AGG CCC TTC CCA GGC T | 19 | 68 C |
| TH01_R02 (SEQ ID NO. 130) | TGA CAC TGC TAC AAC TCA CAC CAC ATT T | 28 | 68 C |
| TPOX_F02 (SEQ ID NO. 131) | AAC ACA TGT TCC CAC CTG GCC T | 21 | 68 C |
| TPOX_R02 (SEQ ID NO. 132) | CAA ACG TGA GGT TGC CTC TAC TGT CCT | 27 | 68 C |
| VWA_F02 (SEQ ID NO. 133) | AGA CTG ATC CTA TAA GGT AGA GTT CCC ACC T | 31 | 68 C |
| VWA_R02 (SEQ ID NO. 134) | TAG AGA CAG GAT AGA TGA TAA ATA GAT ACA TAG GTT | 36 | 68 C |

EXTERNAL PRIMERS FOR STR LOCI

FIG. 13

| Oligo Name | Sequence (5'-3') | bp | Product lengths | Eppendorf Annealing Temp |
|---|---|---|---|---|
| CD4F_02 (SEQ ID NO. 135) | TTG GAG TCG CAA GCT GAA CTA GC | 23 | 86-141 | 63C |
| CD4R_02 (SEQ ID NO. 136) | GCC TGA GTG ACA GAG TGA GAA CC | 23 | 86-141 | 63C |
| D14S1434F_02 (SEQ ID NO. 137) | TGT AAT AAC TCT ACG ACT GTC TGT CTG | 27 | 70-102 | 63C |
| D14S1434R_02 (SEQ ID NO. 138) | GAA TAG GAG GTG GAT GGA TGG | 21 | 70-102 | 63C |
| D21S11_F01 (SEQ ID NO. 139) | GTG AGT CAA TTC CCC AAG | 18 | 202-265 | 63C |
| D21S11_R01 (SEQ ID NO. 140) | GTT GTA TTA GTC AAT GTT CTC C | 22 | 202-265 | 63C |
| D22S1045F_02 (SEQ ID NO. 141) | ATT TTC CCC GAT GAT AGT AGT CT | 23 | 76-109 | 63C |
| D22S1045R_02 (SEQ ID NO. 142) | GCG AAT GTA TGA TTG GCA ATA TTT TT | 26 | 76-109 | 63C |
| F13B_F01 (SEQ ID NO. 143) | TGA GGT GGT GTA CTA GCA TA | 20 | 169-193 | 63C |
| F13B_R01 (SEQ ID NO. 144) | GAT CAT GCC ATT GCA CTC TA | 20 | 169-193 | 63C |
| VWA_F01 (SEQ ID NO. 145) | CCC TAG TGG ATG ATA AGA ATA ATC | 24 | 122-182 | 63C |
| VWA_R01 (SEQ ID NO. 146) | GGA CAG ATG ATA AAT ACA TAG GAT GGA TGG | 30 | 122-182 | 63C |
| CSF1PO_F01 (SEQ ID NO. 147) | TTC CAC ACA CCA CTG GCC ATC TTC | 24 | 295-327 | 68C |
| CSF1PO_R01 (SEQ ID NO. 148) | AAC CTG AGT CTG CCA AGG ACT AGC | 24 | 295-327 | 68C |
| CYAR04_F01 (SEQ ID NO. 149) | GGT AAG CAG GTA CTT AGT TAG CTA C | 25 | 172-205 | 68C |
| CYAR04_R01 (SEQ ID NO. 150) | GTT ACA GTG AGC CAA GGT CGT GAG | 24 | 172-205 | 68C |
| F13A1_F01 (SEQ ID NO. 151) | GAG GTT GCA CTC GAG CCT TTG CAA | 24 | 279-335 | 68 - 63C |
| F13A1_R01 (SEQ ID NO. 152) | TTC CTG AAT CAT CCC AGA GCC ACA | 24 | 279-335 | 68 - 63C |
| FIBRA_F01 (SEQ ID NO. 153) | ATT ATC CAA AAG TCA AAT GCC CCA TAG G | 28 | 158-286 | 68C |
| FIBRA_R01 (SEQ ID NO. 154) | ATC GAA AAT ATG GTT ATT GAA GTA GCT G | 28 | 158-286 | 68C |
| TH01_F01 (SEQ ID NO. 155) | GTG GGC TGA AAA GCT CCC GAT TAT | 24 | 171-215 | 68C |
| TH01_R01 (SEQ ID NO. 156) | ATT CAA AGG GTA TCT GGG CTC TGG | 24 | 171-215 | 68C |
| TPOX_F01 (SEQ ID NO. 157) | ACT GGC ACA GAA CAG GCA CTT AGG | 24 | 220-256 | 68C |
| TPOX_R01 (SEQ ID NO. 158) | GGA GGA ACT GGG AAC CAC ACA GGT | 24 | 220-256 | 68C |

INTERNAL PRIMERS FOR STRs LOCI

FIG. 14

DIAGNOSIS OF FETAL ABNORMALITIES USING POLYMORPHISMS INCLUDING SHORT TANDEM REPEATS

CROSS-REFERENCE

This application is a Continuation of U.S. application Ser. No. 13/738,268 filed Jan. 10, 2013; which is a Continuation of U.S. application Ser. No. 13/433,232 filed on Mar. 28, 2012; which is a Continuation of U.S. application Ser. No. 12/725,240 filed on Mar. 16, 2010; which is a Continuation of U.S. application Ser. No. 11/763,426 filed on Jun. 14, 2007; which claims the benefit of U.S. Provisional Application Ser. No. 60/804,815 filed on Jun. 14, 2006, each of which applications is incorporated herein by reference. This application also claims the benefit of U.S. Provisional Application No. 60/820,778, filed Jul. 28, 2006.

SEQUENCE LISTING

The instant application contains a Sequence Listing which has been submitted in ASCII format via EFS-Web and is hereby incorporated by reference in its entirety. Said ASCII copy, created on Jun. 6, 2013, is named 32047-717-306-Seqlisting.txt and is 36 Kilobytes in size.

BACKGROUND OF THE INVENTION

Analysis of specific cells can give insight into a variety of diseases. These analyses can provide non-invasive tests for detection, diagnosis and prognosis of diseases, thereby eliminating the risk of invasive diagnosis. For instance, social developments have resulted in an increased number of prenatal tests. However, the available methods today, amniocentesis and chorionic villus sampling (CVS) are potentially harmful to the mother and to the fetus. The rate of miscarriage for pregnant women undergoing amniocentesis is increased by 0.5-1%, and that figure is slightly higher for CVS. Because of the inherent risks posed by amniocentesis and CVS, these procedures are offered primarily to older women, i.e., those over 35 years of age, who have a statistically greater probability of bearing children with congenital defects. As a result, a pregnant woman at the age of 35 has to balance an average risk of 0.5-1% to induce an abortion by amniocentesis against an age related probability for trisomy 21 of less than 0.3%.

To eliminate the risks associated with invasive prenatal screening procedures, non-invasive tests for detection, diagnosis and prognosis of diseases, have been utilized. For example, maternal serum alpha-fetoprotein, and levels of unconjugated estriol and human chorionic gonadotropin are used to identify a proportion of fetuses with Down's syndrome, however, these tests are not one hundred percent accurate. Similarly, ultrasonography is used to determine congenital defects involving neural tube defects and limb abnormalities, but is useful only after fifteen weeks' gestation.

The methods of the present invention allow for the detection of fetal cells and fetal abnormalities when fetal cells are present in a mixed population of cells, even when maternal cells dominate the mixture.

SUMMARY OF THE INVENTION

The presence of fetal cells in maternal circulation offers the opportunity to develop a prenatal diagnostic that obviates the risk associated with today's invasive diagnostics procedures. However, fetal cells are rare as compared to the presence of maternal cells in the blood. Therefore, any proposed analysis of fetal cells to diagnose fetal abnormalities requires enrichment of fetal cells. Enriching fetal cells from maternal peripheral blood is challenging, time intensive and any analysis derived therefrom is prone to error. The present invention addresses these challenges.

The present invention relates to methods for determining the presence of fetal cells and fetal abnormalities when fetal cells are present in a mixed sample (e.g. maternal blood sample). In some embodiments, determining the presence of fetal cells or of a fetal abnormality includes comparing the level of genomic DNA from a mixed sample to the level of genomic DNA in a control sample. The control or reference sample can be a mixed sample that has been sufficiently diluted to be free of fetal cells. The mixed sample can contain at least one fetal cell and one non-fetal cell. In other embodiments, the sample comprises up to 50% fetal cells.

In some embodiments, determining the presence of fetal cells and/or abnormalities involves quantifying one or more regions of genomic DNA regions from the mixed sample and determining from the quantification the presence of a fetal abnormality. Preferably, such regions are polymorphic e.g. short tandem repeat (STR) regions.

Examples of fetal abnormalities that can be determined by quantifying regions on one or more chromosomes include trisomy 13, trisomy 18, trisomy 21 (Down Syndrome), Klinefelter Syndrome (XXY) and other irregular number of sex or autosomal chromosomes. Other examples of abnormal fetal genotypes that can be determined by quantifying regions on one or more chromosomes include, but are not limited to, aneuploidy such as, monosomy of one or more chromosomes (X chromosome monosomy, also known as Turner's syndrome), trisomy of one or more chromosomes (such as 13, 18, 21, and X), tetrasomy and pentasomy of one or more chromosomes (which in humans is most commonly observed in the sex chromosomes, e.g. XXXX, XXYY, XXXY, XYYY, XXXXX, XXXXY, XXXYY, XYYYY and XXYYY), triploidy (three of every chromosome, e.g. 69 chromosomes in humans), tetraploidy (four of every chromosome, e.g. 92 chromosomes in humans) and multiploidy. In some embodiments, an abnormal fetal genotype is a segmental aneuploidy. Examples of segmental aneuploidy include, but are not limited to, 1p36 duplication, dup(17) (p11.2p11.2) syndrome, Down syndrome, Pelizaeus-Merzbacher disease, dup(22)(q11.2q11.2) syndrome, and cat-eye syndrome. In some cases, an abnormal fetal genotype is due to one or more deletions of sex or autosomal chromosomes, which may result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azospermia (factor a), Azospermia (factor b), Azospermia (factor c), or 1p36 deletion. In some embodiments, a decrease in chromosomal number results in an XO syndrome.

Furthermore, the methods herein can distinguish maternal trisomy from paternal trisomy, and total aneuploidy from segmental aneuploidy. Segmental aneuploidies can be caused by an intra-chromosomal event such as a deletion, duplication or translocation event. Additionally, the methods herein can be used to identify monoploidy, triploidy, tetraploidy, pentaploidy and other higher multiples of the normal haploid state. In some embodiments, the maternal or paternal origin of the fetal abnormality can be determined.

The genomic DNA region(s) can be quantified by amplifying the regions using, for example, PCR, or preferably quantitative PCR. Alternatively, quantification of the regions can be achieved using capillary gel electrophoresis (CGE). In some embodiments, total genomic DNA is pre-amplified prior to the quantitative amplification step to increase the overall abundance of DNA. Such pre-amplification step can involve the use of multiple displacement amplification.

In some embodiments the genomic DNA regions quantified can be in one chromosome or in 2 or more chromosomes. The polymorphic regions can be quantified on either or both sex chromosomes X and Y, and on autosomal chromosomes including chromosomes 13, 18 and 21.

Prior to analysis a mixed sample suspected of having fetal cells (e.g. a maternal blood sample) can be enriched for fetal cells. Fetal cell enrichment can be accomplished using any method known in the art including size-based separation, affinity (e.g. magnetic) separation, FACS, laser microdissection, and magnetic bead separation. A mixed sample containing as few as 10 fetal cells can be enriched. In some embodiments, the fetal cells in the enriched sample constitute less than 50% of the total number of cells.

In some embodiments, the size-based separation method includes applying a mixed sample into a system that separates a first component of the mixed sample (e.g. fetal cells), which comprises cells that are larger than a critical size, in a first direction, and a second component of the mixed sample (e.g. enucleated maternal red blood cells), which comprises cells that are smaller than a critical size, towards a second exit port. The separation system can be a device that includes one or more arrays of obstacles that form a network of gaps.

In some embodiments, enrichment that is achieved by size-based separation is followed by one or more additional enrichment procedures including magnetic separation, fluorescence activated cell sorting (FACS), laser microdisection, and magnetic bead separation. In some embodiments, a sample enriched by size-based separation is subjected to affinity/magnetic separation and is further enriched for rare cells using fluorescence activated cell sorting (FACS) or selective lysis of a subset of the cells (e.g. fetal cells).

In some embodiments there are provided kits for detecting the fetal abnormalities wherein the kits include separation devices and the reagents needed to perform the genetic analysis. For example, the kit may include arrays for size based enrichment, a device for magnetic enrichment and reagents for performing PCR.

The methods can further comprise inputting the data from the quantification step into data model(s) for the association of DNA quantity with maternal and non-maternal alleles. The invention provides for a computer program product, which includes a computer executable logic recorded on a computer readable medium that can be used for diagnosing a fetal abnormality. The computer program is designed to receive data from one of more quantified DNA genomic regions from a mixed sample containing at least one fetal cell, determine the presence or absence of a fetal abnormality from the data, and generate an output that comprises the evaluation of the fetal abnormality. Methods for using the computer program product are also disclosed.

SUMMARY OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8A-8B illustrate cell smears of the product and waste fractions.

FIG. 12 illustrates a table with STR loci that can be used for fetal detection.

FIG. 13 illustrates a table with exemplary external primers for STR loci.

FIG. 14 illustrates a table with exemplary internal primers for STR loci.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention provides systems, apparatuses, and methods to detect the presence and condition (e.g. aneuploidy) of fetal cells in a mixed cell population, e.g. a sample wherein fetal cells consist of <50%, 45%, 40%, 35%, 30%, 25%, 20%, 15%, 10%, 5%, 1%, or 0.5% of all cells in a mixed sample.

Figure 1:
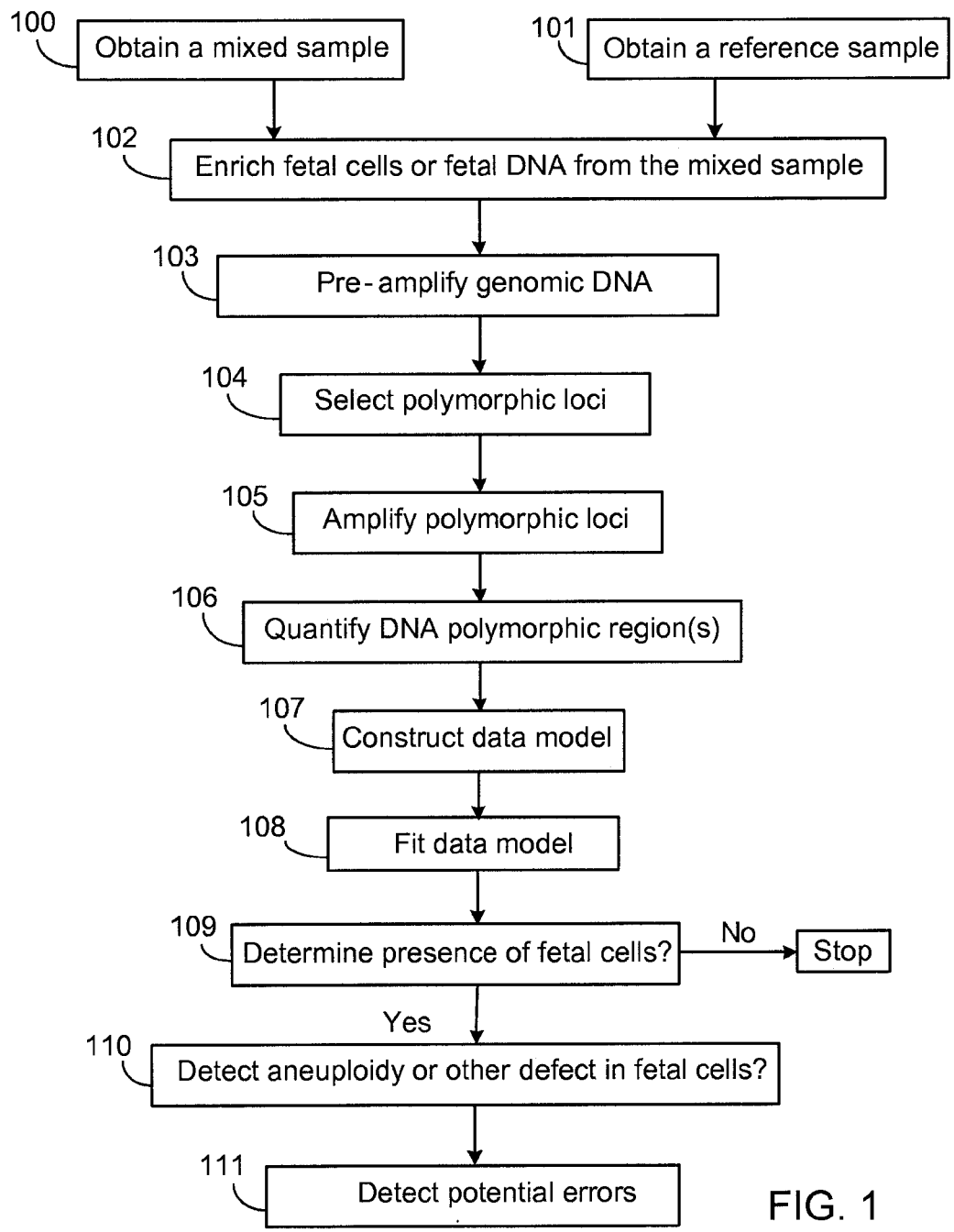
FIG. 1 illustrates a flow chart of one embodiment of the present invention.
Figure 2A:
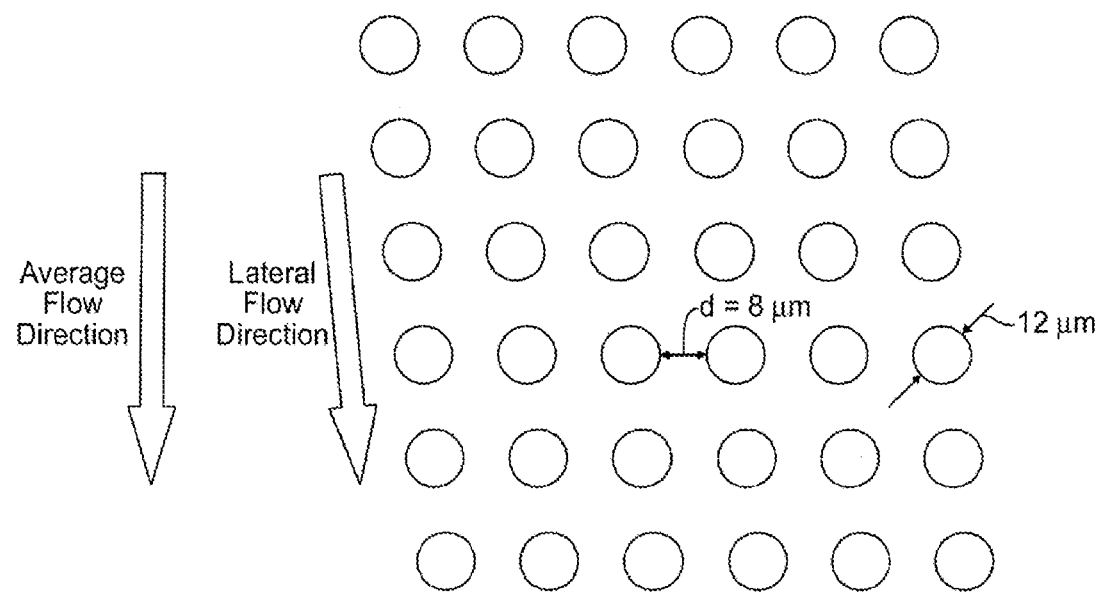
FIGS. 2A-2D illustrate one embodiment of a size-based separation module.
Figure 2B:
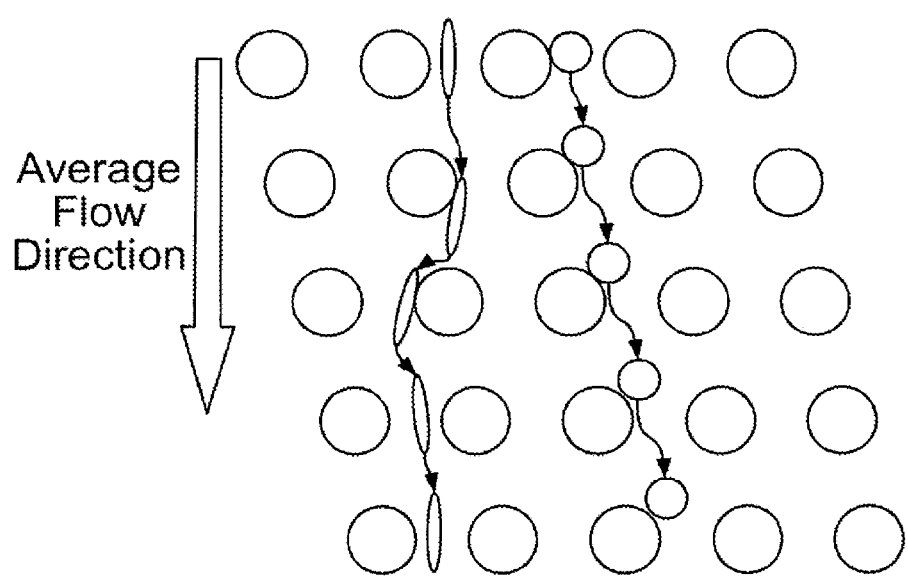
Figure 2C:
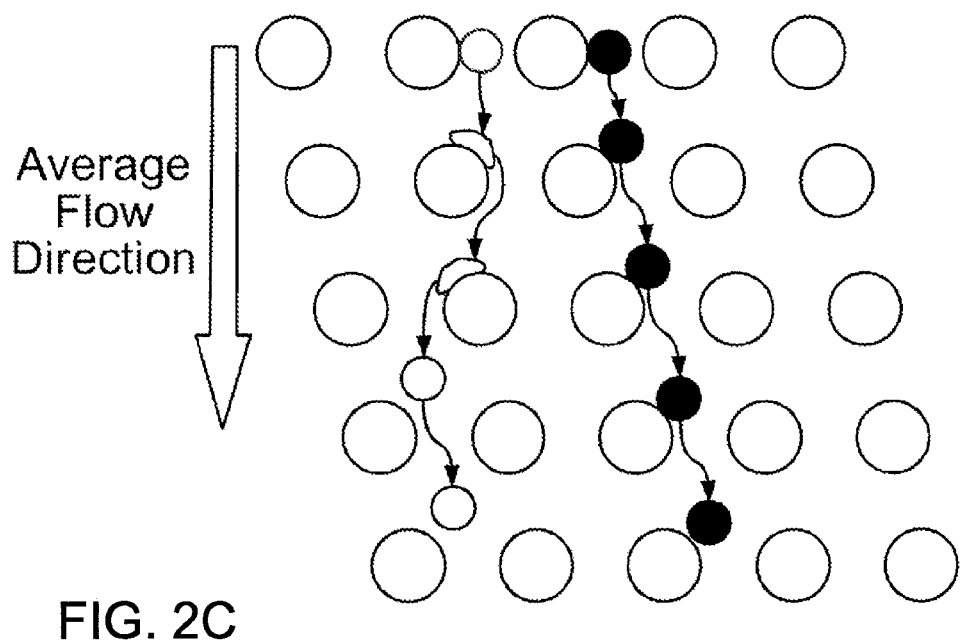
Figure 2D:
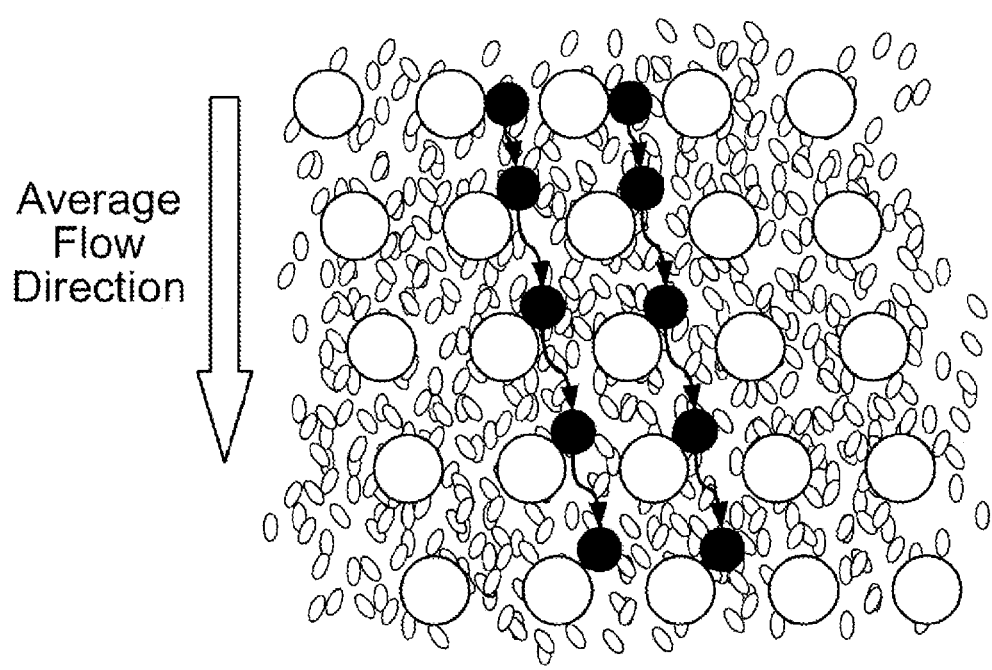

FIG. 1 illustrates an overview of one embodiment of the present invention.

In step 100, a sample containing (or suspected of containing) 1 or more fetal cells is obtained. Samples can be obtained from an animal suspected of being pregnant, pregnant, or that has been pregnant to detect the presence of a fetus or fetal abnormality. Such animal can be a human or a domesticated animal such as a cow, chicken, pig, horse, rabbit, dog, cat, or goat. Samples derived from an animal or human can include, e.g., whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid.

To obtain a blood sample, any technique known in the art may be used, e.g. a syringe or other vacuum suction device. A blood sample can be optionally pre-treated or processed prior to enrichment. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent.

When a blood sample is obtained, a preservative such an anti-coagulation agent and/or a stabilizer can be added to the sample prior to enrichment. This allows for extended time for analysis/detection. Thus, a sample, such as a blood sample, can be enriched and/or analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained.

In some embodiments, a blood sample can be combined with an agent that selectively lyses one or more cells or components in a blood sample. For example, fetal cells can be selectively lysed releasing their nuclei when a blood sample including fetal cells is combined with deionized water. Such selective lysis allows for the subsequent enrichment of fetal nuclei using, e.g., size or affinity based separation. In another example, platelets and/or enucleated red blood cells are selectively lysed to generate a sample enriched in nucleated cells, such as fetal nucleated red blood cells (fnRBC) and maternal nucleated blood cells (mnBC). The fnRBC's can subsequently be separated from the mnBC's using, e.g., affinity to antigen-i or magnetism differences in fetal and adult hemoglobin.

When obtaining a sample from an animal (e.g., blood sample), the amount can vary depending upon animal size, its gestation period, and/or the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

To detect fetal abnormality, a blood sample can be obtained from a pregnant animal or human within 36, 24, 22, 20, 18, 16, 14, 12, 10, 8, 6 or 4 weeks of gestation.

In step 101, a reference sample is obtained. The reference sample consists of substantially all or all maternal cells. In some embodiments, a reference sample is a maternal blood sample enriched for white blood cells (WBC's) such that it consists of substantially all or all maternal WBC's. In some embodiments, a reference sample is a diluted mixed sample wherein the dilution results in a sample free of fetal cells. For example, a maternal blood sample of 10-50 ML can be diluted by at least 2, 5, 10, 20, 50, or 100 fold to reduce the likelihood that it will include fetal cells.

In step 102, when the sample to be tested or analyzed is a mixed sample (e.g. maternal blood sample), it is enriched for rare cells or rare DNA (e.g. fetal cells, fetal DNA or fetal nuclei) using one or more methods known in the art or disclosed herein. Such enrichment increases the ratio of fetal cells to non-fetal cells; the concentration of fetal DNA to non-fetal DNA; or the concentration of fetal cells in volume per total volume of the mixed sample.

In some embodiments, enrichment occurs by selective lysis as described above. For example, enucleated cells may be selectively lysed prior to subsequent enrichment steps or fetal nucleated cells may be selectively lysed prior to separation of the fetal nuclei from other cells and components in the sample.

In some embodiments, enrichment of fetal cells or fetal nuclei occurs using one or more size-based separation modules. Size-based separation modules include filtration modules, sieves, matrixes, etc., including those disclosed in International Publication Nos. WO 2004/113877, WO 2004/0144651, and US Application Publication No. 2004/011956.

In some embodiments, a size-based separation module includes one or more arrays of obstacles that form a network of gaps. The obstacles are configured to direct particles (e.g. cells or nuclei) as they flow through the array/network of gaps into different directions or outlets based on the particle's hydrodynamic size. For example, as a blood sample flows through an array of obstacles, nucleated cells or cells having a hydrodynamic size larger than a critical size, e.g., 8 microns, are directed to a first outlet located on the opposite side of the array of obstacles from the fluid flow inlet, while the enucleated cells or cells having a hydrodynamic size smaller than a critical size, e.g., 8 microns, are directed to a second outlet also located on the opposite side of the array of obstacles from the fluid flow inlet.

An array can be configured to separate cells smaller than a critical size from those larger than the critical size by adjusting the size of the gaps, obstacles, and offset in the period between each successive row of obstacles. For example, in some embodiments, obstacles and/or gaps between obstacles can be up to 10, 20, 50, 70, 100, 120, 150, 170, or 200 microns in length or about 2, 4, 6, 8 or 10 microns in length. In some embodiments, an array for size-based separation includes more than 100, 500, 1,000, 5,000, 10,000, 50,000 or 100,000 obstacles that are arranged into more than 10, 20, 50, 100, 200, 500, or 1000 rows. Preferably, obstacles in a first row of obstacles are offset from a previous (upstream) row of obstacles by up to 50% of the period of the previous row of obstacles. In some embodiments, obstacles in a first row of obstacles are offset from a previous row of obstacles by up to 45, 40, 35, 30, 25, 20, 15 or 10% the period of the previous row of obstacles. Furthermore, the distance between a first row of obstacles and a second row of obstacles can be up to 10, 20, 50, 70, 100, 120, 150, 170 or 200 microns. A particular offset can be continuous (repeating for multiple rows) or non-continuous. In some embodiments, a separation module includes multiple discrete arrays of obstacles fluidly coupled such that they are in series with one another. Each array of obstacles has a continuous offset. But each subsequent (downstream) array of obstacles has an offset that is different from the previous (upstream) offset. Preferably, each subsequent array of obstacles has a smaller offset that the previous array of obstacles. This allows for a refinement in the separation process as cells migrate through the array of obstacles. Thus, a plurality of arrays can be fluidly coupled in series or in parallel, (e.g., more than 2, 4, 6, 8, 10, 20, 30, 40, 50). Fluidly coupling separation modules (e.g., arrays) in parallel allows for high-throughput analysis of the sample, such that at least 1, 2, 5, 10, 20, 50, 100, 200, or 500 mL per hour flows through the enrichment modules or at least 1, 5, 10, or 50 million cells per hour are sorted or flow through the device.

FIGS. 2A-2D illustrate one example of a size-based separation module. Obstacles (which may be of any shape) are coupled to a flat substrate to form an array of gaps. A transparent cover or lid may be used to cover the array. The obstacles form a two-dimensional array with each successive row shifted horizontally with respect to the previous row of obstacles, where the array of obstacles directs components having a hydrodynamic size smaller than a critical size in a first direction and components having a hydrodynamic size larger that a critical size in a second direction. See FIGS. 2B-2D. The flow of sample into the array of obstacles can be aligned at a small angle (flow angle) with respect to a line-of-sight of the array (lateral flow angle). Optionally, the array is coupled to an infusion pump to perfuse the sample through the obstacles. The flow conditions of the size-based separation module described herein are such that cells are sorted by the array with minimal damage. This allows for downstream analysis of intact cells and intact nuclei to be more efficient and reliable.

In one embodiment, a size-based separation module comprises an array of obstacles configured to direct rare cells larger than a critical size to migrate along a line-of-sight within the array towards a first outlet or bypass channel leading to a first outlet, while directing cells and analytes smaller than a critical size through the array of obstacles in a different direction towards a second outlet.

A variety of enrichment protocols may be utilized although gentle handling of the cells is preferred to reduce any mechanical damage to the cells or their DNA. This gentle handling also preserves the small number of fetal cells in the sample. Integrity of the nucleic acid being evaluated is an important feature in some embodiments to permit the distinction between the genomic material from the fetal cells and other cells in the sample. In particular, the enrichment and separation of the fetal cells using the arrays of obstacles produces gentle treatment which minimizes cellular damage and maximizes nucleic acid integrity permitting exceptional levels of separation and the ability to subsequently utilize various formats to very accurately analyze the genome of the cells which are present in the sample in extremely low numbers.

In some embodiments, enrichment of fetal cells occurs using one or more capture modules that selectively inhibit the mobility of one or more cells of interest. Preferably a capture module is fluidly coupled downstream to a size-based separation module. Capture modules can include a substrate having multiple obstacles that restrict the movement of cells or analytes greater than a critical size. Examples of capture modules that inhibit the migration of cells based on size are disclosed in U.S. Pat. Nos. 5,837,115 and 6,692,952.

In some embodiments, a capture module includes a two dimensional array of obstacles that selectively filters or captures cells or analytes having a hydrodynamic size greater than a particular gap size, e.g., critical sized. Arrays of obstacles adapted for separation by capture can include obstacles having one or more shapes and can be arranged in a uniform or non-uniform order. In some embodiments, a two-dimensional array of obstacles is staggered such that each subsequent row of obstacles is offset from the previous row of obstacles to increase the number of interactions between the analytes being sorted (separated) and the obstacles.

Another example of a capture module is an affinity-based separation module. An affinity-based separation module capture analytes or cells of interest based on their affinity to a structure or particle as oppose to their size. One example of an affinity-based separation module is an array of obstacles that are adapted for complete sample flow through, but for the fact that the obstacles are covered with binding moieties that selectively bind one or more analytes (e.g., cell population) of interest (e.g., red blood cells, fetal cells, or nucleated cells) or analytes not-of-interest (e.g., white blood cells). Binding moieties can include e.g., proteins (e.g., ligands/receptors), nucleic acids having complementary counterparts in retained analytes, antibodies, etc. In some embodiments, an affinity-based separation module comprises a two-dimensional array of obstacles covered with one or more antibodies selected from the group consisting of: anti-CD71, anti-CD235a, anti-CD36, anti-carbohydrates, anti-selectin, anti-CD45, anti-GPA, and anti-antigen-i.

Figure 3A:
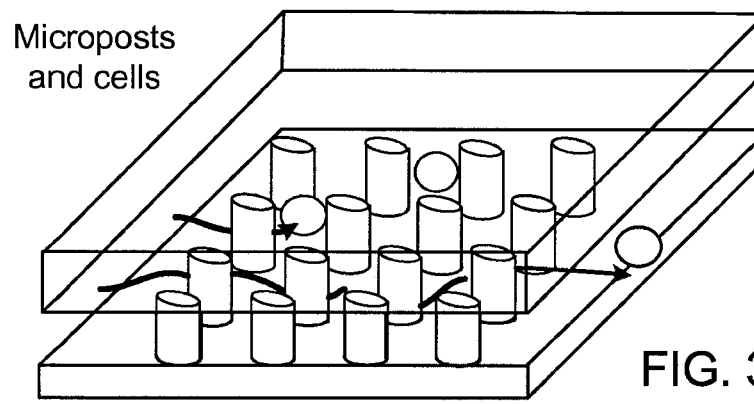
FIGS. 3A-3C illustrate one embodiment of an affinity separation module.
Figure 3B:
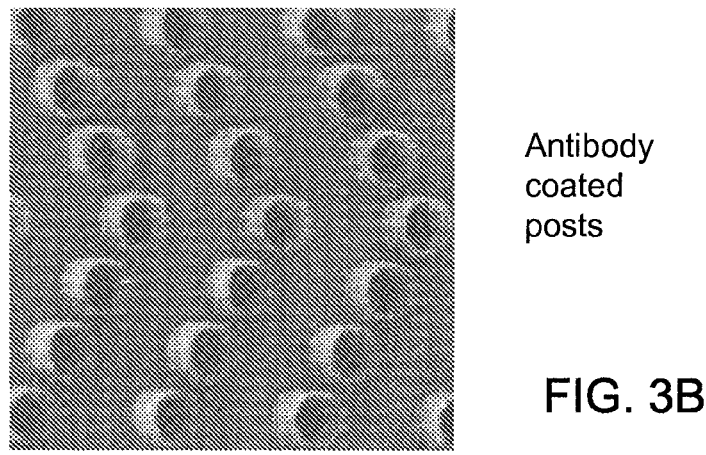
Figure 3C:
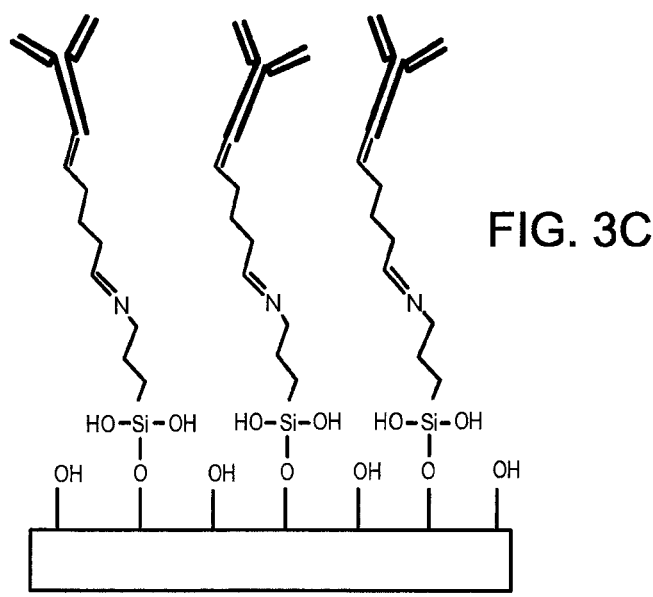

FIG. 3A illustrates a path of a first analyte through an array of posts wherein an analyte that does not specifically bind to a post continues to migrate through the array, while an analyte that does bind a post is captured by the array. FIG. 3B is a picture of antibody coated posts. FIG. 3C illustrates one method of coupling of antibodies to a substrate (e.g., obstacles, side walls, etc.) as contemplated by the present invention. Examples of such affinity-based separation modules are described in International Publication No. WO 2004/029221 and U.S. application Ser. No. 10/529,453, both of which are incorporated by reference.

In some embodiments, a capture module utilizes a magnetic field to separate and/or enrich one or more analytes (cells) that has a magnetic property or magnetic potential. For example, red blood cells which are slightly diamagnetic (repelled by magnetic field) in physiological conditions can be made paramagnetic (attributed by magnetic field) by deoxygenation of the hemoglobin into methemoglobin. This magnetic property can be achieved through physical or chemical treatment of the red blood cells. Thus, a sample containing one or more red blood cells and one or more non-red blood cells can be enriched for the red blood cells by first inducing a magnetic property and then separating the above red blood cells from other analytes using a magnetic field (uniform or non-uniform). For example, a maternal blood sample can flow first through a size-based separation module to remove enucleated cells and cellular components (e.g., analytes having a hydrodynamic size less than 6 μms) based on size. Subsequently, the enriched nucleated cells (e.g., analytes having a hydrodynamic size greater than 6 μms) white blood cells and nucleated red blood cells are treated with a reagent, such as $CO_2$, $N_2$ or $NaNO_2$, that changes the magnetic property of the red blood cells' hemoglobin. The treated sample then flows through a magnetic field (e.g., a column coupled to an external magnet), such that the paramagnetic analytes (e.g., red blood cells) will be captured by the magnetic field while the white blood cells and any other non-red blood cells will flow through the device to result in a sample enriched in nucleated red blood cells (including fnRBC's). Additional examples of magnetic separation modules are described in U.S. application Ser. No. 11/323,971, filed Dec. 29, 2005 entitled "Devices and Methods for Magnetic Enrichment of Cells and Other Particles" and U.S. application Ser. No. 11/227,904, filed Sep. 15, 2005, entitled "Devices and Methods for Enrichment and Alteration of Cells and Other Particles".

Subsequent enrichment steps can be used to separate the rare cells (e.g. fnRBC's) from the non-rare maternal nucleated red blood cells (non-RBC's). In some embodiments, a sample enriched by size-based separation followed by affinity/magnetic separation is further enriched for rare cells using fluorescence activated cell sorting (FACS) or selective lysis of a subset of the cells (e.g. fetal cells). In some embodiments, fetal cells are selectively bound to an anti-antigen i binding moiety (e.g. an antibody) to separate them from the mnRBC's. In some embodiments, the antibody binds to a fetal cell ligand. In some related embodiments the fetal cells are stimulated so as to induce expression of ligands which are targeted by an antibody. In some embodiments the fetal cells are lysed and the nuclei of the fetal cells are separated from other cellular components by binding them with an antibody. In some embodiments, fetal cells are selectively bound to receptors which target fetal cell ligands. In some embodiments, fetal cells are selectively bound to a lectin. In some embodiments, fetal cells or fetal DNA is distinguished from non-fetal cells or non-fetal DNA by forcing the rare cells (fetal cells) to become apoptotic, thus condensing their nuclei and optionally ejecting their nuclei. Rare cells such as fetal cells can be forced into apoptosis using various means including subjecting the cells to hyperbaric pressure (e.g. 4% $CO_2$). The condensed nuclei can be detected and/or isolated for further analysis using any technique known in the art including DNA gel electrophoresis, in situ labeling of DNA nicks (terminal deoxynucleotidyl transferase (TdT))-mediated dUTP in situ nick labeling (also known as TUNEL) (Gavrieli, Y., et al. J. Cell Biol 119:493-501 (1992)) and ligation of DNA strand breaks having one or two-base 3' overhangs (Taq polymerase-based in situ ligation). (Didenko V., et al. J. Cell Biol. 135:1369-76 (1996)).

In some embodiments, when the analyte desired to be separated (e.g., red blood cells or white blood cells) is not ferromagnetic or does not have a magnetic property, a magnetic particle (e.g., a bead) or compound (e.g., $Fe^{3+}$) can be coupled to the analyte to give it a magnetic property. In some embodiments, a bead coupled to an antibody that selectively binds to an analyte of interest can be decorated with an antibody elected from the group of anti CD71 or CD75. In some embodiments a magnetic compound, such as $Fe^{3+}$, can be couple to an antibody such as those described above. The magnetic particles or magnetic antibodies herein may be coupled to any one or more of the devices herein prior to contact with a sample or may be mixed with the sample prior to delivery of the sample to the device(s).

Magnetic field used to separate analytes/cells in any of the embodiments herein can uniform or non-uniform as well as external or internal to the device(s) herein. An external magnetic field is one whose source is outside a device herein (e.g., container, channel, obstacles). An internal magnetic field is one whose source is within a device contemplated herein. An example of an internal magnetic field is one where magnetic particles may be attached to obstacles present in the device (or manipulated to create obstacles) to increase surface area for analytes to interact with to increase the likelihood of binding. Analytes captured by a magnetic field can be released by demagnetizing the magnetic regions retaining the magnetic particles. For selective release of analytes from regions, the demagnetization can be limited to selected obstacles or regions. For example, the magnetic field can be designed to be electromagnetic, enabling turn-on and turn-off off the magnetic fields for each individual region or obstacle at will.

Figure 4:
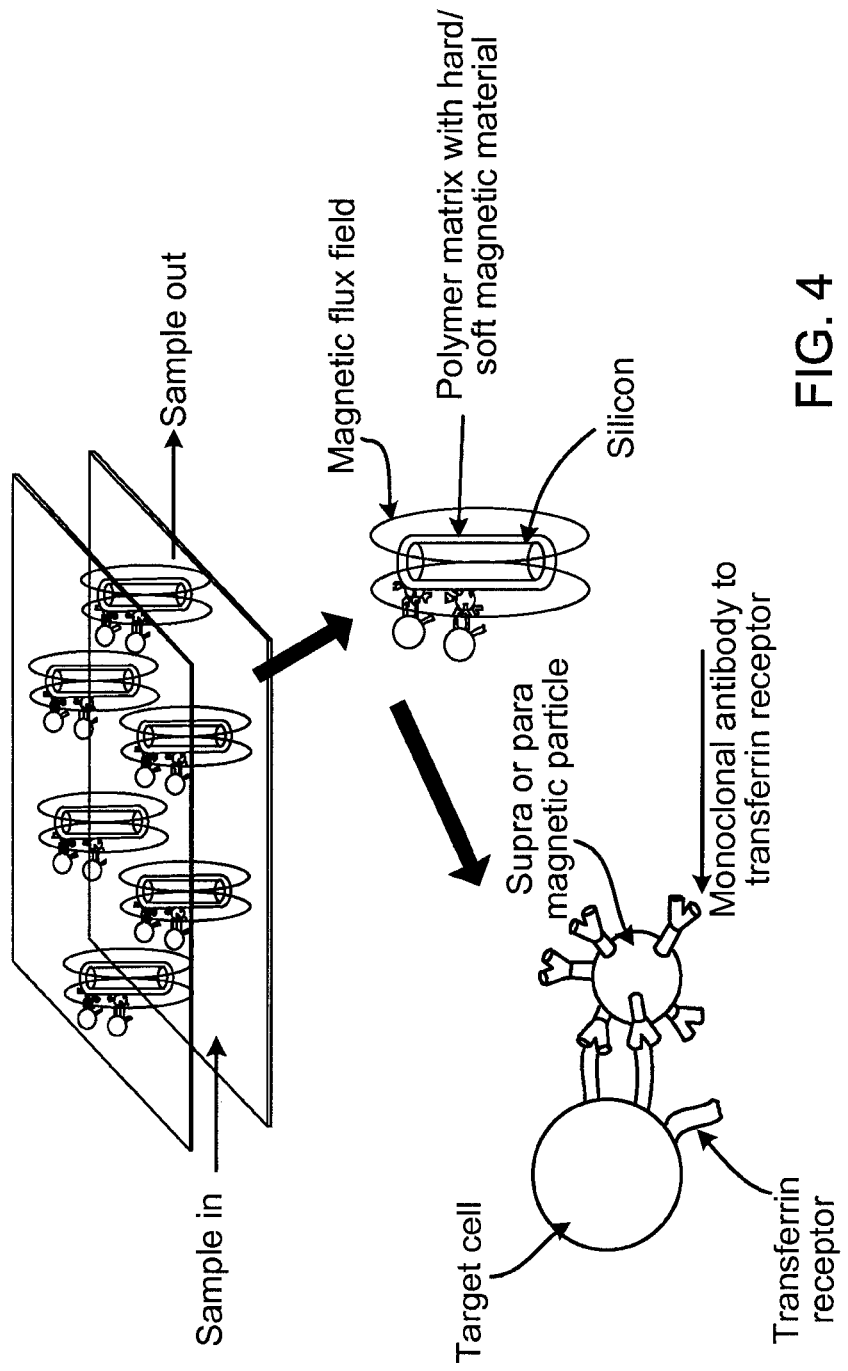
FIG. 4 illustrates one embodiment of a magnetic separation module.

FIG. 4 illustrates an embodiment of a device configured for capture and isolation of cells expressing the transferrin receptor from a complex mixture. Monoclonal antibodies to CD71 receptor are readily available off-the-shelf and can be covalently coupled to magnetic materials comprising any conventional ferroparticles, such as, but not limited to ferrous doped polystyrene and ferroparticles or ferro-colloids (e.g., from Miltenyi or Dynal). The anti CD71 bound to magnetic particles is flowed into the device. The antibody coated particles are drawn to the obstacles (e.g., posts), floor, and walls and are retained by the strength of the magnetic field interaction between the particles and the magnetic field. The particles between the obstacles and those loosely retained with the sphere of influence of the local magnetic fields away from the obstacles are removed by a rinse.

One or more of the enrichment modules herein (e.g., size-based separation module(s) and capture module(s)) may be fluidly coupled in series or in parallel with one another. For example a first outlet from a separation module can be fluidly coupled to a capture module. In some embodiments, the separation module and capture module are integrated such that a plurality of obstacles acts both to deflect certain analytes according to size and direct them in a path different than the direction of analyte(s) of interest, and also as a capture module to capture, retain, or bind certain analytes based on size, affinity, magnetism or other physical property.

In any of the embodiments herein, the enrichment steps performed have a specificity and/or sensitivity ≥50, 60, 70, 80, 90, 95, 96, 97, 98, 99, 99.1, 99.2, 99.3, 99.4, 99.5, 99.6, 99.7, 99.8, 99.9 or 99.95% The retention rate of the enrichment module(s) herein is such that ≥50, 60, 70, 80, 90, 91, 92, 93, 94, 95, 96, 97, 98, 99, or 99.9% of the analytes or cells of interest (e.g., nucleated cells or nucleated red blood cells or nucleated from red blood cells) are retained. Simultaneously, the enrichment modules are configured to remove ≥50, 60, 70, 80, 85, 90, 91, 92, 93, 94, 95, 96, 97, 98, 99, or 99.9% of all unwanted analytes (e.g., red blood-platelet enriched cells) from a sample.

Any or all of the enrichment steps can occur with minimal dilution of the sample. For example, in some embodiments the analytes of interest are retained in an enriched solution that is less than 50, 40, 30, 20, 10, 9.0, 8.0, 7.0, 6.0, 5.0, 4.5, 4.0, 3.5, 3.0, 2.5, 2.0, 1.5, 1.0, or 0.5 fold diluted from the original sample. In some embodiments, any or all of the enrichment steps increase the concentration of the analyte of interest (fetal cell), for example, by transferring them from the fluid sample to an enriched fluid sample (sometimes in a new fluid medium, such as a buffer). The new concentration of the analyte of interest may be at least 2, 4, 6, 8, 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 50,000,000, 100,000,000, 200,000,000, 500,000,000, 1,000,000,000, 2,000,000,000, or 5,000,000,000 fold more concentrated than in the original sample. For example, a 10 times concentration increase of a first cell type out of a blood sample means that the ratio of first cell type/all cells in a sample is 10 times greater after the sample was applied to the apparatus herein. Such concentration can take a fluid sample (e.g., a blood sample) of greater than 10, 15, 20, 50, or 100 mL total volume comprising rare components of interest, and it can concentrate such rare component of interest into a concentrated solution of less than 0.5, 1, 2, 3, 5, or 10 mL total volume.

The final concentration of fetal cells in relation to non-fetal cells after enrichment can be about 1/10,000-1/10, or 1/1,000-1/100. In some embodiments, the concentration of fetal cells to maternal cells may be up to 1/1,000, 1/100, or 1/10 or as low as 1/100, 1/1,000 or 1/10,000.

Thus, detection and analysis of the fetal cells can occur even if the non-fetal (e.g. maternal) cells are >50%, 60%, 70%, 80%, 90%, 95%, or 99% of all cells in a sample. In some embodiments, fetal cells are at a concentration of less than 1:2, 1:4, 1:10, 1:50, 1:100, 1:1000, 1:10,000, 1:100,000, 1,000,000, 1:10,000,000 or 1:100,000,000 of all cells in a mixed sample to be analyzed or at a concentration of less than $1\times10^{-3}$, $1\times10^{-4}$, $1\times10^{-5}$, $1\times10^{-6}$, or $1\times10^{-6}$ cells/µL of the mixed sample. Over all, the number of fetal cells in a mixed sample, (e.g. enriched sample) has up to 1, 2, 3, 4, 5, 6, 7, 8, 9, 10, 15, 20, 30, 40, 50, 100 total fetal cells.

Figure 24:
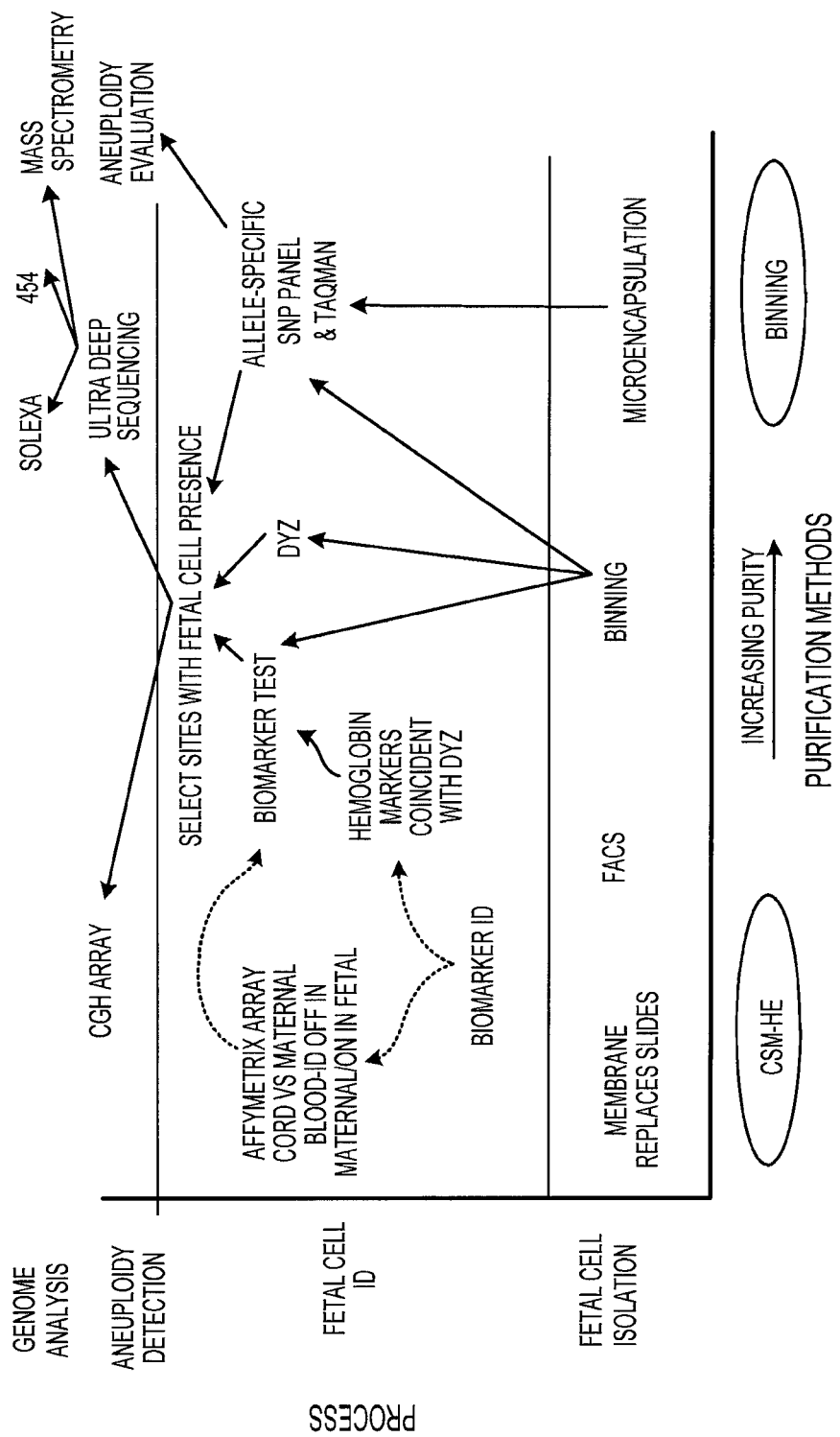
FIG. 24 illustrates methods of fetal diagnostic assays. Fetal cells are isolated by CSM-HE enrichment of target cells from blood. The designation of the fetal cells may be confirmed using techniques comprising FISH staining (using slides or membranes and optionally an automated detector), FACS, and/or binning. Binning may comprise distribution of enriched cells across wells in a plate (such as a 96 or 384 well plate), microencapsulation of cells in droplets that are separated in an emulsion, or by introduction of cells into microarrays of nanofluidic bins. Fetal cells are then identified using methods that may comprise the use of biomarkers (such as fetal (gamma) hemoglobin), allele-specific SNP panels that could detect fetal genome DNA, detection of differentially expressed maternal and fetal transcripts (such as Affymetrix chips), or primers and probes directed to fetal specific loci (such as the multi-repeat DYZ locus on the Y-chromosome). Binning sites that contain fetal cells are then be analyzed for aneuploidy and/or other genetic defects using a technique such as CGH array detection, ultra deep sequencing (such as Solexa, 454 or mass spectrometry), STR analysis, or SNP detection.
Figure 25:
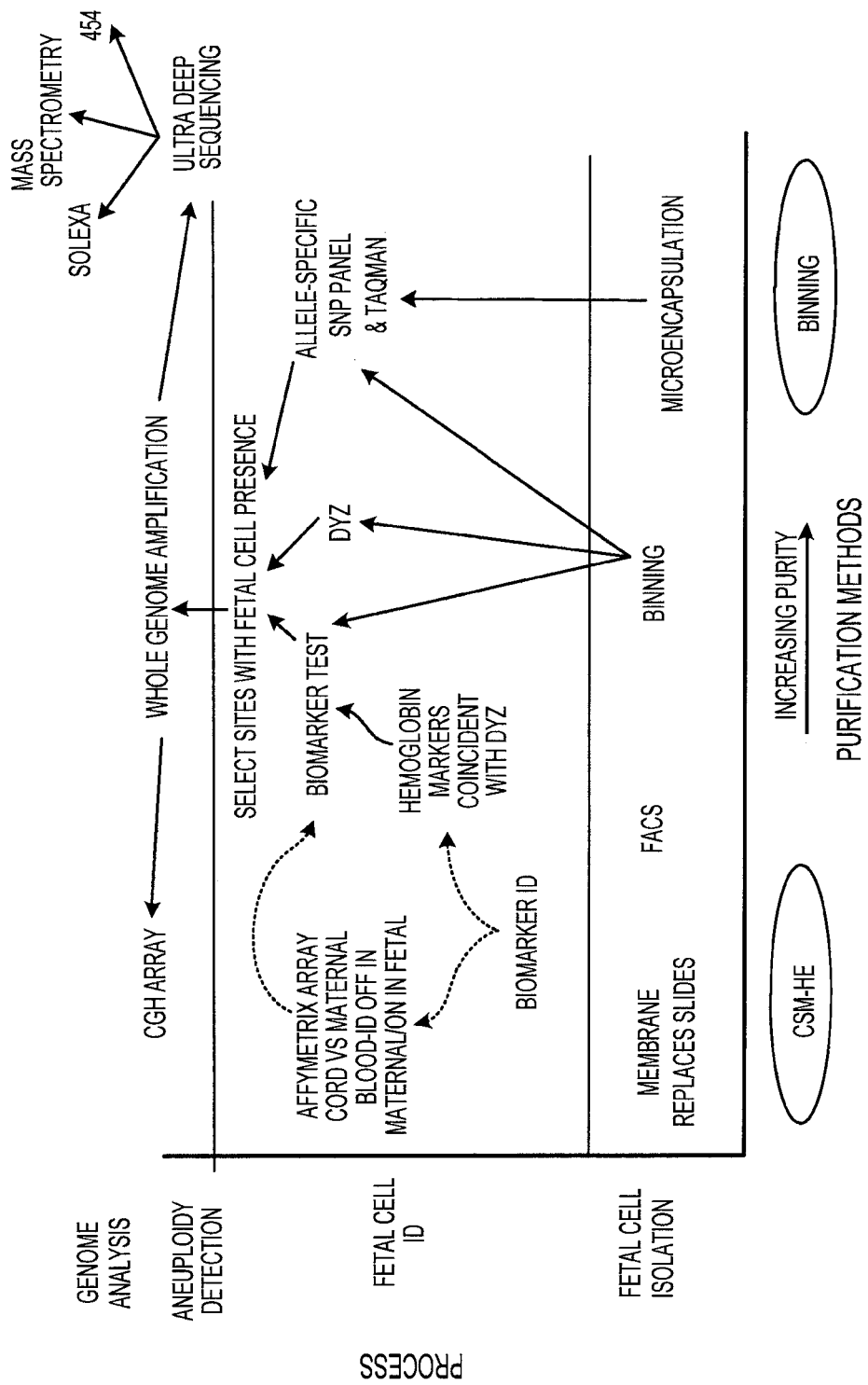
FIG. 25 illustrates methods of fetal diagnostic assays, further comprising the step of whole genome amplification prior to analysis of aneuploidy and/or other genetic defects.

Enriched target cells (e.g., fnRBC) may be "binned" prior to further analysis of the enriched cells (FIGS. 24 and 25). Binning is any process which results in the reduction of complexity and/or total cell number of the enriched cell output. Binning may be performed by any method known in the art or described herein. One method of binning is by serial dilution. Such dilution may be carried out using any appropriate platform (e.g., PCR wells, microtiter plates) and appropriate buffers. Other methods include nanofluidic systems which can separate samples into droplets (e.g., BioTrove, Raindance, Fluidigm). Such nanofluidic systems may result in the presence of a single cell present in a nanodroplet.

Binning may be preceded by positive selection for target cells including, but not limited to, affinity binding (e.g. using anti-CD71 antibodies). Alternately, negative selection of non-target cells may precede binning. For example, output from a size-based separation module may be passed through a magnetic hemoglobin enrichment module (MHEM) which selectively removes WBCs from the enriched sample by attracting magnetized hemoglobin-containing cells.

For example, the possible cellular content of output from enriched maternal blood which has been passed through a size-based separation module (with or without further enrichment by passing the enriched sample through a MHEM) may consist of: 1) approximately 20 fnRBC; 2) 1,500 nmRBC; 3) 4,000-40,000 WBC; 4) $15\times10^6$ RBC. If this sample is separated into 100 bins (PCR wells or other acceptable binning platform), each bin would be expected to contain: 1) 80 negative bins and 20 bins positive for one fnRBC; 2) 150 nmRBC; 3) 400-4,000 WBC; 4) $15\times10^4$ RBC. If separated into 10,000 bins, each bin would be expected to contain: 1) 9,980 negative bins and 20 bins positive for one fnRBC; 2) 8,500 negative bins and 1,500 bins positive for one mnRBC; 3) <1-4 WBC; 4) $15\times10^2$ RBC. One of skill in the art will recognize that the number of bins may be increased or decreased depending on experimental design and/or the platform used for binning. Reduced complexity of the binned cell populations may facilitate further genetic and/or cellular analysis of the target cells by reducing the number of non-target cells in an individual bin.

Analysis may be performed on individual bins to confirm the presence of target cells (e.g. fnRBC) in the individual bin. Such analysis may consist of any method known in the art including, but not limited to, FISH, PCR, STR detection, SNP analysis, biomarker detection, and sequence analysis (FIGS. 24 and 25).

Fetal Biomarkers

In some embodiments fetal biomarkers may be used to detect and/or isolate fetal cells, after enrichment or after detection of fetal abnormality or lack thereof. For example, this may be performed by distinguishing between fetal and maternal nRBCs based on relative expression of a gene (e.g., DYS1, DYZ, CD-71, ε- and ξ-globin) that is differentially expressed during fetal development. In preferred embodiments, biomarker genes are differentially expressed in the first and/or second trimester. "Differentially expressed," as applied to nucleotide sequences or polypeptide sequences in a cell or cell nuclei, refers to differences in over/under-expression of that sequence when compared to the level of expression of the same sequence in another sample, a control or a reference sample. In some embodiments, expression differences can be temporal and/or cell-specific. For example, for cell-specific expression of biomarkers, differential expression of one or more biomarkers in the cell(s) of interest can be higher or lower relative to background cell populations. Detection of such difference in expression of the biomarker may indicate the presence of a rare cell (e.g., fnRBC) versus other cells in a mixed sample (e.g., background cell populations). In other embodiments, a ratio of two or more such biomarkers that are differentially expressed can be measured and used to detect rare cells.

In one embodiment, fetal biomarkers comprise differentially expressed hemoglobins. Erythroblasts (nRBCs) are very abundant in the early fetal circulation, virtually absent in normal adult blood and by having a short finite lifespan, there is no risk of obtaining fnRBC which may persist from a previous pregnancy. Furthermore, unlike trophoblast cells, fetal erythroblasts are not prone to mosaic characteristics.

Yolk sac erythroblasts synthesize ε-, ξ-, γ- and α-globins, these combine to form the embryonic hemoglobins. Between six and eight weeks, the primary site of erythropoiesis shifts from the yolk sac to the liver, the three embryonic hemoglobins are replaced by fetal hemoglobin (HbF) as the predominant oxygen transport system, and ε- and ξ-globin production gives way to γ-, α- and β-globin production within definitive erythrocytes (Peschle et al., 1985). HbF remains the principal hemoglobin until birth, when the second globin switch occurs and β-globin production accelerates.

Hemoglobin (Hb) is a heterodimer composed of two identical α globin chains and two copies of a second globin. Due to differential gene expression during fetal development, the composition of the second chain changes from ε globin during early embryonic development (1 to 4 weeks of gestation) to γ globin during fetal development (6 to 8 weeks of gestation) to β globin in neonates and adults as illustrated in (Table 1).

TABLE 1

Relative expression of ε, γ and β in maternal and fetal RBCs.

| | | ε | γ | B |
|---|---|---|---|---|
| 1st trimester | Fetal | ++ | ++ | − |
| | Maternal | − | +/− | ++ |
| 2nd trimester | Fetal | − | ++ | +/− |
| | Maternal | − | +/− | ++ |

In the late-first trimester, the earliest time that fetal cells may be sampled by CVS, fnRBCs contain, in addition to α globin, primarily ε and γ globin. In the early to mid second trimester, when amniocentesis is typically performed, fnRBCs contain primarily γ globin with some adult β globin. Maternal cells contain almost exclusively α and β globin, with traces of γ detectable in some samples. Therefore, by measuring the relative expression of the ε, γ and β genes in RBCs purified from maternal blood samples, the presence of fetal cells in the sample can be determined. Furthermore, positive controls can be utilized to assess failure of the FISH analysis itself.

In various embodiments, fetal cells are distinguished from maternal cells based on the differential expression of hemoglobins β, γ or ε. Expression levels or RNA levels can be determined in the cytoplasm or in the nucleus of cells. Thus in some embodiments, the methods herein involve determining levels of messenger RNA (mRNA), ribosomal RNA (rRNA), or nuclear RNA (nRNA).

In some embodiments, identification of fnRBCs can be achieved by measuring the levels of at least two hemoglobins in the cytoplasm or nucleus of a cell. In various embodiments, identification and assay is from 1, 2, 3, 4, 5, 6, 7, 8, 9, 10, 15 or 20 fetal nuclei. Furthermore, total nuclei arrayed on one or more slides can number from about 100, 200, 300, 400, 500, 700, 800, 5000, 10,000, 100,000, 1,000,000, 2,000,000 to about 3,000,000. In some embodiments, a ratio for γ/β or ε/β is used to determine the presence of fetal cells, where a number less than one indicates that a fnRBC(s) is not present. In some embodiments, the relative expression of γ/β or ε/β provides a fnRBC index ("FNI"), as measured by γ or ε relative to β. In some embodiments, a FNI for γ/β greater than 5, 10, 15, 20, 25, 30, 35, 40, 45, 90, 180, 360, 720, 975, 1020, 1024, 1250 to about 1250, indicate that a fnRBC(s) is present. In yet other embodiments, a FNI for γ/β of less than about 1 indicates that a fnRBC(s) is not present. Preferably, the above FNI is determined from a sample obtained during a first trimester. However, similar ratios can be used during second trimester and third trimester.

In some embodiments, the expression levels are determined by measuring nuclear RNA transcripts including, nascent or unprocessed transcripts. In another embodiment, expression levels are determined by measuring mRNA, including ribosomal RNA. There are many methods known in the art for imaging (e.g., measuring) nucleic acids or RNA including, but not limited to, using expression arrays from Affymetrix, Inc. or Illumina, Inc.

RT-PCR primers can be designed by targeting the globin variable regions, selecting the amplicon size, and adjusting the primers annealing temperature to achieve equal PCR amplification efficiency. Thus TaqMan probes can be designed for each of the amplicons with well-separated fluorescent dyes, Alexa fluor®-355 for ε, Alexa Fluor®-488 for γ, and Alexa Fluor-555 for β. The specificity of these primers can be first verified using ε, γ, and β cDNA as templates. The primer sets that give the best specificity can be selected for further assay development. As an alternative, the primers can be selected from two exons spanning an intron sequence to amplify only the mRNA to eliminate the genomic DNA contamination.

The primers selected can be tested first in a duplex format to verify their specificity, limit of detection, and amplification efficiency using target cDNA templates. The best combinations of primers can be further tested in a triplex format for its amplification efficiency, detection dynamic range, and limit of detection.

Various commercially available reagents are available for RT-PCR, such as One-step RT-PCR reagents, including Qiagen One-Step RT-PCR Kit and Applied Biosytems TaqMan One-Step RT-PCR Master Mix Reagents kit. Such reagents can be used to establish the expression ratio of ε, γ, and β using purified RNA from enriched samples. Forward primers can be labeled for each of the targets, using Alexa fluor-355 for ε, Alexa fluor-488 for γ, and Alexa fluor-555 for β. Enriched cells can be deposited by cytospinning onto glass slides. Additionally, cytospinning the enriched cells can be performed after in situ RT-PCR. Thereafter, the presence of the fluorescent-labeled amplicons can be visualized by fluorescence microscopy. The reverse transcription time and PCR cycles can be optimized to maximize the amplicon signal:background ratio to have maximal separation of fetal over maternal signature. Preferably, signal:background ratio is greater than 5, 10, 50 or 100 and the overall cell loss during the process is less than 50, 10 or 5%.

Fetal Cell Analysis

The detection and analysis steps may involve quantifying genomic DNA regions from cells in a sample or enriched sample. In some embodiments, the quantified genomic DNA regions are polymorphic sites such as short tandem repeats (STRs) or variable number of tandem repeats (VNTRs).

In step 103, polymorphic genomic DNA region(s) or whole genome(s) from the mixed sample and optionally reference sample are pre-amplified to increase the overall abundance of DNA used for quantification and analysis. Pre-amplification can be preformed using multiple displacement amplification (MDA) (Gonzalez et al. Envircon Microbiol; 7(7); 1024-8 (2005)) or amplification with outer primers in a nested PCR approach. This permits detection and analysis of fetal DNA even if the total amount of fetal DNA in the mixed (e.g. enriched) sample is only up to 1 µg, 500 ng, 200 ng, 100 ng, 50 ng, 40 ng, 30 ng, 20 ng, 10 ng, 5 ng, 1 ng, 500 pg, 200 pg, 100 pg, 50 pg, 40 pg, 30 pg, 20 p, 10 pg, 5 pg, or 1 pg or between 1-5 µg, 5-10 µg, or 10-50 µg. Pre-amplification allows the products to be split into multiple reactions at the next step.

In step 104, polymorphic DNA region(s) such as short tandem repeats (STRs) or variable number of tandem repeats (VNTRs) are selected on suspected trisomic chromosome(s) (e.g., 13, 18, 21, X or Y) or chromosome(s) associated with a condition to be detected and optionally on control (non-trisomic) chromosomes. In some embodiments, 1 or more than 1, 2, 3, 4, 5, 6, 7, 8, 9, 10, 15, 20 DNA polymorphic loci are selected per target chromosome. Multiple polymorphic regions can be analyzed independently or at the same time in the same reaction. The polymorphic DNA regions, e.g. STRs loci, are selected for high heterozygosity (variety of alleles) so that the paternal allele of the fetal cells is more likely to be distinct in length from the maternal alleles. This results in an improved power to detect the presence of fetal cells in the mixed sample and potential fetal abnormalities in such cells. When the polymorphic regions selected are STR loci, di-, tri-, tetra- or penta-nucleotide repeat loci can be used for detection and analysis of fetal cells. Examples of STR loci that may be selected include: D21S1414, D21S1411, D21S1412, D21S11 MBP, D13S634, D13S631, D18S535, AmgXY, XHPRT, as well as those listed in FIG. 12. In some embodiment, the methods of the invention allow for the determination of maternal or paternal trisomy.

In step 105, the polymorphic loci selected are amplified. This can be used to detect non-maternal fetal alleles in the mixed sample and to determine the copy number of such alleles. When amplifying more than one polymorphic loci or DNA regions, primers are selected to be multiplexable (fairly uniform melting temperature, absence of cross-priming on the human genome, and absence of primer-primer interaction based on sequence analysis) with other primer pairs. Primers and loci are chosen so that the amplicon lengths from a given locus do not overlap with those from another locus.

In some embodiments, multiple dyes and multi-color fluorescence readout may be used to increase the multiplexing capacity, e.g. of a single CGE. This ensures that the loci are kept distinct in the readout (e.g. CGE readout). In such a case, PCR primer pairs can be grouped and the same end-labeling is applied to the members of a group.

Examples of primers known in the art that correspond to specific STR loci that can be used in the present invention are described in FIG. 13 and FIG. 14.

Examples of PCR techniques that can be used to amplify the DNA regions herein include, but are not limited to, quantitative PCR, quantitative fluorescent PCR (QF-PCR), multiplex fluorescent PCR (MF-PCR), real time PCR(RT-PCR), single cell PCR, restriction fragment length polymorphism PCR(PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that may be used to amplify specific polymorphic loci include those described in, U.S. Pat. Nos. 5,242, 794, 5,494,810, 4,988,617 and 6,582,938.

In step 106, the amplified DNA polymorphic regions (e.g. STR loci) from both mixed and reference samples are characterized and quantified using any method known in the art. Examples of such methods include, but are not limited to, gas chromatography, supercritical fluid chromatography, liquid chromatography, including partition chromatography, adsorption chromatography, ion exchange chromatography, size-exclusion chromatography, thin-layer chromatography, and affinity chromatography, electrophoresis, including capillary electrophoresis, capillary zone electrophoresis, capillary isoelectric focusing, capillary electrochromatography, micellar electrokinetic capillary chromatography, isotachophoresis, transient isotachophoresis and capillary gel electrophoresis, comparative genomic hybridization (CGH), microarrays, bead arrays, high-throughput genotyping technology, such as molecular inversion probe (MIP), and Genescan.

In one embodiment, capillary gel electrophoresis (CGE) is used to quantify STRs in both the mixed and reference samples. This can be used to detect non-maternal fetal alleles in the mixed sample and to determine the copy number of such alleles. The mixed sample and the reference sample can be analyzed in separate reactions, e.g. separate CGE lanes. Alternatively, the mixed and the reference sample can be run in the same reaction, e.g. same CGE lane, by using two different dye labels, e.g. differently labeled PCR primers. When a reference sample is run through the PCR/CGE process, the alleles show up as peaks in the CGE. It is desirable, but not essential, to associate these peaks with known alleles in the population at each locus. When performing PCR/CGE it may be very useful to reduce the non-linearities in the response of PCR to input DNA copies (i.e. to effect more quantitative PCR) so that the data can be more easily related to models of aneuploidy. This 'linearization' can be accomplished by the following procedure:

(a) The PCR reaction is initiated.
(b) The PCR reaction is interrupted after N cycles (N=5 to 10) and ~one third of the reaction products are removed and run on CGE. PCR cycling is re-initiated. Repeat until 40 PCR cycles or saturation is achieved.
(c) CGE peak masses are determined and normalized to correct for the depletion of the reaction products at each iteration of (b).
(d) A saturation (splining) curve is fit to the normalized data for each allele peak, and quantitative starting concentrations are inferred as in customary qPCR.

The above procedure tends to accomplish quantitative PCR while enabling a high degree of multiplexing. Because each CGE run has a slightly different relation between DNA fragment size (and sequence) and mobility, each trace typically will need to undergo a length transformation, such as a low-order (cubic or quartic) polynomial transformation, in order to map to the data from the trace corresponding to the previous amplification point. This mapping can be determined by adjusting the transformation parameters to achieve the best fit of the one data trace to the other, with both normalized to the same total sum of squares or summed peak heights.

The maternal peaks at each locus provide an estimate of the secondary 'stutter' structure at each locus due to PCR errors. The locations of these small secondary peaks can be used to blank out length regions that are contaminated by this stutter when looking for and using the non-maternal allele peaks (as described herein for example). Alternatively, more sophisticated 'deconvolution' algorithms can be applied to remove the stutter Stoughton, et al., *Electrophoresis;* 18(1): 1-S (1997).

The sample containing an unknown mixture of fetal and maternal cells is analyzed as in Step (b). This could be done in a separate CGE lane, or in the same CGE lane as the maternal sample by using two different dye labels on the PCR primers. Because each CGE trace has a slightly different relation between DNA fragment size (and sequence) and mobility, these data typically will need to undergo a length transformation, such as a low-order (cubic or quartic) polynomial transformation in order to map one trace onto the other to facilitate peak identification and model fitting. This mapping can be determined by adjusting the transformation parameters to achieve the best fit of the peak locations in one data trace to the other. This mapping will be well determined in the assumed situation where the maternal cells are more numerous than the fetal cells, because the maternal signature will dominate and will be shared in the two data sets.

Figure 5:
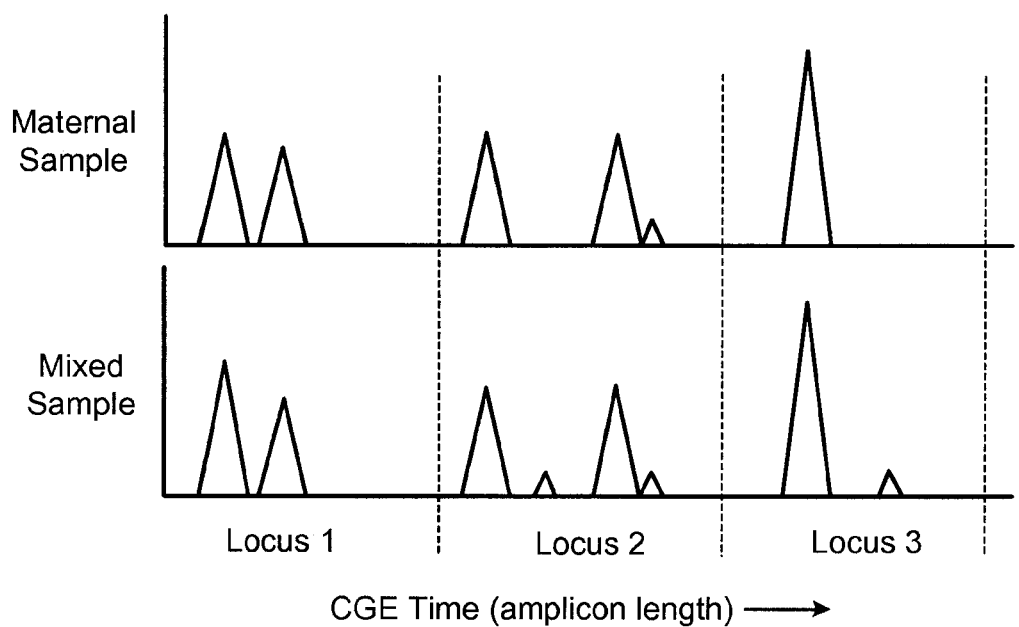
FIG. 5 illustrates typical locus patterns arising from a normal (diploid) fetus and mother.

FIG. 5 illustrates typical locus patterns arising from a normal (diploid) fetus and mother. At Locus 1, the paternal allele is the same as the left hand maternal allele, and adds to its apparent height. At Locus 2, the paternal allele has a length between the lengths of the maternal alleles. In addition, there is a secondary 'stutter' peak on the shoulder of the right hand maternal peak. In Locus 3, the maternal sample is homozygous leading to only one main peak, and the paternal allele is distinct from this allele.

Figure 6:
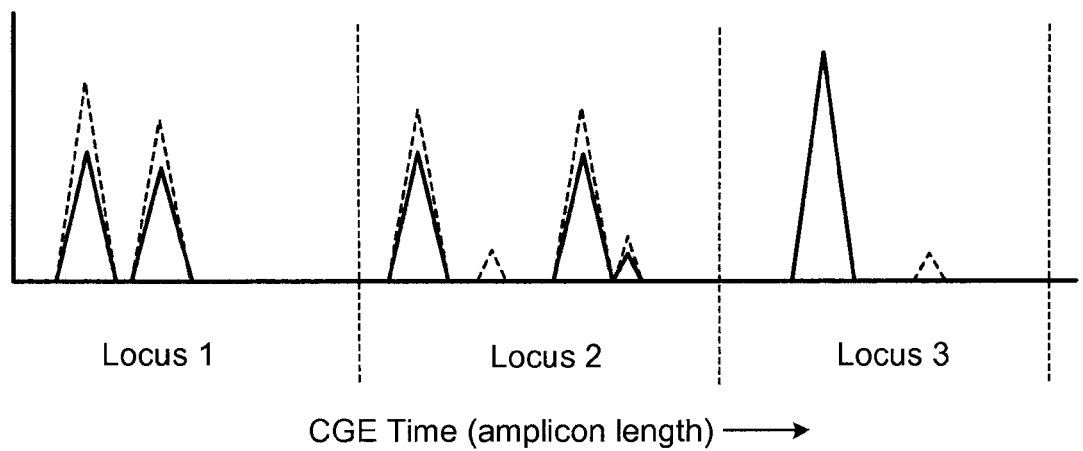
FIG. 6 illustrates typical locus patterns arising from trisomic fetal cells.
Figure 7A:
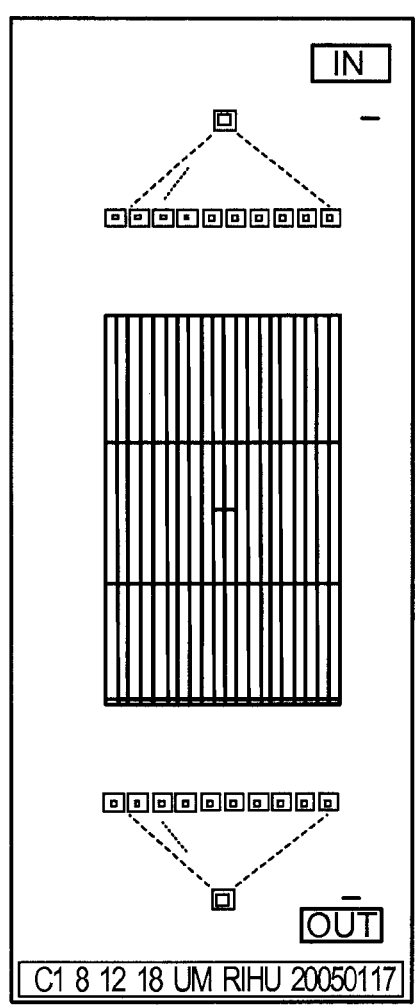
FIGS. 7A-7D illustrate various embodiments of a size-based separation module.
Figure 7B:
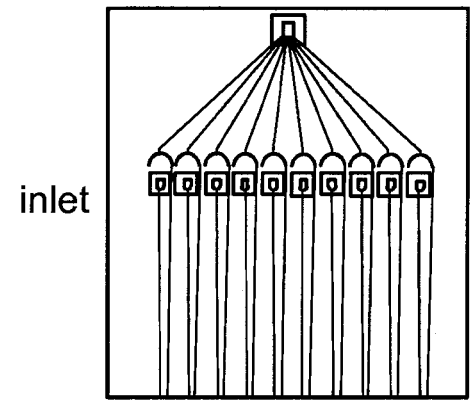
Figure 7C:
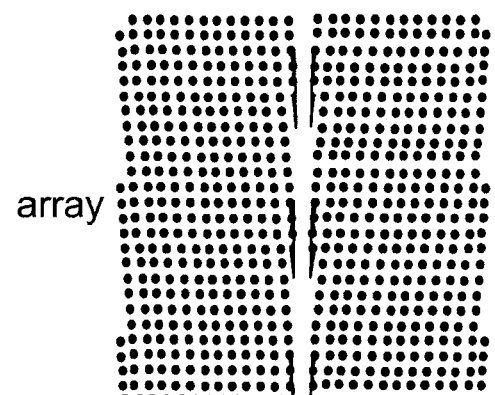
Figure 7D:
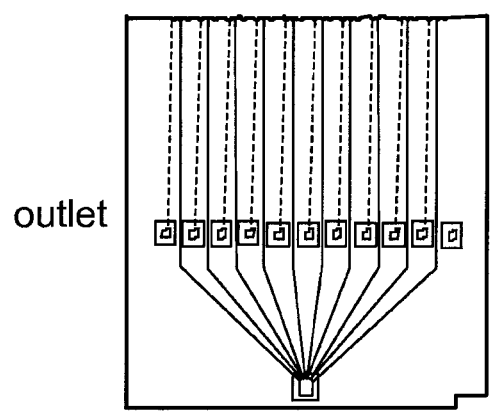
Figure 9A:
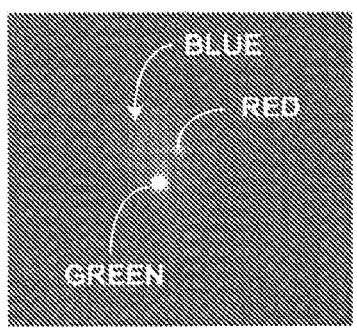
FIGS. 9A-9F illustrate isolated fetal cells confirmed by the reliable presence of male Y chromosome.
Figure 9B:
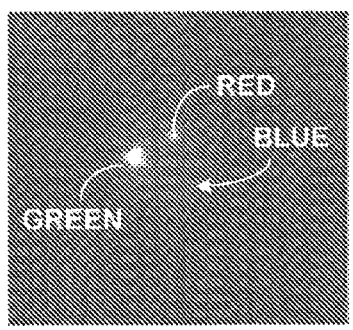
Figure 9C:
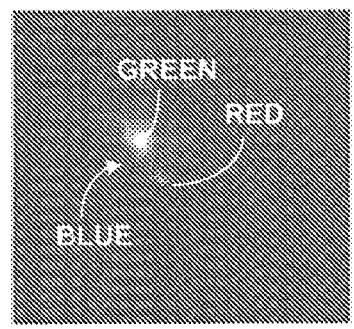
Figure 9D:
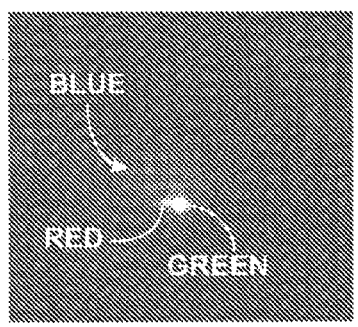
Figure 9E:
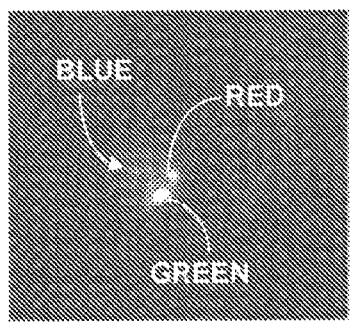
Figure 9F:
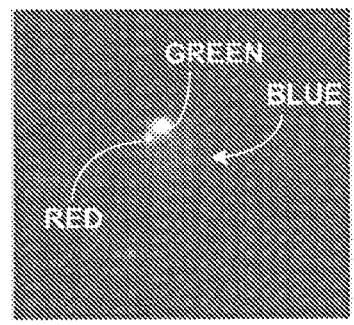

FIG. 6 illustrates locus patterns arising from trisomic fetal cells. The dashed trace represents mixed sample containing trisomic fetal cells, superposed on maternal sample trace (solid black). Trisomy causes excess amplitude in maternal alleles at loci contained within the aneuploid region (here assumed to contain Loci 1 and 2 but not Locus 3). The left hand maternal peak at Locus 1 contains contributions from the trisomy and from a paternal allele.

In step 107, data models are constructed. From the data obtained from the quantifying step different data models can be constructed depending upon different assumptions.

For example, a data model for the CGE patterns in FIGS. 5 and 6 can be as follows:

Let m1 denote the CGE signal obtained from one of the maternal alleles at a given locus and m2 the signal obtained from the other maternal allele, which might be the same allele. Let p denote the CGE signal obtained from the paternal allele at a given locus. Let p1 and p2 denote the CGE signals obtained from the paternal alleles at a given locus when a paternally derived trisomy occurs. Let □ α and β denote the relative number of maternal and fetal cells, respectively. Then in the case of a chromosome with maternal non-dysjunction trisomy, the data will have the form $$x = \alpha(\square m1 + m2) + \beta(m1 + m2 + p). \quad (1)$$

A normal (diploid) chromosome will give $$x = \alpha(m1 + m2) + \beta([m1 \text{ or } m2] + p), \quad (2)$$

and a paternally derived trisomy will give $$x = \alpha(m1 + m2) + \beta([m1 \text{ or } m2] + p1 + p2). \quad (3)$$

In some embodiments, data and data model is represented as discrete peak masses (or heights) and peak locations or as vectors of values representing the actual peak profiles. In the case of representation by peak characteristics, the 'addition' operation in Equations 1-3 denotes summation of peak height or mass at the discrete allele location. In the case where the full peak profiles are represented, summation denotes summation of signals bin by bin over the CGE trace, and in this case it may be helpful to zero the data except in the immediate vicinity of actual peaks. Representation via peak characteristics is preferable when using the PCR linearization technique described above.

To determine aneuploidy, the differences between the structure of the β-term that appears in the first and second equations above is determined. In the first case, there is an additional contribution to both maternal alleles along with the paternal allele, and in the second case there is an additional contribution only to one of the maternal alleles along with the paternal allele. The essence of the presence/absence declaration for fetal cells lies in the evidence for β being greater than zero.

In step 108, the best overall fit of model to data is selected from among all the model sets. This modeling approach optimally uses information contained in the increase of chromosome copy number with aneuploidy and its association with the strength of non-maternal alleles.

In some embodiments, CGE signals representing m1 and m2 at each locus are obtained by profiling the maternal-only sample and mapping the peak locations to the corresponding ones of the mixed sample. The heights of m1 and m2 may be unequal, and this helps correct for PCR amplification biases associated with particular alleles. The values of p, p1, p2, α, and β are determined from the mixed sample data by fitting Equations 1-3 to the data, optionally by using the least squares, or the maximum likelihood methods.

The three models need to be fit to each chromosome with suspected trisomy, e.g. chromosomes 13, 18, 21, X and/or Y. If there are only 3 suspected chromosomes, this results in 27 model variants (3×3×3=27). In Equations 2 and 3, there is also the ambiguity between using m1 or m2 in the β-term, so there are 5 model variants for each chromosome, with 5×5×5=125 total variants over three suspected trisomy chromosomes.

Segmental aneuploidies also could be tested by hypothesizing that different contiguous subsets of loci are contained within the aneuploid region. With each model variant, α and β have to be determined and the parameters describing the paternal alleles have to be determined at each locus for each model variant. The paternal allele peak height and shape can be assumed to be an average of the known maternal ones at that locus, while the paternal allele location needs to be fit to the data. The possible locations for the paternal allele will be the location of m1, the location of m2, and 'elsewhere in the locus window' where this latter possibility involves a search over discrete shifts smaller than a typical peak half-width at half maximum. Prior probabilities on the choices of p, taken from population allele frequency data, can be used, if their product lengths can be predicted.

In some cases, because of the number of parameters being fit, suboptimal searches can be used for computational efficiency. For example, one possible approach involves iterative methods, such as the following, which would be applied to each data model variant:

(i) Set β to 0 and solve for α.
(ii) Set β to a value where β/α is the smallest fetal/maternal cell ratio for which fetal cells are likely to be detectable.
(iii) Solve for paternal allele location(s) at each locus, one locus at a time that minimize data-model residuals.
(iv) Fix the paternal allele parameters and adjust β to minimize residuals over all the data.
(v) Now vary only α to minimize residuals.

(vi) Repeat iv and v until convergence.

(vii) Repeat iii through v until convergence.

In step 109, the presence or absence of fetal DNA is determined using the models described above. The best overall fit for such models yields the values of β, α that can be called $B_{max}$□, $α_{max}$. The likelihood of observing the data given $β_{max}$ can be compared to the likelihood given β=0. The ratio is a measure of the amount of evidence for fetal DNA. A threshold for declaring fetal DNA is the likelihood ratio of approximately 1000 or more. The likelihood calculation can be approximated by a Chi-squared calculation involving the sum of squared residuals between the data and the model, where each residual is normalized by the expected rms error.

If it is determined that fetal DNA is not present in the mixed sample as calculated above, then the test is declared to be non-informative. On the other hand, if it is decided that fetal DNA is present in the mixed sample, then the likelihoods of the data given the different data model types can be compared to declare trisomy or another condition.

In step 110, the likelihood ratios of trisomy models (Equations 1 and 3) to the normal model (Equation 2) are calculated and these ratios are compared to a predefined threshold. This threshold can be set so that in controlled tests all the trisomic cases are declared aneuploid, and so that it is expected that the vast majority (>99.9%) of all truly trisomic cases are declared aneuploid by the test. In one embodiment, to accomplish a detection rate of >90% or 95% or approximately 99.9%, the likelihood ratio threshold is increased beyond what is necessary to declare all the known trisomic cases in the validation set by a factor of 1000/N, where N is the number of trisomy cases in the validation set.

In step 111, errors that may arise from the experimental procedure used to obtain the data can be taken into account in the model calculation(s). For instance, in the example described above, CGE data contain small additive errors associated with CGE readout, and larger multiplicative errors associated with PCR amplification efficiencies being different from locus to locus and from allele to allele within a locus. By using the maternal-only data to define m1 and m2 peak characteristics at each locus, the effects of PCR amplification biases associated with different primers and different amplicons from the same primers have been mostly controlled. Nevertheless, small variations in the process from day to day and the statistics of small numbers of starting genome copies will cause some random errors to remain. These tend to be multiplicative errors in the resulting CGE peak heights; e.g. two peaks may be 20% different in height although the starting concentrations of the alleles were identical. In one embodiment, it may be assumed that errors are random from peak to peak, and have relatively small additive errors, and larger Poisson and multiplicative error components. The magnitudes of these error components can be estimated from repeated PCR/CGE processing of identical samples. The Chi-square residuals calculation for any data-model fit then can be supported with these modeled squared errors for any peak height or data bin.

In another aspect of the present invention, the presence of fetal cells in a mixed sample and fetal abnormalities in said cells is determined without trying to integrate them in a data-model fitting procedure described above. For example, steps 100-107 can be performed as described above. Then, analysis using Equations 1 and 2 focuses on two indications. First, aneuploidy results in an excess of DNA for the trisomic chromosome, and this is indicated by the difference in mean strengths of the alleles on the trisomic chromosome compared to control chromosomes. A t-test can be applied to the two distributions of m1 and m2 peak heights. These peak heights are normalized to (e.g., divided peak-by-peak by) the corresponding peaks in the maternal-only sample to reduce PCR amplification biases. Second, Equations 1 and 2 show that aneuploidy is associated with less inequality in the heights of m1 and m2 at a given locus, particularly for loci where the paternal allele is distinct from the maternal alleles. Loci are selected where a third (paternal) allele is visibly distinct from two maternal alleles, and the distribution of the inequalities (measured in %) between the m1 and m2 peaks are compared between suspected trisomy chromosomes and control chromosomes. Again, peak heights first are normalized by the maternal-only sample. These two lines of evidence are combined to create an overall likelihood, such as by multiplying the probability values from the two lines of evidence. The presence/absence call is done in a simplified way by looking for loci where a third allele is clearly visible, and comparing the distribution of these peak heights between the maternal and mixed samples. Again, a t-test between these distributions gives the probability of fetal DNA being present.

In another aspect of the invention, the methods herein only determine presence or absence of fetal DNA, and aneuploidy information is known from another sources (e.g. fluorescence in situ hybridization (FISH) assay). For example, it may be desirable only to verify the presence or absence of fetal cells to ensure that a diploid test result is truly due to a normal fetus and not to failure of an assay (e.g. FISH). In this case, the process may be simplified by focusing on detecting the presence of non-maternal alleles without regard to associating them with increases in the maternal allele strengths at the same locus. Thus a process similar to the one outlined above may be used but it is not as necessary to arrange the PCR product lengths so that the products from different loci have distinct length windows in the CGE readout. The alleles from the different loci can be allowed to fall essentially anywhere in the effective measurement length window of the CGE. It also is not necessary to 'lineate' the PCR result(s) via multiple CGE readouts at different stages in the PCR cycling as is suggested in step 107.

Therefore, maternal-only and mixed samples are run and mapped to each other to align maternal allele peak locations, as described above. PCR is run to saturation, or nearly to saturation, to be sure to detect the low abundance fetal sequences. The evidence for fetal DNA then arises from extra peaks in the mixed-sample data with respect to the maternal-sample data. Based on typical heterozygosities of approximately 0.7 for highly polymorphic STRs, the chance of not seeing a distinct paternal allele (distinct from both maternal alleles) when fetal DNA is in fact present decreases approximately as $(0.7^2)^N$, where N is the number of loci included. Thus approximately ten STR loci will provide ~99.9% probability of detection. In addition, the present invention provides methods to determine when there are insufficient fetal cells for a determination and report a non-informative case. The present invention involves quantifying regions of genomic DNA from a mixed sample. More particularly the invention involves quantifying DNA polymorphisms from the mixed sample. In some embodiments, one or more than 1, 2, 3, 4, 5, 6, 7, 8, 9, 10, 15, 20 DNA polymorphism loci (particularly STRs) per target chromosome are analyzed to verify presence of fetal cells.

Any of the steps above can be performed by a computer program product that comprises a computer executable logic that is recorded on a computer readable medium. For example, the computer program can execute some or all of the following functions: (i) controlling enrichment of fetal cells or DNA from mixed sample and reference sample, (ii) pre-amplifying DNA from both samples, (iii) amplifying specific polymorphic DNA regions from both samples, (iv) identifying and quantifying maternal alleles in the reference sample, (v) identifying maternal and non-maternal alleles in the mixed sample, (vi) fitting data on alleles detected from mixed and/or reference samples into data models, (vii) determining the presence or absence of fetal cells in the mixed sample, (viii) declaring normal or abnormal phenotype for a fetus based on data models or declaring non-informative results, and (ix) declaring a specific fetal abnormality based on the above results. In particular, the computer executable logic can fit data on the quantity of DNA polymorphism(s) (e.g. STR's) into one or more data models. One example of a data model provides a determination of a fetal abnormality from given data signals obtained by molecular analysis e.g. CGE. The computer executable logic provides for a determination of the presence or absence of a trisomy, and distinguish whether the trisomy is paternally derived or if it originates from a maternal non-disjunction event. For example, given the following data signals that can be obtained by molecular analysis (e.g. CGE)

m1, which represents a signal obtained from one of the maternal alleles (m1) at a given locus, m2, which represents a signal obtained from the other maternal allele, which might be the same allele, p, which is a signal that is obtained from the paternal allele at a given locus, and p1 and p2, which are signals obtained from the paternal alleles at one given locus when a paternally derived trisomy occurs, and letting α and β, which denote the relative number of maternal and fetal cells, respectively, the following determinations can be made. In the case of a chromosome with maternal non-disjunction trisomy, the data will have the form $$x = \alpha(\square m1+m2) + \beta(m1+m2+p). \quad (1)$$

A normal (diploid) chromosome will give $$x = \alpha(m1+m2) + \beta([m1 \text{ or } m2]+p), \quad (2)$$

and a paternally derived trisomy will give $$x = \alpha(m1+m2) + \beta([m1 \text{ or } m2]+p1+p2). \quad (3)$$

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of evaluating the presence or absence of trisomy in a mixed cell sample by accessing data that reflects the level of polymorphism(s) at two alleles at two or more given loci in a mixed sample (maternal and fetal cells) and in a sample enriched in fetal cells, relating the levels of polymorphism(s) to the number of maternal and fetal cells (α and β in equations 1-3), and determining the presence or absence of trisomy in the samples.

In one embodiment, the computer executing the computer logic of the invention may also include a digital input device such as a scanner. The digital input device can provide information on the polymorphism levels/quantity. For example, a scanner of this invention can provide an image of the DNA polymorphism (particularly STRs) according to method herein. For instance, a scanner can provide an image by detecting fluorescent, radioactive, or other emission; by detecting transmitted, reflected, or scattered radiation; by detecting electromagnetic properties or other characteristics; or by other techniques. The data detected is typically stored in a memory device in the form of a data file. In one embodiment, a scanner may identify one or more labeled targets. For instance, a first DNA polymorphism may be labeled with a first dye that fluoresces at a particular characteristic frequency, or narrow band of frequencies, in response to an excitation source of a particular frequency. A second DNA polymorphism may be labeled with a second dye that fluoresces at a different characteristic frequency. The excitation sources for the second dye may, but need not, have a different excitation frequency than the source that excites the first dye, e.g., the excitation sources could be the same, or different, lasers.

Another aspect of the invention includes kits containing the devices and reagents for performing the enrichment and genetic analysis. Such kits may include the materials for any individual step disclosed, any combination of devices and reagents or the devices and reagents for performing all of the steps. For example, a kit may include the arrays for size-based enrichment, the device for magnetic separation of the cells and reagents for performing PCR or CGE. Also included may be the reagents for performing multiple displacement amplification. This is an exemplary kit and the kits can be constructed using any combination of disclosed materials and devices. The use of the size-based enrichment provides gentle handling that is particularly advantageous for permitting subsequent genetic analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1. Separation of Fetal Cord Blood

FIGS. 7A-7D illustrates a schematic of the device used to separate nucleated cells from fetal cord blood.

Dimensions: 100 mm×28 mm×1 mm

Array design: 3 stages, gap size=18, 12 and 8 μm for the first, second and third stage, respectively.

Device fabrication: The arrays and channels were fabricated in silicon using standard photolithography and deep silicon reactive etching techniques. The etch depth is 140 μm. Through holes for fluid access are made using KOH wet etching. The silicon substrate was sealed on the etched face to form enclosed fluidic channels using a blood compatible pressure sensitive adhesive (9795, 3M, St Paul, Minn.).

Device packaging: The device was mechanically mated to a plastic manifold with external fluidic reservoirs to deliver blood and buffer to the device and extract the generated fractions.

Device operation: An external pressure source was used to apply a pressure of 2.0 PSI to the buffer and blood reservoirs to modulate fluidic delivery and extraction from the packaged device.

Experimental conditions: Human fetal cord blood was drawn into phosphate buffered saline containing Acid Citrate Dextrose anticoagulants. 1 mL of blood was processed at 3 mL/hr using the device described above at room temperature and within 48 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.) and 2 mM EDTA (15575-020, Invitrogen, Carlsbad, Calif.).

Measurement techniques: Cell smears of the product and waste fractions (FIG. 8A-8B) were prepared and stained with modified Wright-Giemsa (WG16, Sigma Aldrich, St. Louis, Mo.).

Performance: Fetal nucleated red blood cells were observed in the product fraction (FIG. 8A) and absent from the waste fraction (FIG. 8B).

Example 2. Isolation of Fetal Cells from Maternal Blood

The device and process described in detail in Example 1 were used in combination with immunomagnetic affinity enrichment techniques to demonstrate the feasibility of isolating fetal cells from maternal blood.

Experimental conditions: blood from consenting maternal donors carrying male fetuses was collected into $K_2$EDTA vacutainers (366643, Becton Dickinson, Franklin Lakes, N.J.) immediately following elective termination of pregnancy. The undiluted blood was processed using the device described in Example 1 at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.). Subsequently, the nucleated cell fraction was labeled with anti-CD71 microbeads (130-046-201, Miltenyi Biotech Inc., Auburn, Calif.) and enriched using the MiniMACS™ MS column (130-042-201, Miltenyi Biotech Inc., Auburn, Calif.) according to the manufacturer's specifications. Finally, the CD71-positive fraction was spotted onto glass slides.

Measurement techniques: Spotted slides were stained using fluorescence in situ hybridization (FISH) techniques according to the manufacturer's specifications using Vysis probes (Abbott Laboratories, Downer's Grove, Ill.). Samples were stained from the presence of X and Y chromosomes. In one case, a sample prepared from a known Trisomy 21 pregnancy was also stained for chromosome 21.

Figure 10:
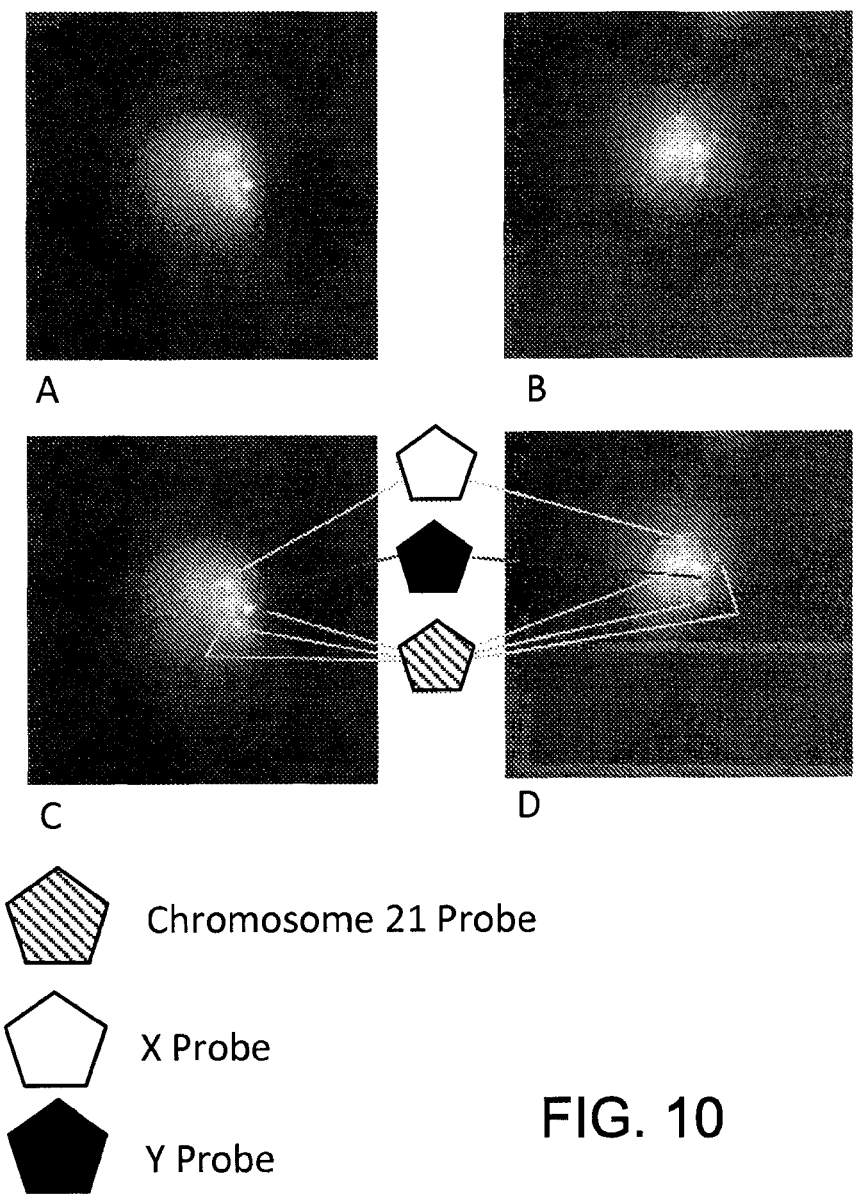
FIG. 10 illustrates trisomy 21 pathology in an isolated fetal nucleated red blood cell.

Performance: Isolation of fetal cells was confirmed by the reliable presence of male cells in the CD71-positive population prepared from the nucleated cell fractions (FIG. 9). In the single abnormal case tested, the trisomy 21 pathology was also identified (FIG. 10).

Example 3. Confirmation of the Presence of Male Fetal Cells in Enriched Samples

Confirmation of the presence of a male fetal cell in an enriched sample is performed using qPCR with primers specific for DYZ, a marker repeated in high copy number on the Y chromosome. After enrichment of fnRBC by any of the methods described herein, the resulting enriched fnRBC are binned by dividing the sample into 100 PCR wells. Prior to binning, enriched samples may be screened by FISH to determine the presence of any fnRBC containing an aneuploidy of interest. Because of the low number of fnRBC in maternal blood, only a portion of the wells will contain a single fnRBC (the other wells are expected to be negative for fnRBC). The cells are fixed in 2% Paraformaldehyde and stored at 4° C. Cells in each bin are pelleted and resuspended in 5 µl PBS plus 1 µl 20 mg/ml Proteinase K (Sigma # P-2308). Cells are lysed by incubation at 65° C. for 60 minutes followed by inactivation of the Proteinase K by incubation for 15 minutes at 95° C. For each reaction, primer sets (DYZ forward primer TCGAGTGCATTCCATTCCG (SEQ ID NO: 159); DYZ reverse primer ATGGAATGGCATCAAACGGAA (SEQ ID NO: 160); and DYZ Taqman Probe 6FAM-TGGCTGTCCATTCCA-MGBNFQ (SEQ ID NO: 161)), TaqMan Universal PCR master mix, No AmpErase and water are added. The samples are run and analysis is performed on an ABI 7300: 2 minutes at 50° C., 10 minutes 95° C. followed by 40 cycles of 95° C. (15 seconds) and 60° C. (1 minute). Following confirmation of the presence of male fetal cells, further analysis of bins containing fnRBC is performed. Positive bins may be pooled prior to further analysis.

Figure 20:
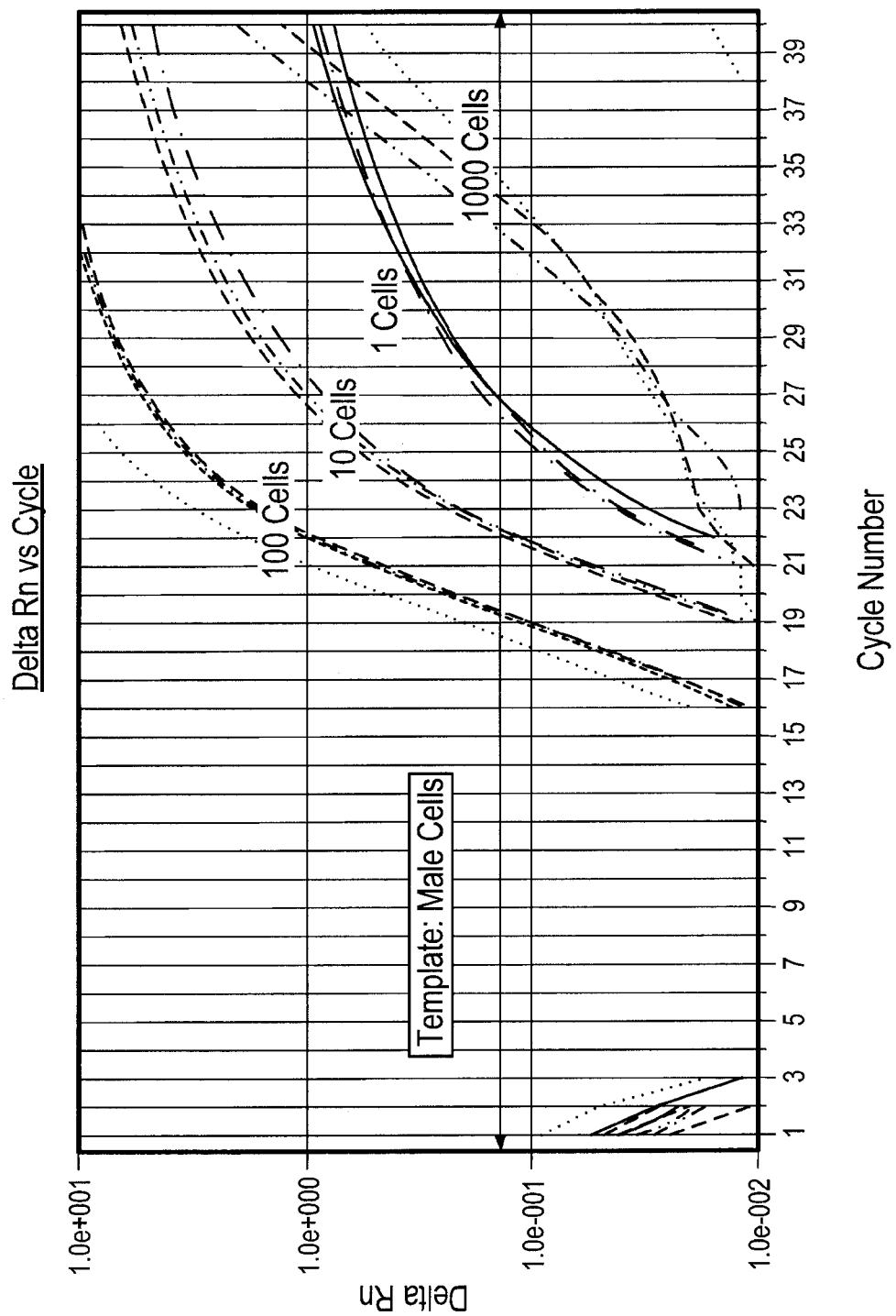
FIG. 20 illustrates the detection of single copies of a fetal cell genome by qPCR.

FIG. 20 shows the results expected from such an experiment. The data in FIG. 20 was collected by the following protocol. Nucleated red blood cells were enriched from cord cell blood of a male fetus by sucrose gradient two Heme Extractions (HE). The cells were fixed in 2% paraformaldehyde and stored at 4° C. Approximately 10×1000 cells were pelleted and resuspended each in 5 µl PBS plus 1 µl 20 mg/ml Proteinase K (Sigma # P-2308). Cells were lysed by incubation at 65° C. for 60 minutes followed by a inactivation of the Proteinase K by 15 minute at 95° C. Cells were combined and serially diluted 10-fold in PBS for 100, 10 and 1 cell per 6 µl final concentration were obtained. Six µl of each dilution was assayed in quadruplicate in 96 well format. For each reaction, primer sets (DYZ forward primer TCGAGTGCATTCCATTCCG (SEQ ID NO: 159); 0.9 uM DYZ reverse primer ATGGAATGGCATCAAACGGAA (SEQ ID NO: 160); and 0.5 uM DYZ TaqMan Probe 6FAM-TGGCTGTCCATTCCA-MGBNFQ (SEQ ID NO: 161)), TaqMan Universal PCR master mix, No AmpErase and water were added to a final volume of 25 µl per reaction. Plates were run and analyzed on an ABI 7300: 2 minutes at 50° C., 10 minutes 95° C. followed by 40 cycles of 95° C. (15 seconds) and 60° C. (1 minute). These results show that detection of a single fnRBC in a bin is possible using this method.

Example 4. Confirmation of the Presence of Fetal Cells in Enriched Samples by STR Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Individual positive cells are isolated by "plucking" individual positive cells from the enhanced sample using standard micromanipulation techniques. Using a nested PCR protocol, STR marker sets are amplified and analyzed to confirm that the FISH-positive aneuploid cell(s) are of fetal origin. For this analysis, comparison to the maternal genotype is typical. An example of a potential resulting data set is shown in Table 2. Non-maternal alleles may be proven to be paternal alleles by paternal genotyping or genotyping of known fetal tissue samples. As can be seen, the presence of paternal alleles in the resulting cells, demonstrates that the cell is of fetal origin (cells #1, 2, 9, and 10). Positive cells may be pooled for further analysis to diagnose aneuploidy of the fetus, or may be further analyzed individually.

TABLE 2

STR locus alleles in maternal and fetal cells

| DNA Source | STR locus D14S | STR locus D16S | STR locus D8S | STR locus F13B | STR locus vWA |
|---|---|---|---|---|---|
| Maternal alleles | 14, 17 | 11, 12 | 12, 14 | 9, 9 | 16, 17 |
| Cell #1 alleles |  | 8 |  |  | 19 |
| Cell #2 alleles | 17 |  | 15 |  |  |
| Cell #3 alleles |  |  | 14 |  |  |
| Cell #4 alleles |  |  |  |  |  |
| Cell #5 alleles | 17 | 12 |  | 9 |  |
| Cell #6 alleles |  |  |  |  |  |
| Cell #7 alleles |  |  |  |  | 19 |
| Cell #8 alleles |  |  |  |  |  |
| Cell #9 alleles | 17 |  | 14 | 7, 9 | 17, 19 |
| Cell #10 alleles |  |  | 15 |  |  |

Example 5. Confirmation of the Presence of Fetal Cells in Enriched Samples by SNP Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Samples testing positive with FISH analysis are then binned into 96 microtiter wells, each well containing 15 µl of the enhanced sample. Of the 96 wells, 5-10 are expected to contain a single fnRBC and each well should contain approximately 1000 nucleated maternal cells (both WBC and mnRBC). Cells are pelleted and resuspended in 5 µl PBS plus 1 µl 20 mg/ml Proteinase K (Sigma # P-2308). Cells are lysed by incubation at 65° C. for 60 minutes followed by a inactivation of the Proteinase K by 15 minute at 95° C.

In this example, the maternal genotype (BB) and fetal genotype (AB) for a particular set of SNPs is known. The genotypes A and B encompass all three SNPs and differ from each other at all three SNPs. The following sequence from chromosome 7 contains these three SNPs (rs7795605, rs7795611 and rs7795233 indicated in brackets, respectively) (ATGCAGCAAGGCACAGACTAA[G/A]CAAGGAGA[G/C]GCAAAATTTTC [A/G]TAGGG GAGAGAAATGGGTCATT (SEQ ID NO: 162).

In the first round of PCR, genomic DNA from binned enriched cells is amplified using primers specific to the outer portion of the fetal-specific allele A and which flank the interior SNP (forward primer ATGCAGCAAGGCACA-GACTACG (SEQ ID NO: 163); reverse primer AGAGGGGAGAGAAATGGGTCATT (SEQ ID NO: 164)). In the second round of PCR, amplification using real time SYBR Green PCR is performed with primers specific to the inner portion of allele A and which encompass the interior SNP (forward primer CAAGGCACA-GACTAAGCAAGGAGAG (SEQ ID NO: 165); reverse primer GGCAAAATTTTCATAGGGGAGA-GAAATGGGTCATT (SEQ ID NO: 166).

Figure 21:
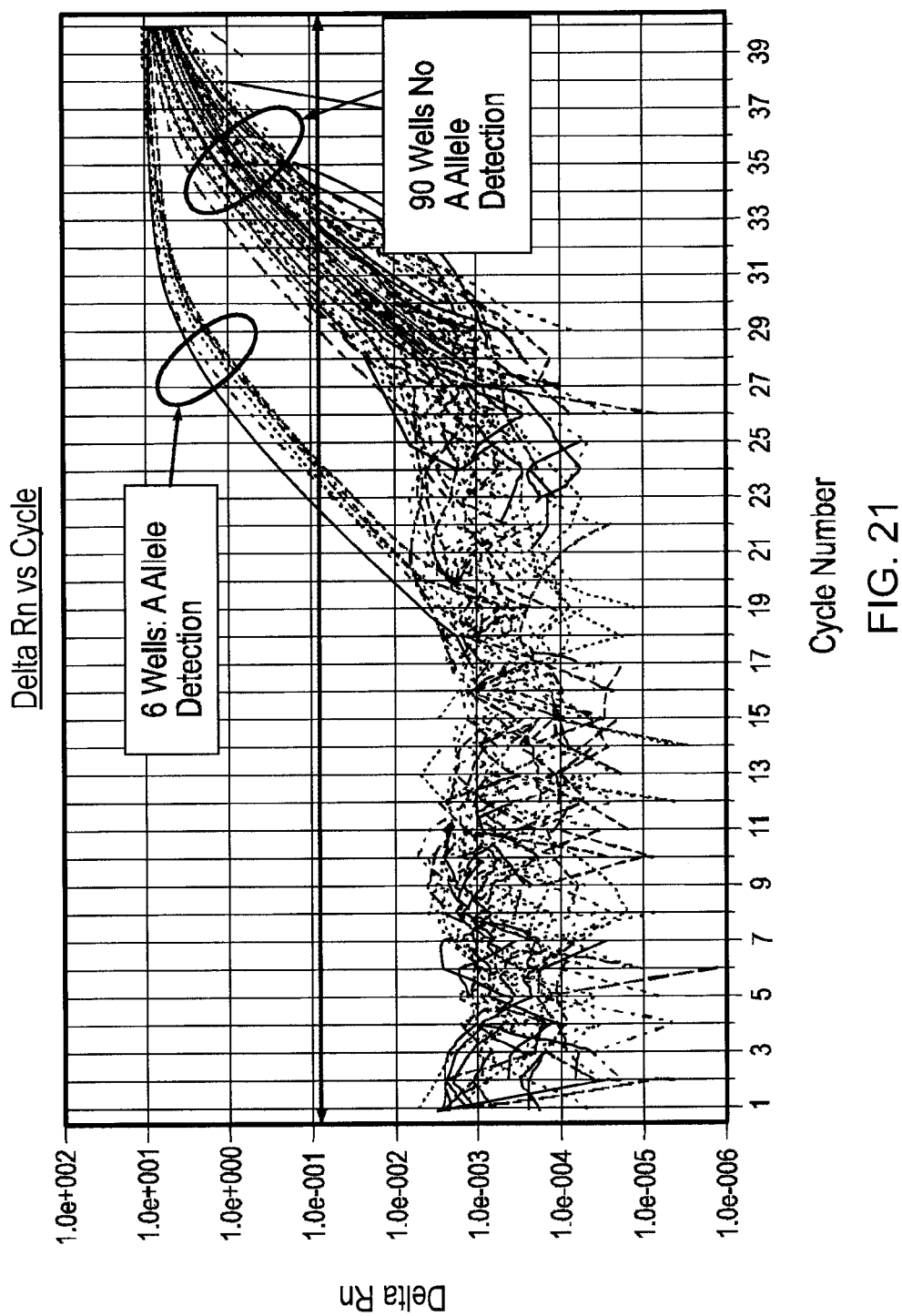
FIG. 21 illustrates detection of single fetal cells in binned samples by SNP analysis.
Figure 22:
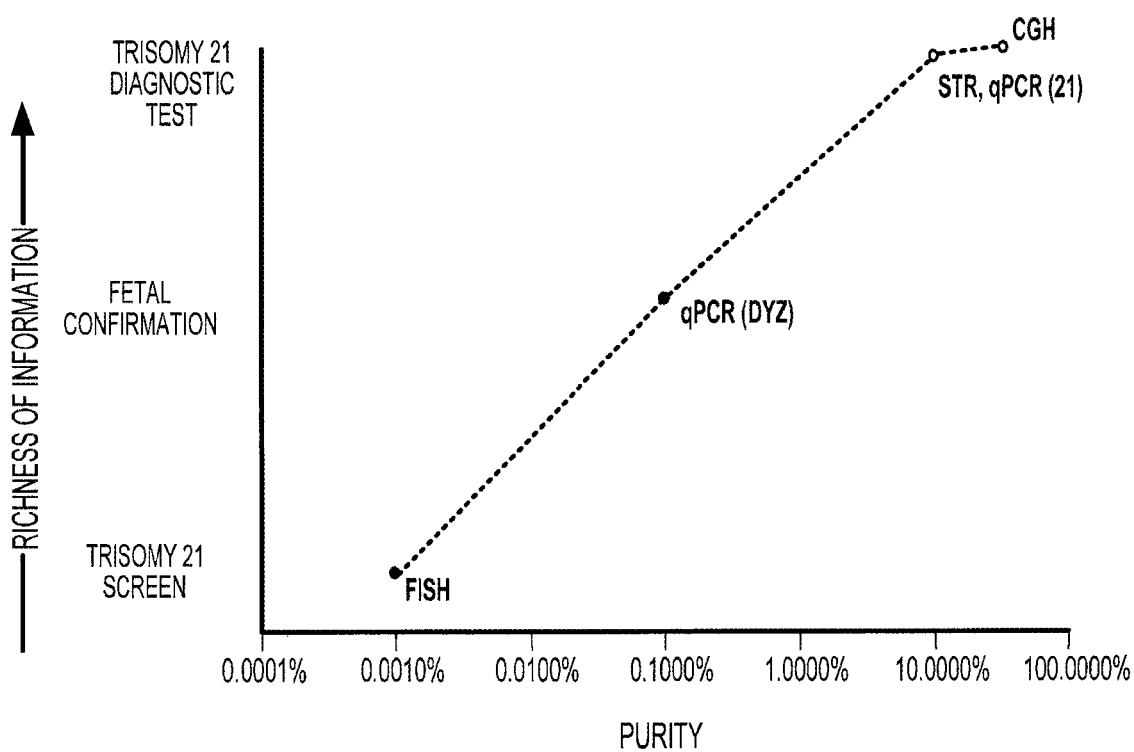
FIG. 22 illustrates a method of trisomy testing. The trisomy 21 screen is based on scoring of target cells obtained from maternal blood. Blood is processed using a cell separation module for hemoglobin enrichment (CSM-HE). Enriched cells are transferred to slides that are first stained and subsequently probed by FISH. Images are acquired, such as from bright field or fluorescent microscopy, and scored. The proportion of trisomic cells of certain classes serves as a classifier for risk of fetal trisomy 21. Fetal genome identification can performed using assays such as: (1) STR markers; (2) qPCR using primers and probes directed to loci, such as the multi-repeat DYZ locus on the Y-chromosome; (3) SNP detection; and (4) CGH (comparative genome hybridization) array detection.
Figure 23:
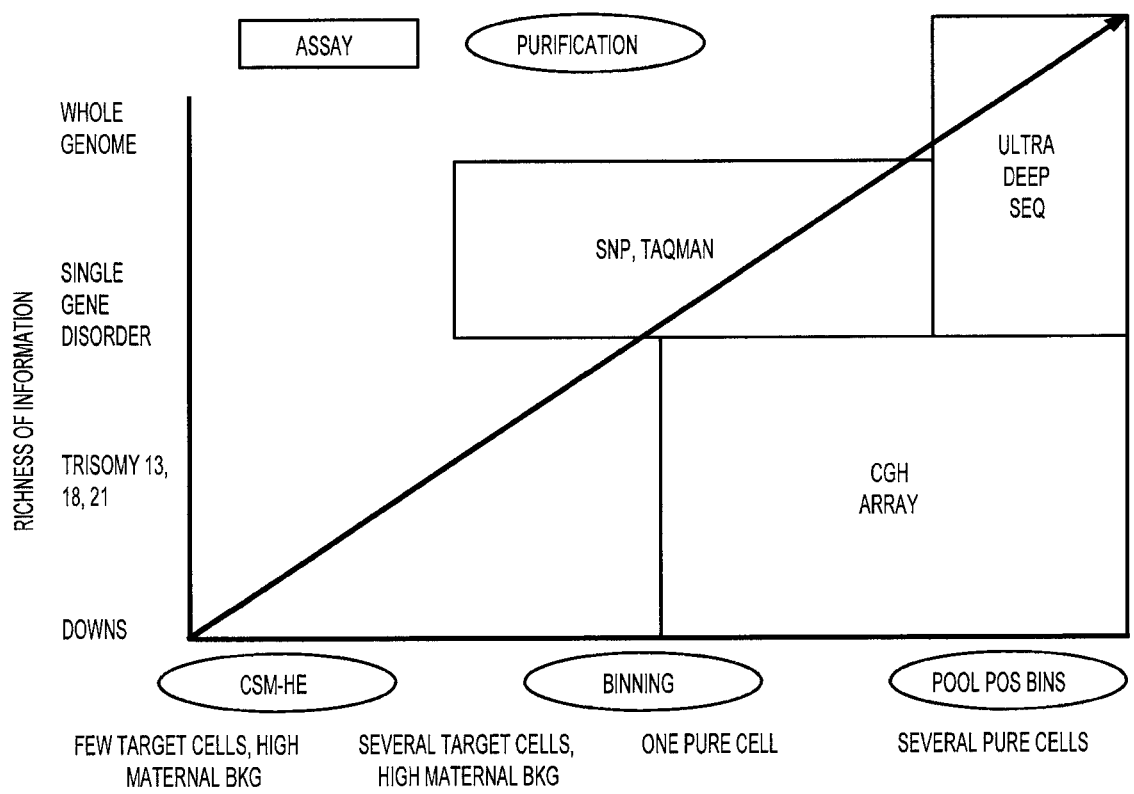
FIG. 23 illustrates assays that can produce information on the presence of aneuploidy and other genetic disorders in target cells. Information on anueploidy and other genetic disorders in target cells may be acquired using technologies such as: (1) a CGH array established for chromosome counting, which can be used for aneuploidy determination and/or detection of intra-chromosomal deletions; (2) SNP/ taqman assays, which can be used for detection of single nucleotide polymorphisms; and (3) ultra-deep sequencing, which can be used to produce partial or complete genome sequences for analysis.

Expected results are shown in FIG. 21. Here, six of the 96 wells test positive for allele A, confirming the presence of cells of fetal origin, because the maternal genotype (BB) is known and cannot be positive for allele A. DNA from positive wells may be pooled for further analysis or analyzed individually.

Example 6. Analysis of STR's

Figure 11:
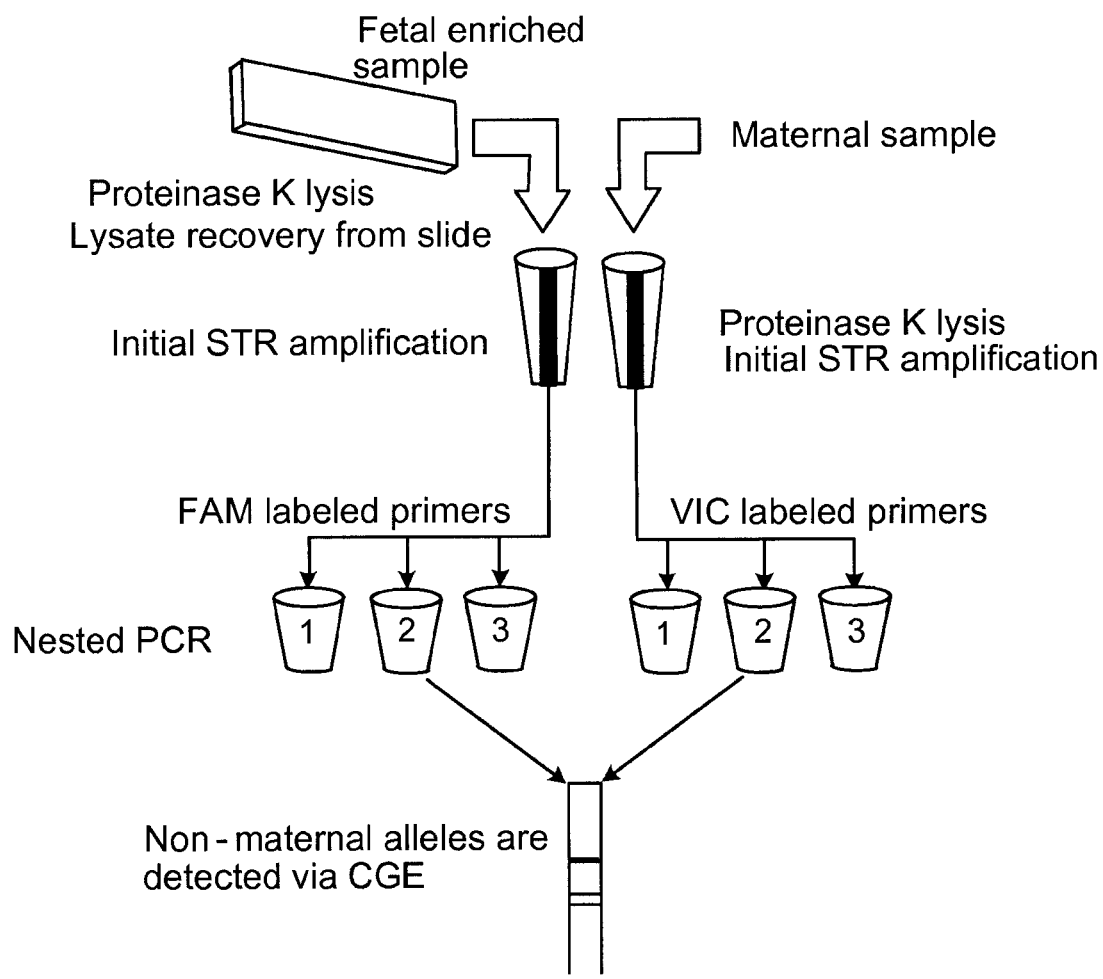
FIG. 11 depicts a flow chart depicting the major steps involved in detecting paternal alleles in a fetal enriched sample using fluorescently labeled primers.

FIG. 11 illustrates a diagram of the planned protocol for clinical practice where a reference sample (maternal blood) and a fetal enriched sample will be processed in parallel. Twelve polymorphic STRs are chosen (See FIG. 12) and associated nested PCR primers were designed (FIG. 13-14).

Cell Lysis: Cells are lysed in a proteinase K solution by heating samples for 60 minutes at 65° C., followed by a heating step of 15 minutes at 95° C.

1$^{st}$ round of PCR: A polymerase mix that includes 12 specialized STR primer pairs is added to the crude lysate. A master PCR mix is generated according to the number of samples as per the recipe below. For the reference sample 44 µL of the master mix are added directly to the cell lysate. For the sample recovered from the slide the volume of the reaction is adjusted as necessary. (e.g. 32 µL crude lysate in a 100 µL total reaction volume). A no template or negative control is generated to test for contamination.

| Master mix outer | 1 | Multiplex PCR cylce | | |
|---|---|---|---|---|
| 12-plex | rxn | Step | Temp (C.) | Time (mins) |
| 2X Qiagen Mix | 25.0 | 1.0 | 95 | 0.5 |
| titanium | 1.0 | 2.0 | 94 | 0.5 |
| Qiagen Q factor | 5.0 | 3.0 | 68 | 1.5 |
| water | 10.0 | 4.0 | 72 | 1.5 |
| 4.2 uM 12 plex primers | 3.0 | 5.0 | cycle to step 2, 44 times | |
| Cell lysate | 6.0 | 6.0 | 72 | 10 |
|  | 50.0 |  |  |  |

Nested PCR: After PCR, optionally, diluted products are added to a second nested primer PCR reaction. Two ul aliquot of each 12-plex PCR reaction is diluted 40 fold (to 80 ul total) with nuclease free water from the PCR kit. The diluted fetal enriched 12-plex reaction could be used as template for a master mix for 8 nested PCR reactions with FAM labeled primers. A second master mix can be generated using the dilution from the maternal reference for 8 nested PCR reactions with VIC labeled primers. The following primer pairs are suggested. A no template or negative control is generated to test for contamination.

| Nested STR primer facts | | | |
|---|---|---|---|
| rxn# | Reaction temp | STR primers | Fragment size ranges |
| 1 | 68 | CSF1P0 THO1 | 295-327, 171-215 |
| 2 | 68 | TPOX CYARO4 | 220-256, 172-205 |
| 3 | 68 | F13A | 179-235 |
| 4 | 68 | FIBRA | 158-286 |

-continued

Nested STR primer facts

| rxn# | Reaction temp | STR primers | Fragment size ranges |
|---|---|---|---|
| 5 | 63 | VWA D21S11 | 122-182 202-265 |
| 6 | 63 | CD4 | 86-141 |
| 7 | 63 | D14S1434 | 70-102 |
| 8 | 63 | D22S1045 | 76-109 |

Master mix for nested primers

| | 1 rxn | 9 rxns |
|---|---|---|
| 2X Q Mix | 12.5 | |
| | 112.5 | |
| titanium | 0.5 | 4.5 |
| Q | 2.5 | |
| | 22.5 | |
| water | 3.3 | |
| | 29.3 | |
| 5 uM primers | 1.3 | |
| 40X diluted template | 5.0 | |
| | 45.0 | |
| | 25.0 | |
| | 213.8 | |

Nested PCR cycle

| Step | Temp (C.) | Time (mins) |
|---|---|---|
| 1.0 | 95 | 0.5 |
| 2.0 | 94 | 0.5 |
| 3.0 | X | 1.5 |
| 4.0 | 72 | 1.5 |
| 5.0 | cycle to step 2, 44 times | |
| 6.0 | 72 | 10 |

The amplification with the nested PCR primers is run with an annealing temperature of 63° C. or 68° C. depending on the primer pair being amplified as indicated in FIG. 13 and FIG. 14.

Detection on ABI 310 Instrument: PCR products are detected on an Agilent Bioanalyzer. The maternal reference VIC labeled PCR reaction products is diluted 10 fold in nano-pure water (17.8 uOhms). Another 10 fold dilution of the fetal enriched FAM-PCR products is generated. The ABI loading buffer is prepared by adding 0.5 μL LIZ 500 size standard to 12 μL Hi Di Formamide (scale as appropriate to the number of samples, include enough buffer for the negative control to test for contamination). 1 μL diluted PCR product is added to 12 ul loading buffer. The sample is heated to 95° C. for 2 minutes and then placed on ice. The samples are loaded onto the ABI 310 as per the manufacturer's instructions.

Analysis: For analysis the ABI fragments output are examined for the expected peak sizes as per the nested STR primer facts table (FIG. 13 and FIG. 14). For each STR locus is determined whether there are 1 or 2 alleles (homozygous or heterozygous) for the fetal enriched (FAM labeled sample) or the maternal reference (VIC labeled sample). Alleles generated from the fetal enriched (FAM labeled sample) that are not present in the maternal reference (VIC labeled sample) are unique to the fetus and verify the presence of fetal cells in the sample. If the number of fetal cells is particularly low (<5 cells), not all loci or alleles will always amplify. Allele drop out can generate a false negative. A false positive is most likely generated from contamination and has not been observed in tests to date. If the purity of fetal cells is particularly low (<10% in tests executed on the bioanalyzer) signal intensity of paternal alleles can be very weak. This can also generate a false negative result. In clinical practice the amplicons will have different fluorescent labels incorporated into them marking them as the maternal reference or the fetal enriched samples. The labels allow the samples to be loaded simultaneously into an ABI 310 capillary and differentiated. Paternal alleles are identified as those unique to the fetal enriched sample in comparison to the maternal reference. The efficiency of the overall process is determined after sufficient samples have been analyzed on the ABI 310 to establish the input cell purity and minimum number of fetal cells necessary to achieve 99% detection at 0.1% false positive rate.

Example 7. Cord Blood Experiment

Figure 15:
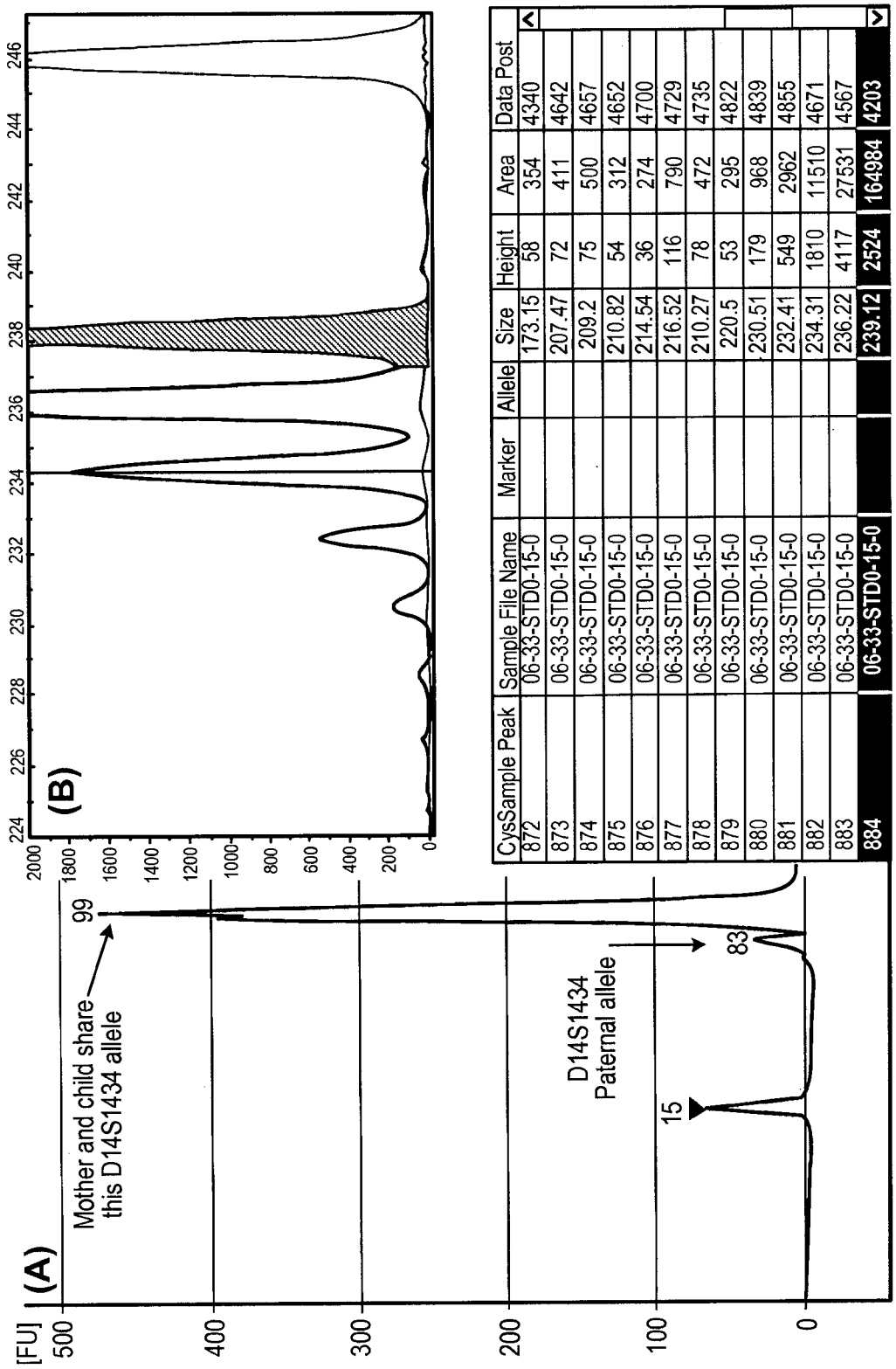
FIG. 15 illustrates the resolution for the ABI 310 bioanalyzer.
Figure 16:
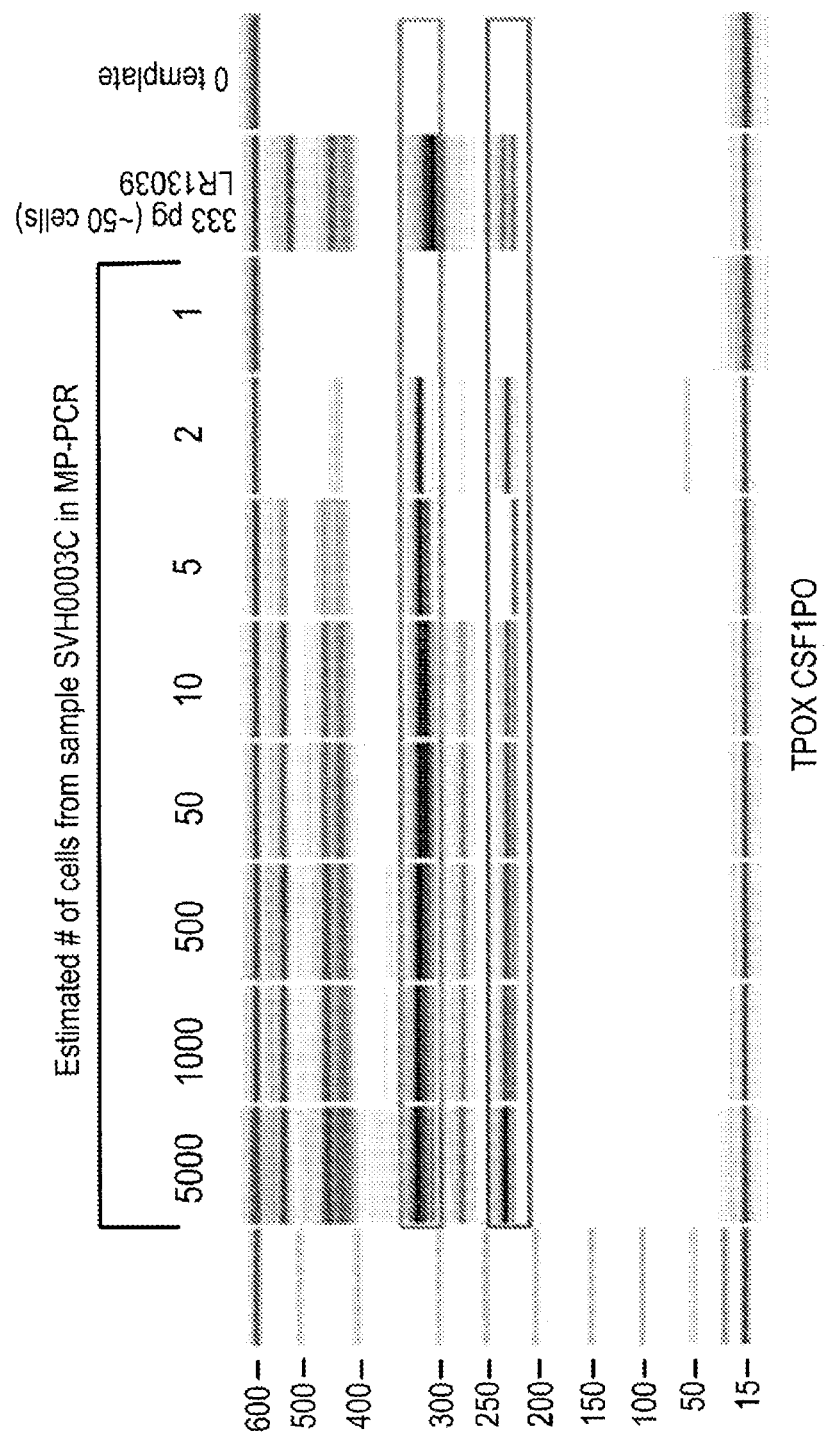
FIG. 16 illustrates the detection limit on fixed cord blood.

The protocol detection limit was determined using fixed cells from cord blood. Cord blood from clinical sample SVH0003C was subjected to erythrocyte lysis and the remaining leukocytes were fixed in a solution of PBS and 2% para-formaldehyde. Cell numbers were estimated from hemocytometer counts and dilutions made into a Tris protienase K (PK) solution. After cell lysis and PK inactivation a PCR cocktail including primers for STR loci TPOX and CSF1P0 was added directly to the crude lysate and amplified as described in Example 6. The products were analyzed on an Agilent bioanalyzer. FIGS. 15A-15B shows representative results. TPOX and CSF1P0 amplification products are underline in boxes. Detection for the PCR protocol from fixed cord blood can occur with less than 10 cells as shown by the result in FIG. 16.

Example 8. Detection of 10 Fetal Cells at 10% Purity without Nested PCR

Figure 17:
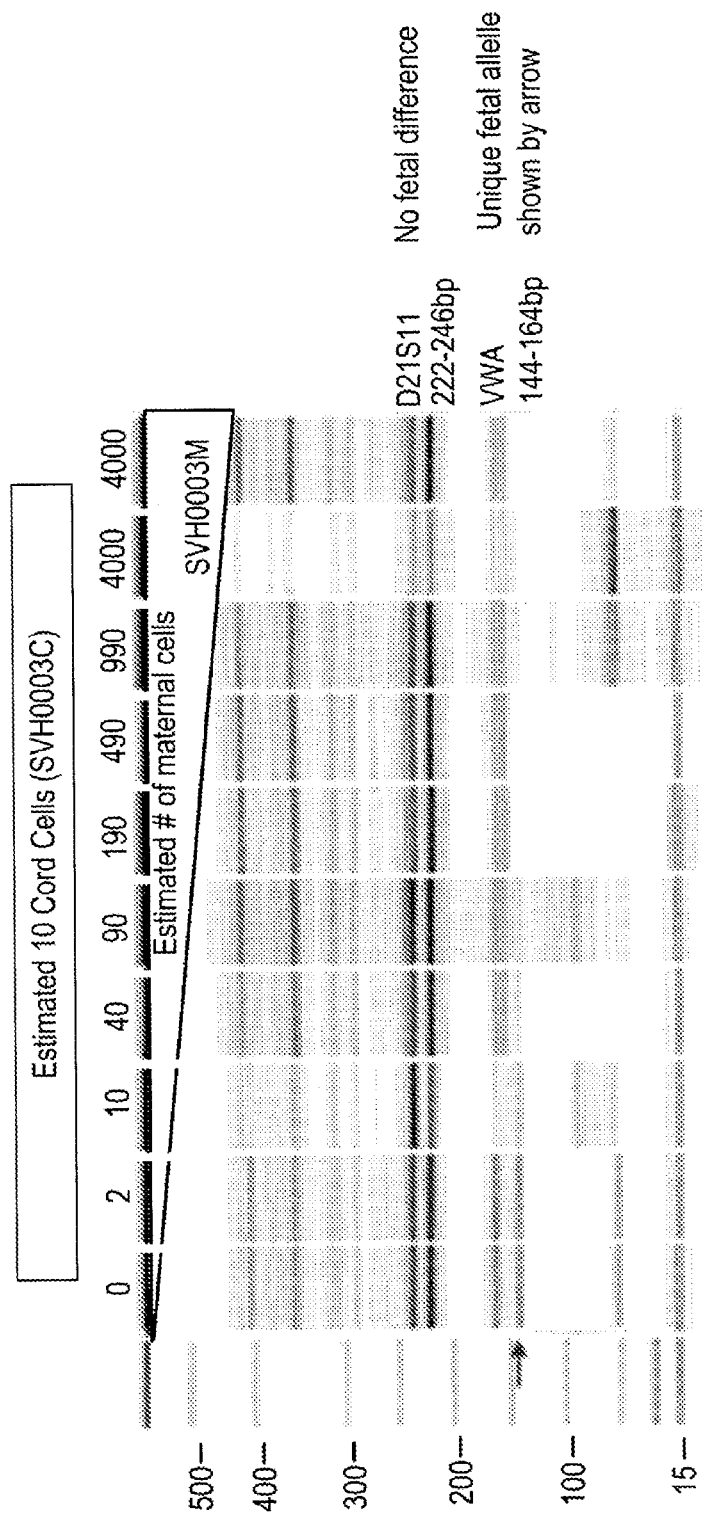
FIG. 17 illustrates the detection of 10 fetal cells at 10% purity without nested PCR.

An estimated 10 fetal cells were mixed with increasing amounts of maternal cells (approximately 0-4000 cells as measured by hemocytometer counts). After proteinase K lysis, only a $1^{st}$ round of PCR with primers to STR loci D21S11 and VWA was executed as described in Example 6. FIG. 17 shows representative results. The mother and fetus are identical at the D21S11 locus but the child has a unique (paternal) allele at the VWA locus. FIG. 17 shows that detection of the paternal VWA allele is lost when the fetal purity drops below 10%.

Example 9. Generation of STR Markers

Figure 18:
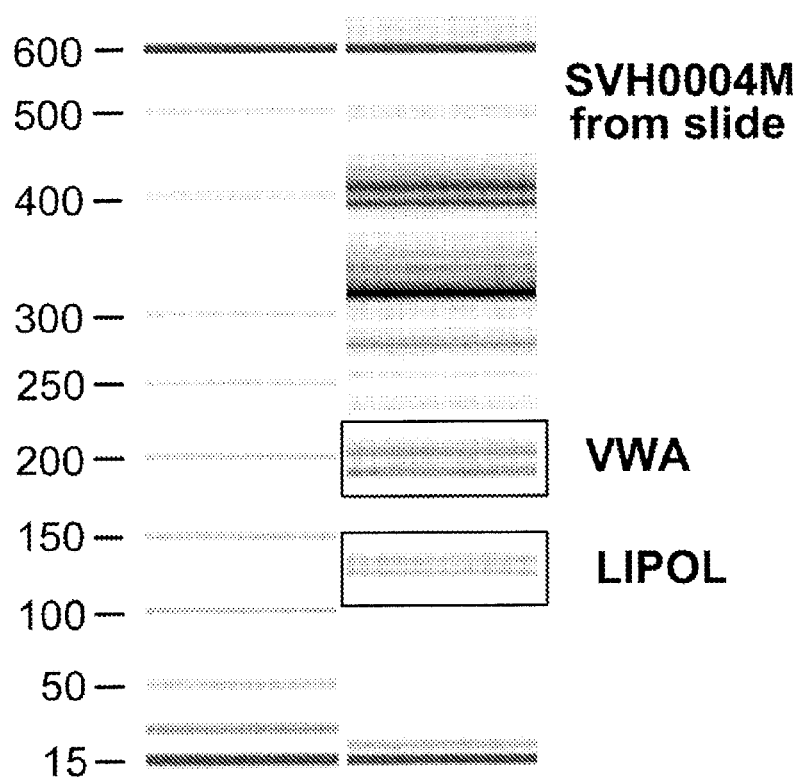
FIG. 18 illustrates the generation of STR markers on fixed cells recovered from a slide.

Approximately 100 cells were spotted onto a poly-L-lysine slide and heat dried. Cells were fixed in a MeOH acetic acid solution and rinsed in MeOH. After air drying the slide was treated with 2% para-formaldehyde for 10 minutes then washed in 1×PBS. The slide was dehydrated in passes of EtOH for 1 min each in 70%, 80%, 90%, and finally 100%. A dam was applied around the cells and 30 ul of proteinase K was added on top of the cells and a cover slip adhered over the dam. The slide was incubated on a heat block at 65° C. for 60 minutes and 95° C. for 15 minutes. The lysate solution was then transferred directly to a 100 ul PCR reaction with VWA and LIPOL primer. PCR protocol and analysis were performed as described in Example 6. FIG. 18 shows representative results. VWA and LIPOL amplicons are underlined by boxes in the figure. These results show that STRs markers can be generated from fixed cells recovered from a slide.

Figure 19:
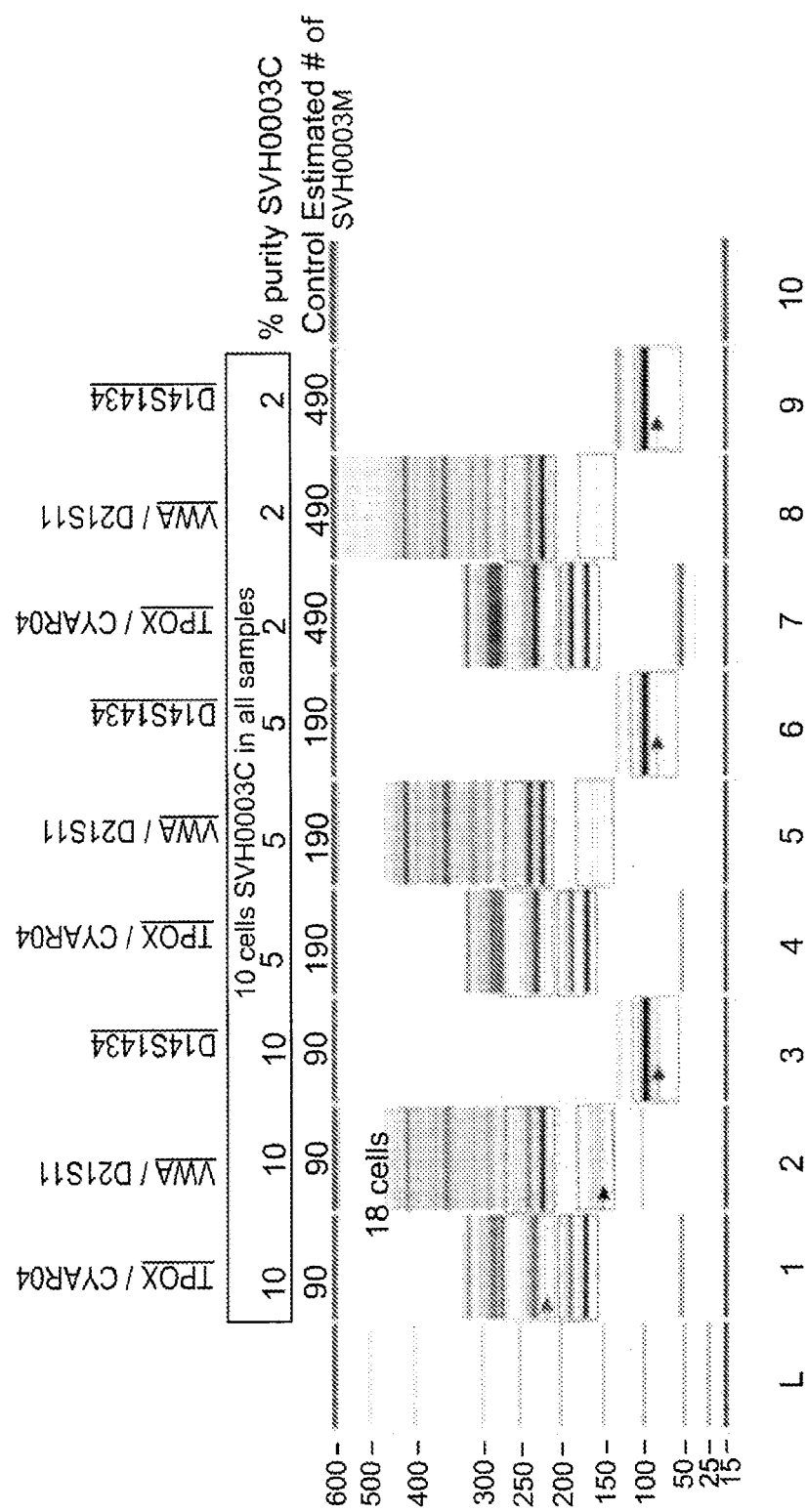
FIG. 19 illustrates detection of fetal alleles at less than 10% purity after nested PCR amplification of STRs.

Example 10. Detection of Fetal Alleles at Less than 10% Purity after Nested PCR Amplification of STRs Mutliplex PCR reactions from samples with 10 fetal cells in a background of maternal cells generating at 10%, 5% and 2% fetal cells purity concentration were performed as described in Example 6. A dilution of the three multiplex PCR reactions was used as template in nested PCR reactions for STRs TPOX/CYAR04, VWA/D21S11, and D14S1434 as described in Example 6. FIG. 19 shows representative results. The underlined loci are known to have unique fetal alleles which are designated by arrows when visible in the gel. The three loci were visible when fetal cells constituted 10% of the sample. D14S1434 loci was visible when fetal cells constituted 5% and 2% of the sample.

Example 11. Resolution of the Bioanalyzer

FIG. 15A shows that the Bioanalyzer can resolve a 16 base pair difference between the 99 base pair D14S1434 maternal allele and the 83 base pair paternal allele in a mixed fetal sample at 5% purity (also shown in FIG. 11, lane 6). FIG. 15B shows that the output of fragments calibration standards. The output of an ABI310 fragment calibration standard is shown in blue or FAM label. Fragments of 232, 234, 236 and 238 are easily resolved from one another. For a resolution comparison note that the orange, VIC labeled, 246 size standard peak is 8 bases away from the FAM labeled 238 peak, half the distance as the maternal and paternal alleles in the Bioanalyzer trace.

Example 12. Analysis of STR's Using Quantitative Fluorescence

Genomic DNA from enriched fetal cells and a maternal control sample will be genotyped for specific STR loci in order to assess the presence of chromosomal abnormalities, such as trisomy. Due to the small number of fetal cells typically isolated from maternal blood it is advantageous to perform a pre-amplification step prior to analysis, using a protocol such as improved primer extension pre-amplification (IPEP) PCR. Cell lysis is carried out in 10 ul High Fidelity buffer (50 mM Tris-HCL, 22 mM $(NH_4)_2SO_4$ 2.5 mM $MgCl_2$, pH 8.9) which also contained 4 mg/ml proteinase K and 0.5 vol % Tween 20 (Merck) for 12 hours at 48° C. The enzyme is then inactivated for 15 minutes at 94° C. Lysis is performed in parallel batches in 5 ul, 200 mM KOH, 50 mM dithiothreitol for 10 minutes at 65.degree. The batches are then neutralized with 5 ul 900 mM TrisHCl pH 8.3, 300 mM KCl. Preamplication is then carried out for each sample using completely randomized 15-mer primers (16 uM) and dNTP (100 uM) with 5 units of a mixture of Taq polymerase (Boehringer Mannheim) and Pwo polymerase (Boehringer Mannheim) in a ratio of 10:1 under standard PCR buffer conditions (50 mM Tris-HCL, 22 mM $(NH_4)_2 SO_4$, 2.5 mM $Mg_2$, pH 8.9, also containing 5% by vol. of DMSO) in a total volume of 60 ul with the following 50 thermal cycles: Step Temperature Time (1) 92° C. 1 Min 30 Sec; (2) 92° C. 40 Min (3) 37° C. 2 Min; (4) ramp: 0.1° C./sec to 55° C. (5) 55° C. 4 Min (6) 68° C. 30 Sec (7) go to step 2, 49 times (8) 8° C. 15'Min.

Dye labeled primers will then be selected from Table 3 based on STR loci on a chromosomes of interest, such as 13, 18, 21 or X. The primers are designed so that one primer of each pair contains a fluorescent dye, such as ROX, HEX, JOE, NED, FAM, TAMARA or LIZ. The primers are placed into multiplex mixes based on expected product size, fluorescent tag compatibility and melting temperature. This allows multiple STR loci to be assayed at once and yet still conserves the amount of initial starting material required. All primers are initially diluted to a working dilution of 10 pM. The primers are then combined in a cocktail that has a final volume of 40 ul. Final primer concentration is determined by reaction optimization. Additional PCR grade water is added if the primer mix is below 40 ul. A reaction mix containing 6 ul of Sigma PCR grade water, 1.25 ul of Perkin Elmer Goldamp PCR buffer, 0.5 ul of dNTPs, 8 ul of the primer cocktail, 0.12 ul of Perkin Elmer Taq Gold Polymerase and 1.25 ul of Mg (25 mM) is mixed for each sample. To this a 1 ul sample containing preamplified DNA from enriched fetal cells or maternal control genomic DNA is added.

The reaction mix is amplified in a DNA thermocyler, (PTC-200; MJ Research) using an amplification cycle optimized for the melting temperature of the primers and the amount of sample DNA.

The amplification product will then analyzed using an automated DNA sequencer system, such as the ABI 310, 377, 3100, 3130, 3700 or 3730, or the Li-Cor 4000, 4100, 4200 or 4300. For example when the amplification products are prepared for analysis on a ABI 377 sequencer, 6 ul of products will be removed and combined with 1.6 ul of loading buffer mix. The master loading buffer mix contains 90 ul deionized formamide combined with 25 ul Perkin Elmer loading dye and 10 ul of a size standard, such as the ROX 350 size standard. Various other standards can be used interchangeably depending on the sizes of the labeled PCR products. The loading buffer and sample are then heat denatured at 95° C. for 3 minutes followed by flash cooling on ice. 2 ul of the product/buffer mix is then electrophoresed on a 12 inch 6% (19:1) polyacrylamide gel on an ABI 377 sequencer.

The results will then be analyzed using ABI Genotyper software. The incorporation of a fluorochrome during amplification allows product quantification for each chromosome specific STR, with 2 fluorescent peaks observed in a normal heterozygous individual with an approximate ratio of 1:1. By comparison in trisomic samples, either 3 fluorescent peaks with a ratio of 1:1:1 (trialleleic) or 2 peaks with a ratio of around 2:1 (diallelic) are observed. Using this method screening may be carried out for common trisomies and sex chromosome aneuploidy in a single reaction.

TABLE 3

Primer Sets for STRs on Chromsomes 13, 18, 21 and X

| Ch. | STR Marker | Primer 1 | Primer 2 |
|---|---|---|---|
| 13 | D13S317 | 5ACAGAAGTCTGGGATGTGGA (SEQ ID NO 1) | GCCCAAAAAGACAGACAGAA (SEQ ID NO 2) |

TABLE 3-continued

Primer Sets for STRs on Chromosomes 13, 18, 21 and X

| Ch. | STR Marker | Primer 1 | Primer 2 |
|---|---|---|---|
| | D13S1493 | ACCTGTTGTATGGCAGCAGT (SEQ ID NO 3) | AGTTGACTCTTTCCCCAACTA (SEQ ID NO 4) |
| | D13S1807 | TTTGGTAAGAAAAACATCTCCC (SEQ ID NO 5) | GGCTGCAGTTAGCTGTCATT (SEQ ID NO 6) |
| | D13S256 | CCTGGGCAACAAGAGCAAA (SEQ ID NO 7) | AGCAGAGAGACATAATTGTG (SEQ ID NO 8) |
| | D13S258- | ACCTGCCAAATTTTACCAGG (SEQ ID NO 9) | GACAGAGAGAGGGAATAAACC (SEQ ID NO 10) |
| | D13S285 | ATATATGCACATCCATCCATG (SEQ ID NO 11) | GGCCAAAGATAGATAGCAAGGTA (SEQ ID NO 12) |
| | D13S303 | ACATCGCTCCTTACCCCATC (SEQ ID NO 13) | TGTACCCATTAACCATCCCCA (SEQ ID NO 14) |
| | D13S317 | ACAGAAGTCTGGGATGTGGA (SEQ ID NO 15) | GCCCAAAAAGACAGACAGAA (SEQ ID NO 16) |
| | D13S779 | AGAGTGAGATTCTGTCTCAATTAA (SEQ ID NO 17) | GGCCCTGTGTAGAAGCTGTA (SEQ ID NO 18) |
| | D13S787 | ATCAGGATTCCAGGAGGAAA (SEQ ID NO 19) | ACCTGGGAGGCGGAGCTC (SEQ ID NO 20) |
| | D13S793 | GGCATAAAAATAGTACAGCAAGC (SEQ ID NO 21) | ATTTGAACAGAGGCATGTAC (SEQ ID NO 22) |
| | D13S796 | CATGGATGCAGAATTCACAG (SEQ ID NO 23) | TCATCTCCCTGTTTGGTAGC (SEQ ID NO 24) |
| | D13S800 | AGGGATCTTCAGAGAAACAGG (SEQ ID NO 25) | TGACACTATCAGCTCTCTGGC (SEQ ID NO 26) |
| | D13S894 | GGTGCTTGCTGTAAATATAATTG (SEQ ID NO 27) | CACTACAGCAGATTGCACCA (SEQ ID NO 28) |
| 18 | D18S51 | CAAACCCGACTACCAGCAAC (SEQ ID NO 29) | GAGCCATGTTCATGCCACTG (SEQ ID NO 30) |
| | D18S1002 | CAAAGAGTGAATGCTGTACAAACAGC (SEQ ID NO 31) | CAAGATGTGAGTGTGCTTTTCAGGAG (SEQ ID NO 32) |
| | D18S1357 | ATCCCACAGGATGCCTATTT (SEQ ID NO 33) | ACGGGAGCTTTTGAGAAGTT (SEQ ID NO 34) |
| | D18S1364 | TCAAATTTTTAAGTCTCACCAGG (SEQ ID NO 35) | GCCTGTAGAAAGCAACAACC (SEQ ID NO 36) |
| | D18S1370 | GGTGACAGAGCAAGACCTTG (SEQ ID NO 37) | GCCTCTTGTCATCCCAAGTA (SEQ ID NO 38) |
| | D18S1371 | CTCTCTTCATCCACCATTGG (SEQ ID NO 39) | GCTGTAAGAGACCTGTGTTG (SEQ ID NO 40) |
| | D18S1376 | TGGAACCACTTCATTCTTGG (SEQ ID NO 41) | ATTTCAGACCAAGATAGGC (SEQ ID NO 42) |
| | D18S1390 | CCTATTTAAGTTTCTGTAAGG (SEQ ID NO 43) | ATGGTGTAGACCCTGTGGAA (SEQ ID NO 44) |
| | D18S499 | CTGCACAACATAGTGAGACCTG (SEQ ID NO 45) | AGATTACCCAGAAATGAGATCAGC (SEQ ID NO 46) |
| | D18S535 | TCATGTGACAAAAGCCACAC (SEQ ID NO 47) | AGACAGAAATATAGATGAGAATGCA (SEQ ID NO 48) |
| | D18S535 | TCATGTGACAAAAGCCACAC (SEQ ID NO 49) | AGACAGAAATATAGATGAGAATGCA (SEQ ID NO 50) |
| | D18S542 | TTTCCAGTGGAAACCAAACT (SEQ ID NO 51) | TCCAGCAACAACAAGAGACA (SEQ ID NO 52) |
| | D18S843 | GTCCTCATCCTGTAAAACGGG (SEQ ID NO 53) | CCACTAACTAGTTTGTGACTTTGG (SEQ ID NO 54) |
| | D18S851 | CTGTCCTCTAGGCTCATTTAGC (SEQ ID NO 55) | TTATGAAGCAGTGATGCCAA (SEQ ID NO 56) |
| | D18S858 | AGCTGGAGAGGGATAGCATT (SEQ ID NO 57) | TGCATTGCATGAAAGTAGGA (SEQ ID NO 58) |
| | D18S877 | GATGATAGAGATGGCACATGA (SEQ ID NO 59) | TCTTCATACATGCTTTATCATGC (SEQ ID NO 60) |
| 21 | D21S11 | GTGAGTCAATTCCCCAAG (SEQ ID NO 61) | GTTGTATTAGTCAATGTTCTCC (SEQ ID NO 62) |
| | D21S1411 | ATGATGAATGCATAGATGGATG (SEQ ID NO 63) | AATGTGTGTCCTTCCAGGC (SEQ ID NO 64) |
| | D21S1413 | TTGCAGGGAAACCACAGTT (SEQ ID NO 65) | TCCTTGGAATAAATTCCCGG (SEQ ID NO 66) |
| | D21S1432 | CTTAGAGGGACAGAACTAATAGGC (SEQ ID NO 67) | AGCCTATTGTGGGTTTGTGA (SEQ ID NO 68) |
| | D21S1437 | ATGTACATGTGTCTGGGAAGG (SEQ ID NO 69) | TTCTCTACATATTTACTGCCAACA (SEQ ID NO 70) |
| | D21S1440 | GAGTTTGAAAATAAAGTGTTCTGC (SEQ ID NO 71) | CCCCACCCCTTTTAGTTTTA (SEQ ID NO 72) |
| | D21S1446 | ATGTACGATACGTAATACTTGACAA (SEQ ID NO 73) | GTCCCAAAGGACCTGCTC (SEQ ID NO 74) |
| | D21S2052 | GCACCCCTTTATACTTGGGTG (SEQ ID NO 75) | TAGTACTCTACCATCCATCTATCCC (SEQ ID NO 76) |

TABLE 3-continued

Primer Sets for STRs on Chromsomes 13, 18, 21 and X

| Ch. | STR Marker | Primer 1 | Primer 2 |
|---|---|---|---|
| | D21S2055 | AACAGAACCAATAGGCTATCTATC (SEQ ID NO 77) | TACAGTAAATCACTTGGTAGGAGA (SEQ ID NO 78) |
| X | SBMA | TCCGCGAAGTGAAGAAC (SEQ ID NO 79) | CTTGGGGAGAACCATCCTCA (SEQ ID NO 80) |
| | DXS1047 | CCGGCTACAAGTGATGTCTA (SEQ ID NO 81) | CCTAGGTAACATAGTGAGACCTTG (SEQ ID NO 82) |
| | DXS1068 | CCTCTAAAGCATAGGGTCCA (SEQ ID NO 83) | CCCATCTGAGAACACGCTG (SEQ ID NO 84) |
| | DXS1283E | AGTTTAGGAGATTATCAAGCTGG (SEQ ID NO 85) | GTTCCCATAATAGATGTATCCAG (SEQ ID NO 86) |
| | DXS6789 | TTGGTACTTAATAAACCCTCTTTT (SEQ ID NO 87) | CTAGAGGGACAGAACCAATAGG (SEQ ID NO 88) |
| | DXS6795 | TGTCTGCTAATGAATGATTTGG (SEQ ID NO 89) | CCATCCCCTAAACCTCTCAT (SEQ ID NO 90) |
| | DXS6800 | GTGGGACCTTGTGATTGTGT (SEQ ID NO 91) | CTGGCTGACACTTAGGGAAA (SEQ ID NO 92) |
| | DXS6810 | ACAGAAAACCTTTTGGGACC (SEQ ID NO 93) | CCCAGCCCTGAATATTATCA (SEQ ID NO 94) |
| | DXS7127 | TGCACTTAATATCTGGTGATGG (SEQ ID NO 95) | ATTTCTTTCCCTCTGCAACC (SEQ ID NO 96) |
| | DXS7132 | AGCCCATTTTCATAATAAATCC (SEQ ID NO 97) | AATCAGTGCTTTCTGTACTATTGG (SEQ ID NO 98) |
| | DXS8377 | CACTTCATGGCTTACCACAG (SEQ ID NO 99) | GACCTTTGGAAAGCTAGTGT (SEQ ID NO 100) |
| | DXS9893 | TGTCACGTTTACCCTGGAAC (SEQ ID NO 101) | TATTCTTCTATCCAACCAACAGC (SEQ ID NO 102) |
| | DXS9895 | TTGGGTGGGACACAGAG (SEQ ID NO 103) | CCTGGCTCAAGGAATTACAA (SEQ ID NO 104) |
| | DXS9896 | CCAGCCTGGCTGTTAGAGTA (SEQ ID NO 105) | ATATTCTTATATTCCATATGGCACA (SEQ ID NO 106) |
| | DXS9902 | TGGAGTCTCTGGGTGAAGAG (SEQ ID NO 107) | CAGGAGTATGGGATCACCAG (SEQ ID NO 108) |
| | DXS998 | CAGCAATTTTTCAAAGGC (SEQ ID NO 109) | AGATCATTCATATAACCTCAAAAGA (SEQ ID NO 110) |

What is claimed is:

1. A method of analyzing a fetal blood cell in a maternal blood sample obtained from a pregnant human female, the method comprising:

(a) obtaining the maternal blood sample;

(b) enriching the maternal blood sample for fetal blood cells to produce an enriched sample comprising fetal blood cells and maternal blood cells, wherein the enrichment increases the ratio of fetal cells to maternal cells to about 1/10,000 to about 1/10;

(c) binning fetal blood cells and maternal blood cells from the enriched sample by serial dilution, wherein the binning results in at least one bin containing an individual fetal blood cell from the enriched sample;

(d) identifying bins that contain at least one fetal blood cell using one or more fetal blood cell biomarkers;

(e) lysing fetal blood cells in the identified bins;

(f) amplifying the genomes of the lysed fetal blood cells in the identified bins to produce amplified nucleic acids; and (g) analyzing the amplified nucleic acids in bins that contain at least one fetal cell for aneuploidy using ultra-deep sequencing.

2. The method of claim 1, wherein the analyzing comprises analyzing for fetal aneuploidy, wherein the fetal aneuploidy comprises monosomy, trisomy, tetrasomy, or pentasomy of one or more chromosomes.

3. The method of claim 2, wherein the fetal aneuploidy is a fetal aneuploidy of a chromosome selected from the group consisting of chromosome 13, chromosome 18, chromosome 21, chromosome X, and chromosome Y.

4. The method of claim 2, wherein the fetal aneuploidy comprises trisomy or monosomy.

5. The method of claim 4, wherein the fetal aneuploidy comprises trisomy, and wherein the trisomy comprises trisomy 13, trisomy 18, or trisomy 21.

6. The method of claim 4, wherein the fetal aneuploidy comprises monosomy X and the chromosome suspected of being aneuploid comprises chromosome X.

7. The method of claim 1, wherein the fetal aneuploidy comprises XXX, XXY, or XYY.

8. The method of claim 1, wherein the ultra-deep sequencing produces partial genome sequences for analysis.

9. The method of claim 1, wherein the ultra-deep sequencing produces complete genome sequences for analysis.

10. The method of claim 1, wherein the whole genomes of the lysed fetal blood cells are amplified.

11. The method of claim 1, wherein the binning comprises use of a nanofluidic system.

12. The method of claim 11, wherein the nanofluidic system separates samples into droplets.

13. The method of claim 1, wherein the binning is preceded by positive selection for fetal cells.

14. The method of claim 1, wherein the binning is preceded by negative selection for non-target cells.

15. The method of claim 1, wherein the enrichment increases the ratio of fetal cells to maternal cells to about 1/100 to about 1/10.

16. The method of claim 1, wherein the enrichment increases the ratio of fetal cells to maternal cells to about 1/50 to about 1/10.

17. The method of claim 1, wherein the enrichment increases the ratio of fetal cells to maternal cells to about 1/10.

\* \* \* \* \*

UNITED STATES PATENT AND TRADEMARK OFFICE
CERTIFICATE OF CORRECTION

PATENT NO. : 10,591,391 B2
APPLICATION NO. : 13/830871
DATED : March 17, 2020
INVENTOR(S) : Stoughton et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this
First Day of December, 2020

Andrei Iancu
*Director of the United States Patent and Trademark Office*

SEQUENCE LISTING

<160> NUMBER OF SEQ ID NOS: 166

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acagaagtct gggatgtgga                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcccaaaaag acagacagaa                                               20

<210> SEQ ID NO 3
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 3
acctgttgta tggcagcagt                                                    20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agttgactct ttccccaact a                                                  21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttggtaaga aaacatctc cc                                                  22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggctgcagtt agctgtcatt                                                    20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctgggcaac aagagcaaa                                                     19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcagagaga cataattgtg                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
acctgccaaa ttttaccagg                                               20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacagagaga gggaataaac c                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atatatgcac atccatccat g                                             21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggccaaagat agatagcaag gta                                           23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acatcgctcc ttaccccatc                                               20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtacccatt aaccatcccc a                                             21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
acagaagtct gggatgtgga                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcccaaaaag acagacagaa                                              20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agagtgagat tctgtctcaa ttaa                                         24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggccctgtgt agaagctgta                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atcaggattc caggaggaaa                                              20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acctgggagg cggagctc                                                18

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 21
ggcataaaaa tagtacagca agc                                    23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atttgaacag aggcatgtac                                        20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
catggatgca gaattcacag                                        20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcatctccct gtttggtagc                                        20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agggatcttc agagaaacag g                                      21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgacactatc agctctctgg c                                      21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
ggtgcttgct gtaaatataa ttg                                             23
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
cactacagca gattgcacca                                                 20
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
caaacccgac taccagcaac                                                 20
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gagccatgtt catgccactg                                                 20
```

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
caaagagtga atgctgtaca aacagc                                          26
```

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
caagatgtga gtgtgctttt caggag                                          26
```

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atcccacagg atgcctattt                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgggagctt ttgagaagtt                                              20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcaaattttt aagtctcacc agg                                          23

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcctgtagaa agcaacaacc                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggtgacagag caagaccttg                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcctcttgtc atcccaagta                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctctcttcat ccaccattgg                                              20

```
<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctgtaagag acctgtgttg                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggaaccact tcattcttgg                                              20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atttcagacc aagataggc                                               19

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cctatttaag tttctgtaag g                                            21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggtgtaga ccctgtggaa                                              20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctgcacaaca tagtgagacc tg                                           22
```

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agattaccca gaaatgagat cagc                                            24

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcatgtgaca aaagccacac                                                 20

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agacagaaat atagatgaga atgca                                           25

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcatgtgaca aaagccacac                                                 20

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agacagaaat atagatgaga atgca                                           25

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tttccagtgg aaaccaaact                                                 20

-continued

```
<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tccagcaaca acaagagaca                                                    20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtcctcatcc tgtaaaacgg g                                                  21

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccactaacta gtttgtgact ttgg                                               24

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctgtcctcta ggctcattta gc                                                 22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttatgaagca gtgatgccaa                                                    20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agctggagag ggatagcatt                                                    20

<210> SEQ ID NO 58
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgcattgcat gaaagtagga                                              20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gatgatagag atggcacatg a                                            21

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcttcataca tgctttatca tgc                                          23

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgagtcaat tccccaag                                                18

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gttgtattag tcaatgttct cc                                           22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atgatgaatg catagatgga tg                                           22

<210> SEQ ID NO 64
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aatgtgtgtc cttccaggc                                                    19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttgcagggaa accacagtt                                                    19

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tccttggaat aaattcccgg                                                   20

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cttagaggga cagaactaat aggc                                              24

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agcctattgt gggtttgtga                                                   20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atgtacatgt gtctgggaag g                                                 21

<210> SEQ ID NO 70
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 70
ttctctacat atttactgcc aaca                                          24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gagtttgaaa ataaagtgtt ctgc                                          24

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccccacccct tttagttttta                                              20

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atgtacgata cgtaatactt gacaa                                         25

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtcccaaagg acctgctc                                                 18

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75 gcacccctt tacttgggt g                                               21

<210> SEQ ID NO 76
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 76
tagtactcta ccatccatct atccc                                           25

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aacagaacca ataggctatc tatc                                            24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tacagtaaat cacttggtag gaga                                            24

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tccgcgaagt gaagaac                                                    17

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttggggaga accatcctca                                                 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccggctacaa gtgatgtcta                                                 20

<210> SEQ ID NO 82
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 82
cctaggtaac atagtgagac cttg                                              24

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cctctaaagc atagggtcca                                                   20

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cccatctgag aacacgctg                                                    19

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agtttaggag attatcaagc tgg                                               23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gttcccataa tagatgtatc cag                                               23

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttggtactta ataaccctc tttt                                               24

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
ctagagggac agaaccaata gg                                              22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tgtctgctaa tgaatgattt gg                                              22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccatccccta aacctctcat                                                 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gtgggacctt gtgattgtgt                                                 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ctggctgaca cttagggaaa                                                 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acagaaaacc ttttgggacc                                                 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 94
cccagccctg aatattatca                                              20

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tgcacttaat atctggtgat gg                                           22

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
atttctttcc ctctgcaacc                                              20

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agcccatttt cataataaat cc                                           22

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aatcagtgct ttctgtacta ttgg                                         24

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cacttcatgg cttaccacag                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 100
gacctttgga aagctagtgt                                               20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgtcacgttt accctggaac                                               20

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tattcttcta tccaaccaac agc                                           23

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ttgggtgggg acacagag                                                 18

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cctggctcaa ggaattacaa                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccagcctggc tgttagagta                                               20

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
atattcttat attccatatg gcaca                                                  25

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tggagtctct gggtgaagag                                                        20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
caggagtatg ggatcaccag                                                        20

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cagcaatttt tcaaaggc                                                          18

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
agatcattca tataacctca aaaga                                                  25

<210> SEQ ID NO 111
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ttctaatatg caaatgcaca cagatttctg ct                                          32

<210> SEQ ID NO 112
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ttcagattca gactgaatga caccatcagt tt                                32

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ttggagtcgc aagctgaact agcg                                         24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ccaggaagtt gaggctgcag tgaa                                         24

<210> SEQ ID NO 115
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
taaagtgaga agaataact gcatcttaac ct                                 32

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tctcctttct cttcctcatc cctgcat                                      27

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gctctggaaa acaactcgac ccttctt                                      27

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gtgggagaat cgcctgagtc ct                                           22

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gtctgttatg ggactttct cagtctccat                                    30

<210> SEQ ID NO 120
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
acactgagaa gggagaaaca ctgtaaggtt ttatat                            36

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gctagatttt ccccgatgat                                              20

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
atgtaaagtg ctctcaagag tgc                                          23

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gcatgcacct gtagttccag ctact                                        25

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gagagcaacg tgtccctcct gt                                           22

<210> SEQ ID NO 125
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cagaagagac tgcccttcag actttctaaa t                                  31

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gtacacgcct gtaatcccag ctact                                         25

<210> SEQ ID NO 127
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tacaccttta aaattccaaa gaaagttctt ct                                 32

<210> SEQ ID NO 128
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
caattctgct tctcagatcc tctgacact                                     29

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ccaaggccct tcccaggct                                                19

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tgacactgct acaactcaca ccacattt                                      28

```
<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
aacccatgtt cccactggcc t                                            21

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
caaacgtgag gttgactcta ctgtcct                                      27

<210> SEQ ID NO 133
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
agactgatcc tataaggtag agttcccacc t                                 31

<210> SEQ ID NO 134
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tagagacagg atagatgata aatagataca taggtt                            36

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ttggagtcgc aagctgaact agc                                          23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gcctgagtga cagagtgaga acc                                          23

<210> SEQ ID NO 137
```

<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
tgtaataact ctacgactgt ctgtctg                                            27

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
gaataggagg tggatggatg g                                                  21

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
gtgagtcaat tccccaag                                                      18

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
gttgtattag tcaatgttct cc                                                 22

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
attttccccg atgatagtag tct                                                23

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
gcgaatgtat gattggcaat attttt                                             26

<210> SEQ ID NO 143
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
tgaggtggtg tactaccata                                               20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gatcatgcca ttgcactcta                                               20

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ccctagtgga tgataagaat aatc                                          24

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggacagatga taaatacata ggatggatgg                                    30

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ttccacacac cactggccat cttc                                          24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
aacctgagtc tgccaaggac tagc                                          24

<210> SEQ ID NO 149
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 149
ggtaagcagg tacttagtta gctac                                           25

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gttacagtga gccaaggtcg tgag                                            24

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gaggttgcac tcgagccttt gcaa                                            24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ttcctgaatc atcccagagc caca                                            24

<210> SEQ ID NO 153
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
attatccaaa agtcaaatgc cccatagg                                        28

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
atcgaaaata tggttattga agtagctg                                        28

<210> SEQ ID NO 155
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 155
gtgggctgaa aagctcccga ttat                                            24

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
attcaaaggg tatctgggct ctgg                                            24

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
actggcacag aacaggcact tagg                                            24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ggaggaactg ggaaccacac aggt                                            24

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tcgagtgcat tccattccg                                                  19

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
atggaatggc atcaaacgga a                                               21

<210> SEQ ID NO 161
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 161
tggctgtcca ttcca                                                    15

<210> SEQ ID NO 162
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
atgcagcaag gcacagacta arcaaggaga sgcaaaattt tcrtagggga gagaaatggg   60
tcatt                                                               65

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
atgcagcaag gcacagacta cg                                            22

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164 agagggaga gaaatgggtc att                                            23

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
caaggcacag actaagcaag gagag                                         25

<210> SEQ ID NO 166
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ggcaaaattt tcatagggga gagaaatggg tcatt                              35
```